(12) United States Patent
Lerner

(10) Patent No.: US 10,251,779 B2
(45) Date of Patent: *Apr. 9, 2019

(54) DEVICE AND METHOD FOR INTRAOCULAR DRUG DELIVERY

(71) Applicant: OcuJect, LLC, Newport Beach, CA (US)

(72) Inventor: Leonid E. Lerner, Corona Del Mar, CA (US)

(73) Assignee: OcuJect, LLC, Newport Beach, CA (US)

( * ) Notice: Subject to any disclaimer, the term of this patent is extended or adjusted under 35 U.S.C. 154(b) by 474 days.

This patent is subject to a terminal disclaimer.

(21) Appl. No.: 15/137,466

(22) Filed: Apr. 25, 2016

(65) Prior Publication Data

US 2016/0310318 A1  Oct. 27, 2016

Related U.S. Application Data

(63) Continuation of application No. 13/249,087, filed on Sep. 29, 2011, now Pat. No. 9,320,647, which is a
(Continued)

(51) Int. Cl.
*A61F 9/00* (2006.01)
*A61F 9/007* (2006.01)
(Continued)

(52) U.S. Cl.
CPC ........ *A61F 9/0017* (2013.01); *A61F 9/00736* (2013.01); *A61M 5/2033* (2013.01);
(Continued)

(58) Field of Classification Search
CPC .... A61F 9/007; A61F 9/00736; A61F 9/0136; A61F 2009/00844; A61F 2009/00851;
(Continued)

(56) References Cited

U.S. PATENT DOCUMENTS

| 2,674,246 A | 3/1952 | Bower |
| 3,134,380 A | 5/1964 | Armao |

(Continued)

FOREIGN PATENT DOCUMENTS

| CN | 1516603 | 7/2004 |
| JP | 5-43663 | 2/1993 |

(Continued)

OTHER PUBLICATIONS

U.S. Appl. No. 15/917,540, filed Mar. 9, 2018, Lerner.
(Continued)

*Primary Examiner* — Andrew M Gilbert
(74) *Attorney, Agent, or Firm* — Knobbe Martens Olson & Bear LLP

(57) ABSTRACT

Injection devices for delivering pharmaceutical formulations into the eye are described. The devices may be integrated to include features that allow safe and atraumatic manipulation of the devices with one hand. For example, accurate placement, including proper angulation, of the device on the eye and injection of a pharmaceutical formulation into the eye can be performed using one hand. The devices may also include improved safety features. For example, the devices may include an actuation mechanism that controls the rate and depth of injection into the eye. Some devices include a dynamic resistance component capable of adjusting the amount of pressure applied to the eye surface. Related methods and systems comprising the devices are also described.

7 Claims, 35 Drawing Sheets

Related U.S. Application Data continuation-in-part of application No. 13/077,929, filed on Mar. 31, 2011, now Pat. No. 9,408,746.

(60) Provisional application No. 61/384,636, filed on Sep. 20, 2010, provisional application No. 61/341,582, filed on Mar. 31, 2010.

(51) Int. Cl.
| | |
|---|---|
| *A61M 5/32* | (2006.01) |
| *A61M 5/20* | (2006.01) |
| *A61M 5/42* | (2006.01) |
| *A61M 5/46* | (2006.01) |
| *A61M 5/48* | (2006.01) |

(52) U.S. Cl.
CPC .......... *A61M 5/3243* (2013.01); *A61M 5/427* (2013.01); *A61M 5/46* (2013.01); *A61M 5/20* (2013.01); *A61M 5/204* (2013.01); *A61M 5/2053* (2013.01); *A61M 5/482* (2013.01); *A61M 2005/206* (2013.01); *A61M 2005/3267* (2013.01); *A61M 2205/585* (2013.01); *A61M 2205/587* (2013.01); *A61M 2205/75* (2013.01); *A61M 2210/0612* (2013.01)

(58) Field of Classification Search
CPC .. A61M 5/3243; A61M 5/3257; A61M 5/321; A61M 2005/3217
See application file for complete search history.

(56) References Cited

U.S. PATENT DOCUMENTS

| | | | |
|---|---|---|---|
| 3,336,924 A | 8/1967 | Sarnoff | |
| 3,403,679 A | 10/1968 | Sinclair et al. | |
| 3,406,687 A | 10/1968 | James | |
| 4,127,131 A | 11/1978 | Vaillancourt | |
| 4,416,663 A | 11/1983 | Hall | |
| 4,553,962 A | 11/1985 | Brunet | |
| 4,564,054 A | 1/1986 | Gustavsson | |
| 4,610,668 A | 9/1986 | Fleig | |
| 4,695,274 A | 9/1987 | Fox | |
| 4,929,241 A | 5/1990 | Kulli | |
| 4,998,922 A | 3/1991 | Kuracina et al. | |
| 5,041,088 A | 8/1991 | Ritson et al. | |
| 5,059,184 A | 10/1991 | Dyke | |
| 5,088,986 A | 2/1992 | Nusbaum | |
| 5,137,516 A | 8/1992 | Rand et al. | |
| 5,199,441 A | 4/1993 | Hogle | |
| 5,300,084 A | 4/1994 | Johnson | |
| 5,304,138 A | 4/1994 | Mercado | |
| 5,304,151 A | 4/1994 | Kuracina | |
| 5,328,482 A | 7/1994 | Sircom et al. | |
| 5,334,163 A | 8/1994 | Sinnett | |
| 5,415,645 A | 5/1995 | Friend et al. | |
| 5,429,612 A | 7/1995 | Berthier | |
| 5,462,995 A | 10/1995 | Hosaka et al. | |
| 5,466,261 A | 11/1995 | Richelsoph et al. | |
| 5,472,430 A | 12/1995 | Vaillancourt et al. | |
| 5,487,733 A | 1/1996 | Caizza et al. | |
| 5,549,568 A | 8/1996 | Shields | |
| 5,584,818 A | 12/1996 | Morrison | |
| 5,688,253 A | 11/1997 | Paradis | |
| 5,713,872 A | 2/1998 | Feuerborn | |
| 5,725,493 A | 3/1998 | Avery et al. | |
| 5,830,152 A | 11/1998 | Tao | |
| 5,873,856 A | 2/1999 | Hjertman et al. | |
| 6,099,504 A | 8/2000 | Gross et al. | |
| 6,209,738 B1 | 4/2001 | Jansen | |
| 6,251,090 B1 | 6/2001 | Avery et al. | |
| 6,253,804 B1 | 7/2001 | Safabash | |
| 6,299,603 B1 | 10/2001 | Hecker et al. | |
| 6,309,374 B1 | 10/2001 | Hecker et al. | |
| 6,368,308 B1 | 4/2002 | Nerny | |
| 6,443,929 B1 | 9/2002 | Kuracina et al. | |
| 6,447,482 B1 | 9/2002 | Ronborg et al. | |
| 6,729,370 B2 | 5/2004 | Norton | |
| 7,314,464 B2 | 1/2008 | Giambattista et al. | |
| 7,364,570 B2 | 4/2008 | Gerondale et al. | |
| 7,374,558 B2 | 5/2008 | Kirchhofer | |
| 7,396,343 B2 | 7/2008 | Brown | |
| 7,416,540 B2 | 8/2008 | Edwards et al. | |
| 7,674,243 B2 | 3/2010 | Dacquay et al. | |
| 7,678,078 B1 | 3/2010 | Peyman et al. | |
| 7,749,194 B2 | 7/2010 | Edwards et al. | |
| 7,871,399 B2 | 1/2011 | Dacquay et al. | |
| 7,901,382 B2 | 3/2011 | Daily et al. | |
| 7,918,814 B2 | 4/2011 | Prausnitz et al. | |
| 8,043,268 B1 | 10/2011 | Marks | |
| 8,221,353 B2 | 7/2012 | Cormier et al. | |
| 8,287,494 B2 | 10/2012 | Ma | |
| 8,556,861 B2 | 10/2013 | Tsals | |
| 9,320,647 B2 * | 4/2016 | Lerner | A61F 9/0017 |
| 9,408,746 B2 | 8/2016 | Lerner et al. | |
| 9,421,129 B2 | 8/2016 | Lerner | |
| 9,504,603 B2 | 11/2016 | Lerner | |
| 9,603,739 B2 | 3/2017 | Lerner | |
| 9,669,988 B2 | 6/2017 | Kojima | |
| 9,849,251 B2 | 12/2017 | Crawford | |
| 9,913,750 B2 | 3/2018 | Lerner | |
| 2001/0008961 A1 | 7/2001 | Hecker et al. | |
| 2002/0004648 A1 | 1/2002 | Larsen et al. | |
| 2002/0004650 A1 | 1/2002 | Kuracina et al. | |
| 2002/0095121 A1 | 7/2002 | Norton | |
| 2002/0123721 A1 | 9/2002 | Payne et al. | |
| 2002/0133122 A1 | 9/2002 | Giambattista et al. | |
| 2002/0169421 A1 | 11/2002 | McWethy et al. | |
| 2002/0198553 A1 | 12/2002 | Schumer et al. | |
| 2003/0040706 A1 | 2/2003 | Kuracina et al. | |
| 2003/0060763 A1 | 3/2003 | Penfold et al. | |
| 2003/0078546 A1 | 4/2003 | Jensen | |
| 2004/0210207 A1 | 10/2004 | Amisar | |
| 2005/0113806 A1 | 5/2005 | De Carvalho et al. | |
| 2006/0047250 A1 | 3/2006 | Hickingbotham et al. | |
| 2006/0089607 A1 | 4/2006 | Chen | |
| 2006/0258977 A1 | 11/2006 | Lee | |
| 2007/0005016 A1 | 1/2007 | Williams | |
| 2007/0027452 A1 | 2/2007 | Varner et al. | |
| 2007/0244442 A1 | 10/2007 | Chowhan | |
| 2007/0270767 A1 | 11/2007 | Khieu et al. | |
| 2007/0270768 A1 | 11/2007 | Dacquay et al. | |
| 2008/0097390 A1 | 4/2008 | Dacquay et al. | |
| 2008/0114305 A1 | 5/2008 | Gerondale | |
| 2008/0271277 A1 | 11/2008 | Mizote et al. | |
| 2008/0300574 A1 | 12/2008 | Belson | |
| 2009/0269356 A1 | 10/2009 | Epstein et al. | |
| 2010/0010452 A1 | 1/2010 | Paques et al. | |
| 2010/0020150 A1 | 1/2010 | Love | |
| 2010/0030150 A1 * | 2/2010 | Paques | A61F 9/0017 604/116 |
| 2010/0100054 A1 | 4/2010 | Cormier et al. | |
| 2010/0137831 A1 | 6/2010 | Tsals | |
| 2010/0152646 A1 * | 6/2010 | Girijavallabhan | A61F 9/0017 604/22 |
| 2010/0152676 A1 | 6/2010 | Clements et al. | |
| 2010/0191224 A1 | 7/2010 | Butcher | |
| 2010/0241102 A1 | 9/2010 | Ma | |
| 2010/0318034 A1 | 12/2010 | Goncalves | |
| 2011/0054441 A1 | 3/2011 | Erickson et al. | |
| 2012/0078224 A1 | 3/2012 | Lerner | |
| 2012/0123353 A1 | 5/2012 | Veckeneer et al. | |
| 2012/0265149 A1 | 10/2012 | Lerner | |
| 2013/0023824 A1 | 1/2013 | Coroneo | |
| 2013/0172818 A1 | 7/2013 | Schraga | |
| 2013/0267910 A1 | 10/2013 | Hemmann et al. | |
| 2013/0296797 A1 | 11/2013 | Liversidge | |
| 2013/0296825 A1 | 11/2013 | Lerner | |
| 2014/0039456 A1 | 2/2014 | Lerner | |
| 2014/0124542 A1 | 5/2014 | Kojima | |
| 2014/0261861 A1 | 9/2014 | Ivosevic | |
| 2015/0366708 A1 | 12/2015 | Lerner | |
| 2016/0074211 A1 | 3/2016 | Lerner | |
| 2016/0310318 A1 | 10/2016 | Lerner | |

(56) References Cited

U.S. PATENT DOCUMENTS

| | | |
|---|---|---|
| 2016/0338877 A1 | 11/2016 | Lerner et al. |
| 2017/0100284 A1 | 4/2017 | Lerner |
| 2017/0165113 A1 | 6/2017 | Lerner |
| 2017/0172795 A1 | 6/2017 | Lerner |
| 2018/0228649 A1 | 8/2018 | Lerner |
| 2018/0263816 A1 | 9/2018 | Lerner |

FOREIGN PATENT DOCUMENTS

| | | |
|---|---|---|
| JP | 6-157672 | 6/1994 |
| JP | 2003-518987 | 6/2003 |
| JP | 2008-062088 | 3/2008 |
| WO | WO 2006/082350 | 8/2006 |
| WO | WO 2007/058966 | 5/2007 |
| WO | WO 2008/084064 | 7/2008 |
| WO | WO 2009/089409 | 7/2009 |
| WO | WO 2010/019936 | 8/2009 |
| WO | WO 2011/123722 | 10/2011 |
| WO | WO 2012/019136 | 2/2012 |
| WO | WO 2012/134528 | 10/2012 |

OTHER PUBLICATIONS

U.S. Appl. No. 16/057,758, filed Aug. 7, 2018, Lerner.
Australian Office Action dated Aug. 19, 2015 for AU Patent Application No. 2011235002 in 3 pages.
European Search Report dated Aug. 6, 2015, for EP Application No. 11862044.2 in 6 pages.
European Search Report dated Oct. 21, 2015, for EP Application No. 13772386.2 in 5 pages.
Foreign Office Action and translation received in Chinese Application No. 201180026683.2 dated Aug. 25, 2014 in 23 pages.
International Search Report/ Written Opinion dated May 27, 2011, for PCT Application No. PCT/US11/30840 filed on Mar. 31, 2011, 5 pages.
International Search Report/Written Opinion dated Feb. 15, 2012, for PCT Application No. PCT/US11/53944 filed on Sep. 29, 2011, 7 pages.
Notice of Allowance dated Apr. 25, 2016 in U.S. Appl. No. 13/077,929 in 14 pages.
Notice of Allowance dated Apr. 26, 2016 in U.S. Appl. No. 13/841,144 in 16 pages.
Notice of Allowance dated Mar. 3, 2016 in Japanese patent application No. 2013-502871 in 3 pages.
PCT Search Report and Written Opinion dated Jun. 17, 2013 in International application No. PCT/US2013/034693 in 8 pages.
PCT Search Report and Written Opinion dated Mar. 3, 2015 in International application No. PCT/US2014/059124 in 22 pages.
Translation of Foreign Office Action received in Japanese Application No. 2013-502871 dated Jan. 23, 2015 in 7 pages.
West Pharmaceutical Services Regional News vol. 5 No. 2 Dated Jul. 2008 in 3 pages.
English Translation of Foreign Office Action in Chinese Application No. 201180026683.2 dated Nov. 30, 2015 in 2 pages.
English Translation of Foreign Office Action received in Chinese Application No. 201180026683.2 dated May 11, 2015 in 4 pages.
English Translation of Office Action in Japanese Application No. 2016-522002 dated Jul. 6, 2018 in 6 pages.

* cited by examiner

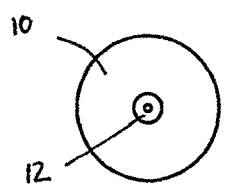 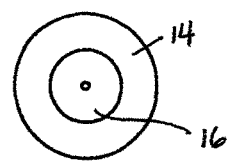
FIG. 1A    FIG. 1B
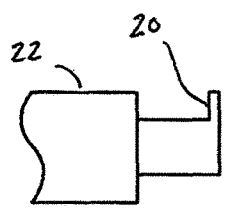 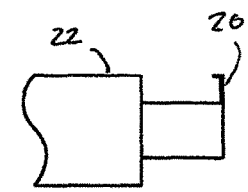 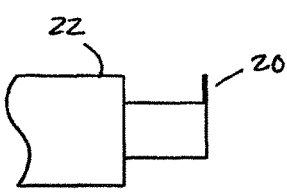
FIG. 2A    FIG. 2B    FIG. 2C
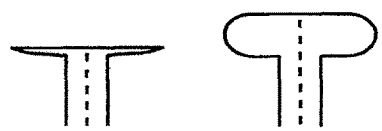
FIG. 3A1                FIG. 3B1
FIG. 3A2                FIG. 3B2
FIG. 3A3                FIG. 3B3

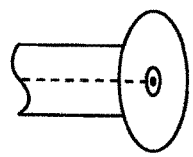  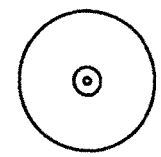
FIG. 4A    FIG. 4B1    FIG. 4B2
FIG. 5A1   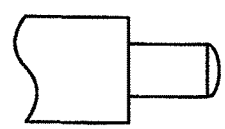 FIG. 5B1
FIG. 5A2 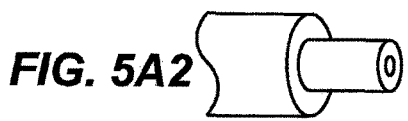  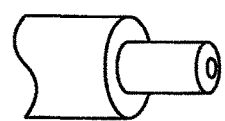 FIG. 5B2
FIG. 6A1   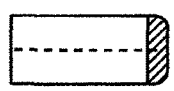 FIG. 6A2
FIG. 6B1 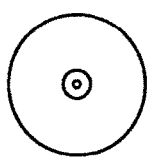  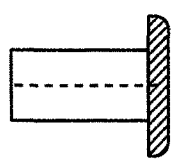 FIG. 6B2

FIG. 7A1 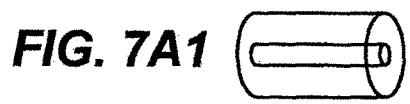  FIG. 7A2
FIG. 7B1 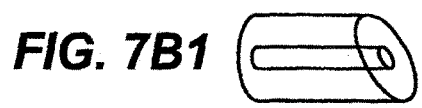  FIG. 7B2
FIG. 7C1 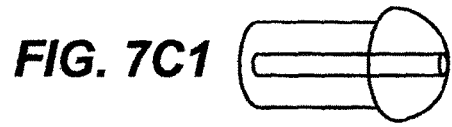  FIG. 7C2

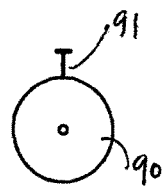 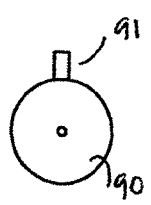 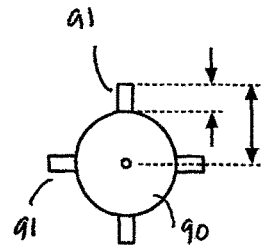
*FIG. 9A*  *FIG. 9B*  *FIG. 9C*
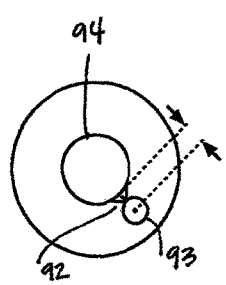 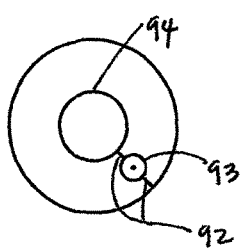 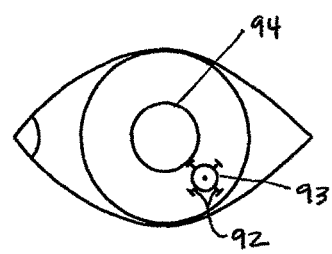
*FIG. 10A*  *FIG. 10B*  *FIG. 10C*
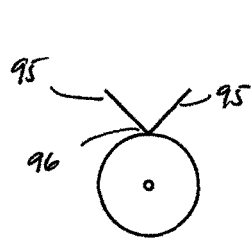 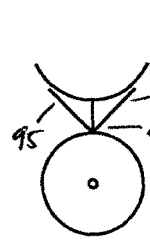 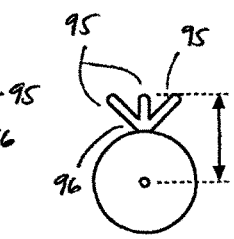 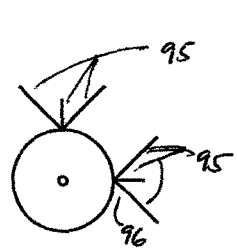
*FIG. 11A*  *FIG. 11B*  *FIG. 11C*  *FIG. 11D*

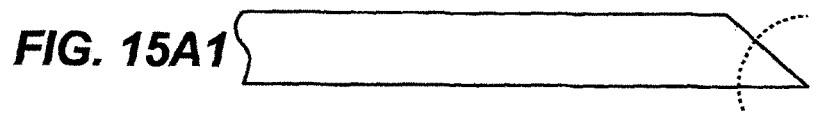
FIG. 15A1
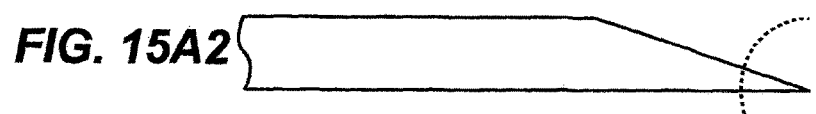
FIG. 15A2
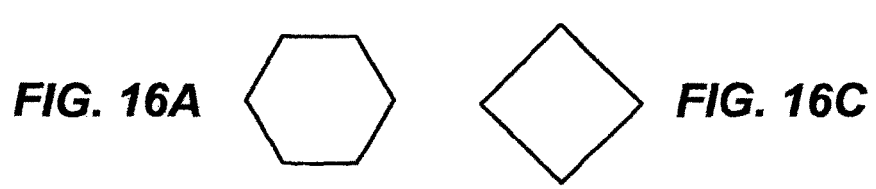
FIG. 16A   FIG. 16C
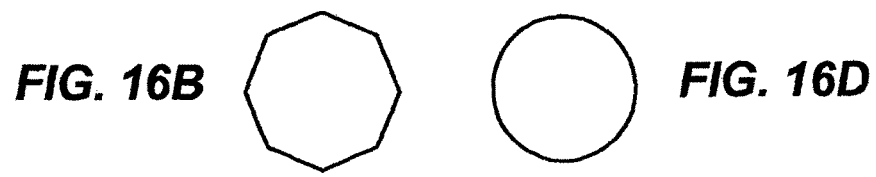
FIG. 16B   FIG. 16D
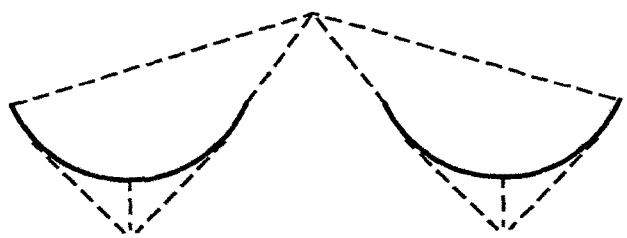
FIG. 17

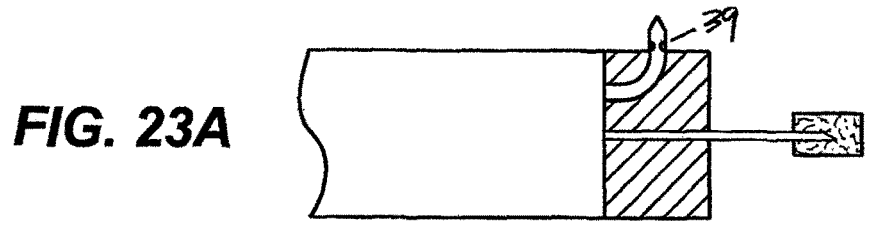
FIG. 23A
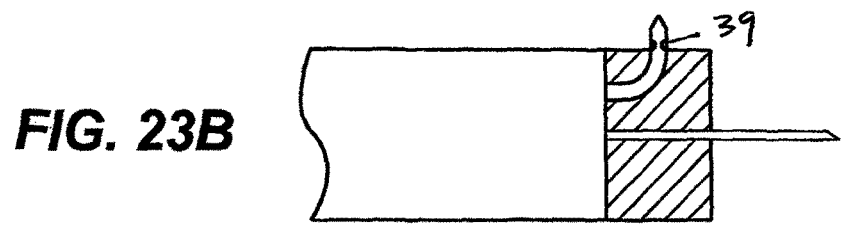
FIG. 23B
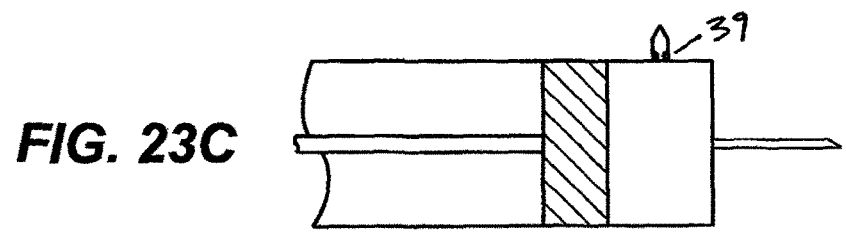
FIG. 23C
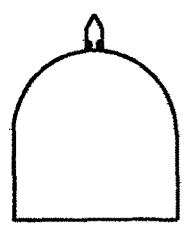 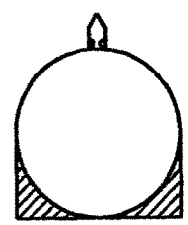 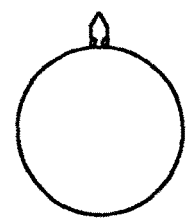
FIG. 24A   FIG. 24B   FIG. 24C
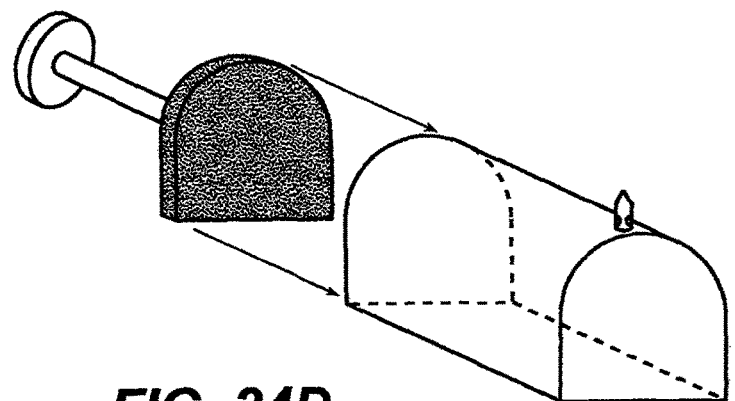
FIG. 24D

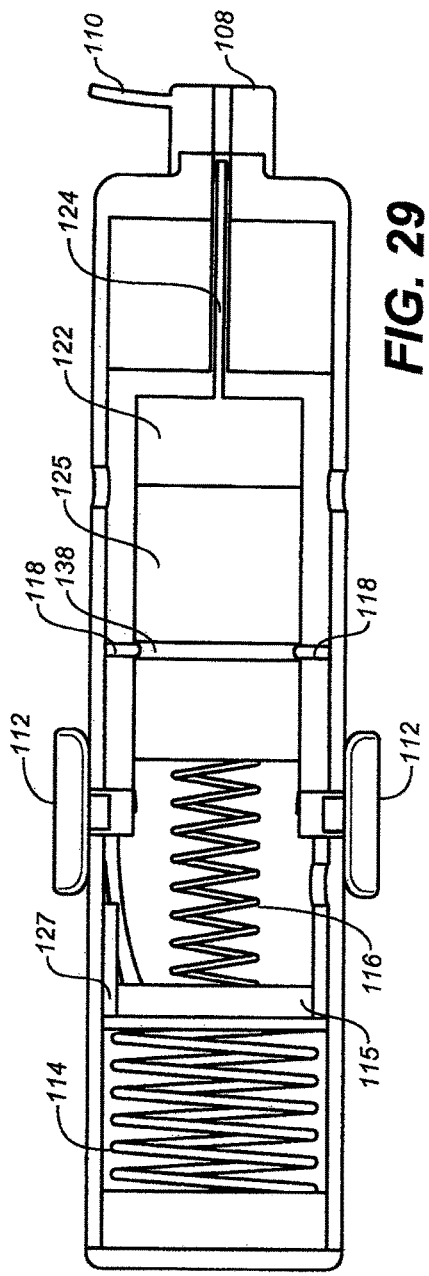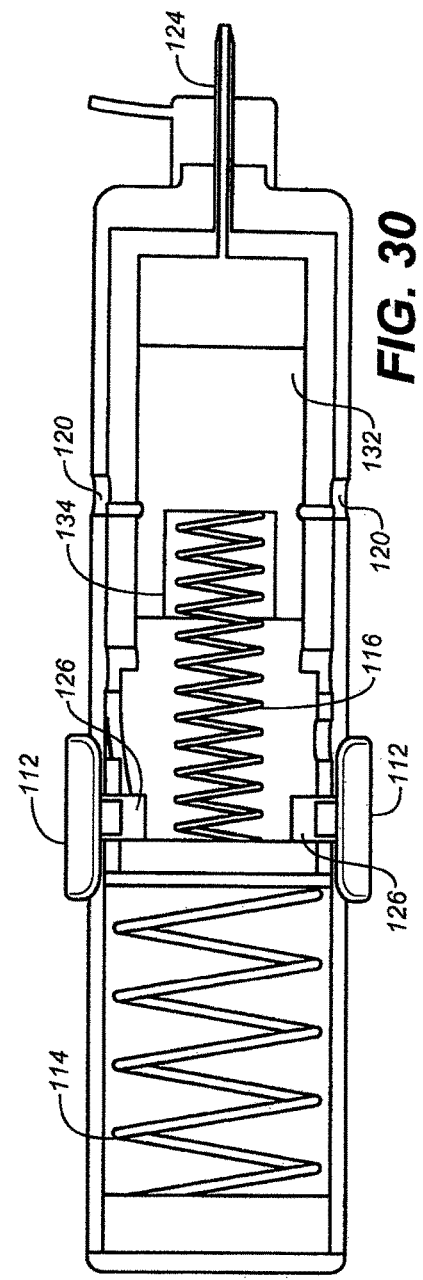

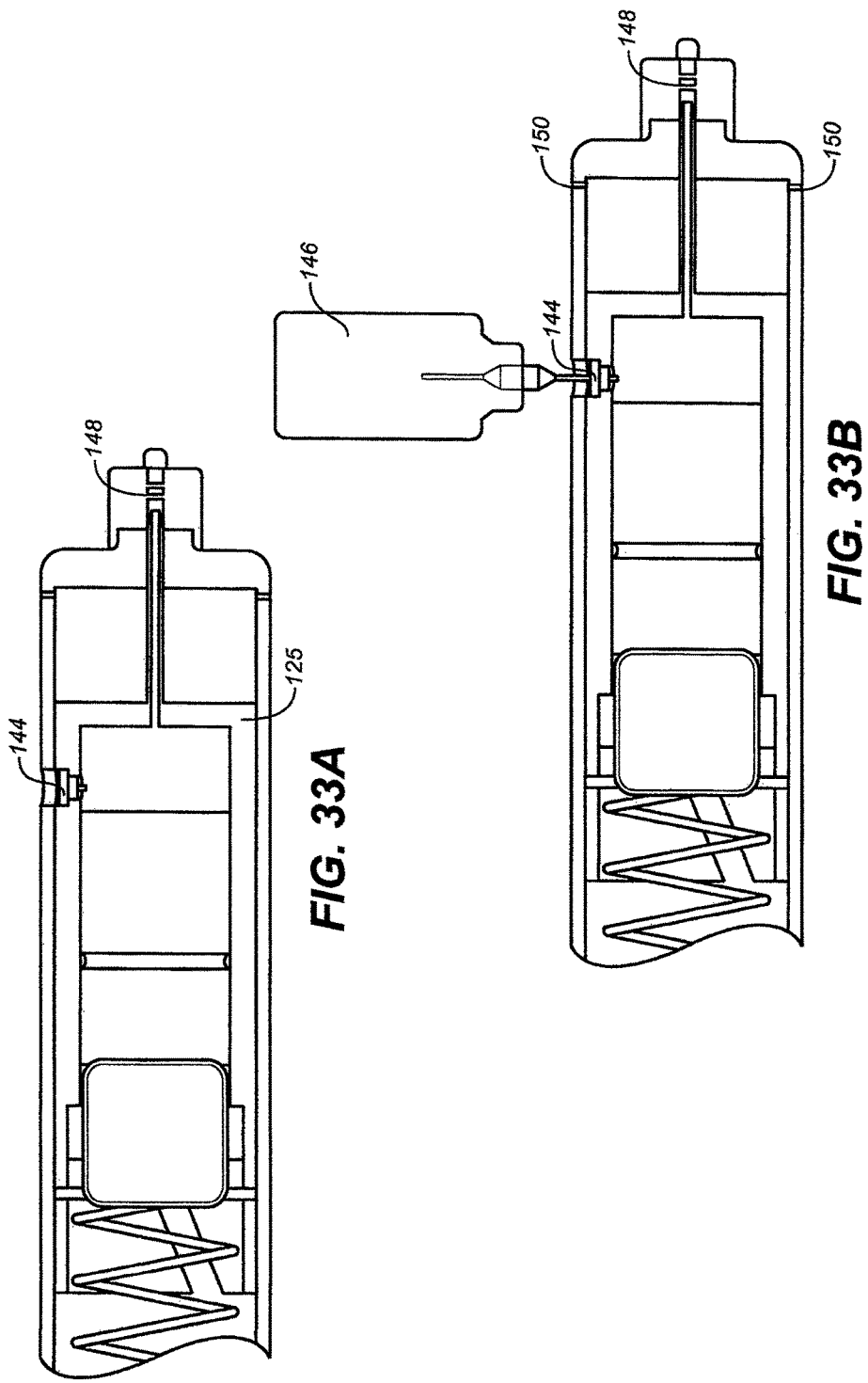

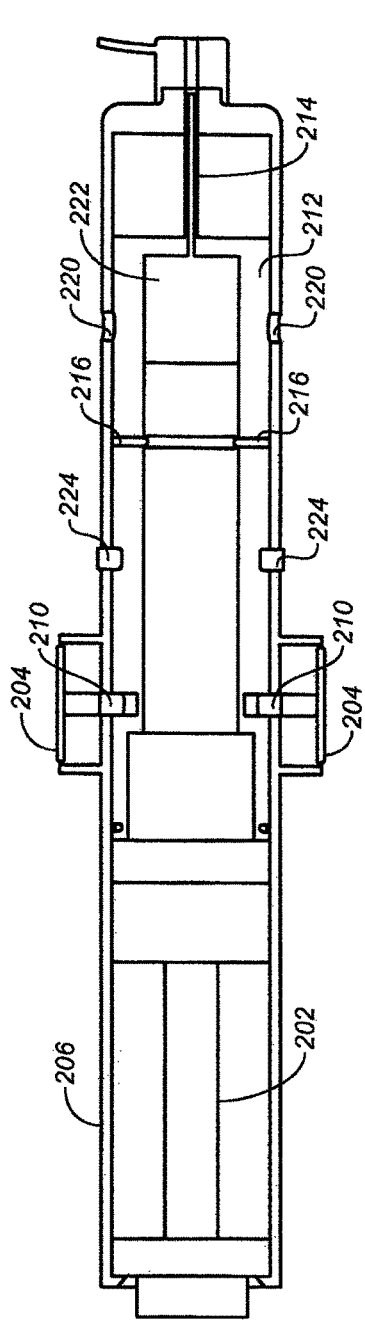
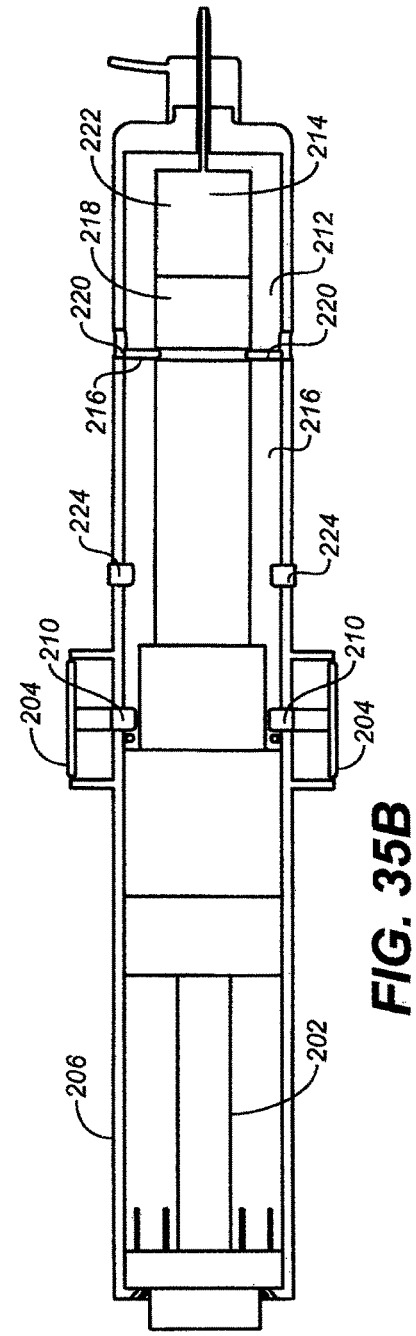

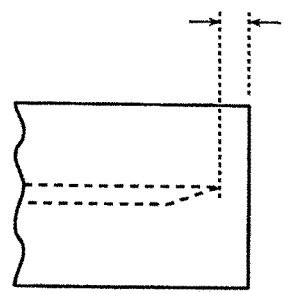
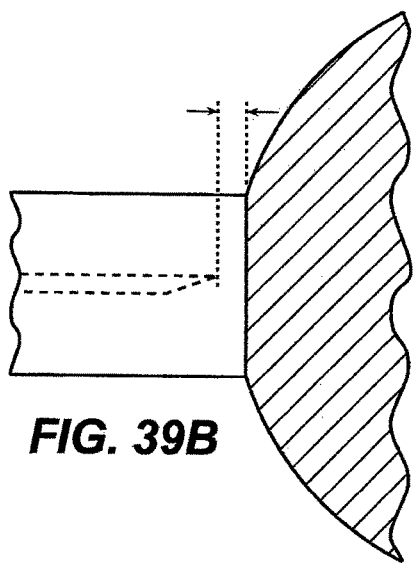
FIG. 39A     FIG. 39B
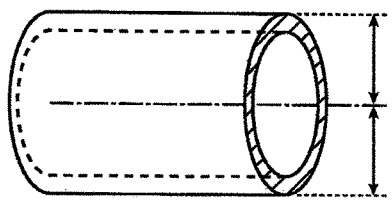
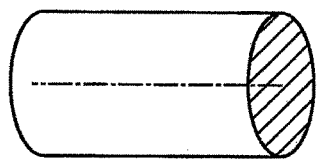
FIG. 39C     FIG. 39D
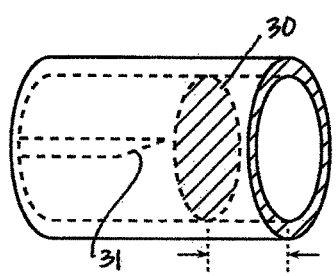
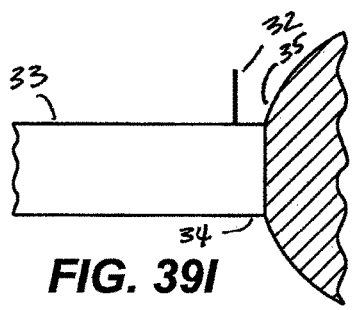
FIG. 39E     FIG. 39I
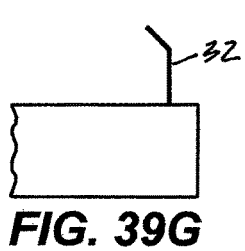
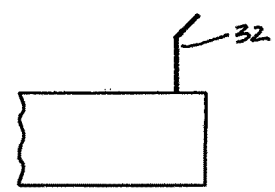
FIG. 39F     FIG. 39G     FIG. 39H

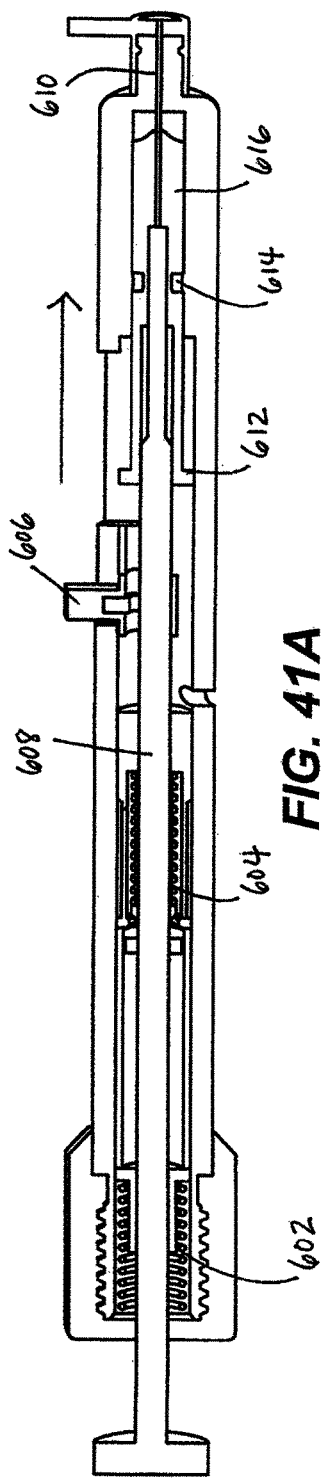
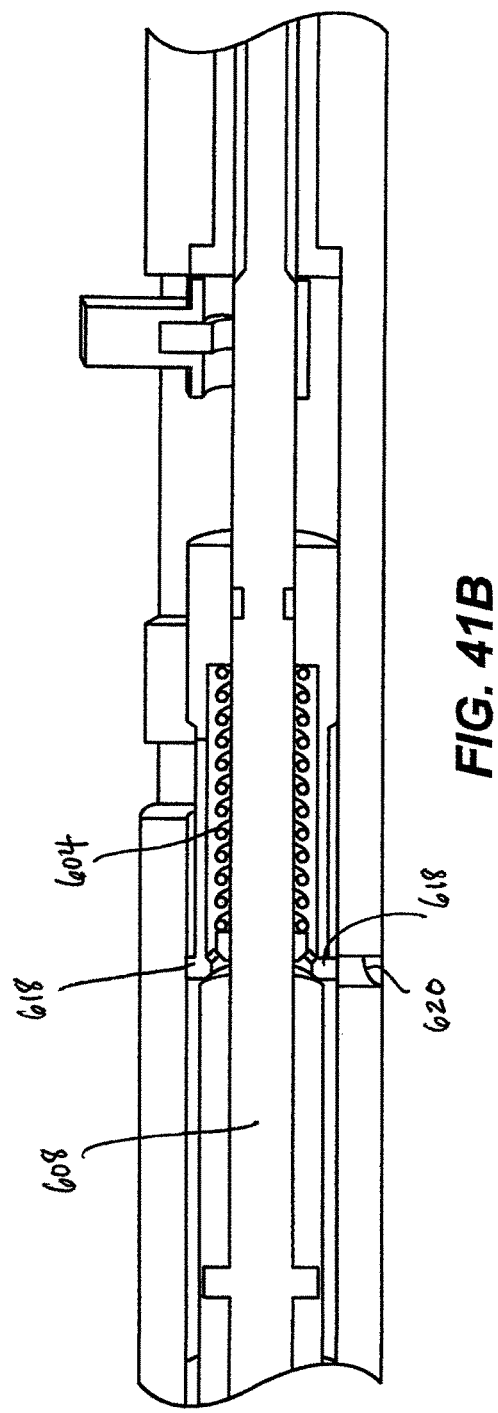
FIG. 41A
FIG. 41B

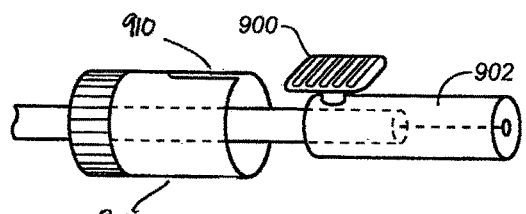 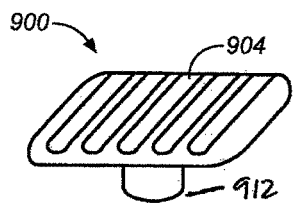
FIG. 45A    FIG. 45B
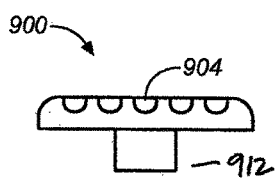 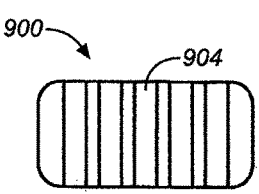
FIG. 45C    FIG. 45D FIG. 45G     FIG. 45H     FIG. 45I 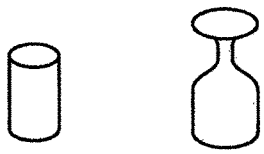
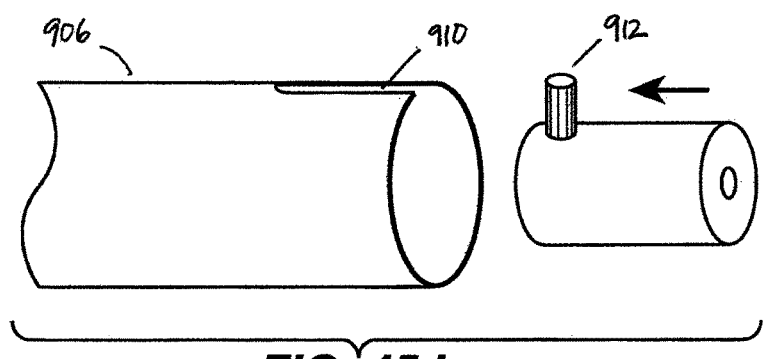
FIG. 45J

DEVICE AND METHOD FOR INTRAOCULAR DRUG DELIVERY

CROSS-REFERENCE TO RELATED APPLICATIONS

This application is a continuation of U.S. application Ser. No. 13/249,087 filed on Sep. 29, 2011, which is a continuation in part of U.S. application Ser. No. 13/077,929, filed on Mar. 31, 2011, which claims priority to U.S. Provisional Application Ser. No. 61/341,582, filed on Mar. 31, 2010, and U.S. Provisional Application Ser. No. 61/384,636, filed on Sep. 20, 2010, each of the foregoing of which are hereby incorporated by reference in their entireties.

FIELD

Described here are devices that are configured to safely and accurately deliver pharmaceutical formulations into the eye. Specifically, the devices may integrate various features that allow easy manipulation of the devices, and which may be beneficial for positioning of the devices on the ocular surface and for injecting pharmaceutical formulations atraumatically within the eye. Systems and methods for intraocularly delivering the pharmaceutical formulations using the devices are also described.

BACKGROUND

The eye is a complex organ comprised of many parts that enable the process of sight. Vision quality depends on the condition of each individual part and the ability of these parts to work together. For example, vision may be affected by conditions that affect the lens (e.g., cataracts), retina (e.g., CMV retinitis), or the macula (e.g., macular degeneration). Topical and systemic drug formulations have been developed to treat these and other ocular conditions, but each has its drawbacks. For example, topical therapies that are applied on the surface of the eye typically possess short residence times due to tear flow that washes them out of the eye. Furthermore, delivery of drugs into the eye is limited due to the natural barrier presented by the cornea and sclera, and additional structures if the intended target resides within the posterior chamber. With respect to systemic treatments, high doses of drug are often required in order to obtain therapeutic levels within the eye, which increases the risk of adverse side-effects.

Alternatively, intravitreal injections have been performed to locally deliver pharmaceutical formulations into the eye. The use of intravitreal injections has become more common due to the increased availability of anti-vascular endothelial growth factor agents for the treatment of acute macular degeneration (AMD). Agents approved by the FDA for intravitreal injection to treat AMD include ranibizumab (Lucentis®: Genetech, South San Francisco, Calif.) and pegaptanib sodium (Macugen®: Eyetech Pharmaceuticals, New York, N.Y.). In addition, intravitreal bevacizumab (Avastin®: Genentech, South San Francisco, Calif.) has been widely used in an off-label application to treat choroidal neovascularization. Increased interest in developing new drugs for delivery directly into the vitreous for the treatment of macular edema, retinal vein occlusion, and vitreous hemorrhage also exists.

Currently, commercially available intravitreal injection devices lack many features that are useful in exposing the site of injection, stabilizing the device against the sclera, and/or controlling the angle and depth of injection. Many of the devices described in the patent literature, e.g., WO 2008/084064 and U.S. 2007/0005016, are also part of multi-component systems that are generally time consuming to set up and use. The increased procedure time associated with these devices may in turn increase the risk of complications. Further, having to manipulate many components by itself may increase the risk of complications due to user error. A serious complication of intraocular injection is intraocular infection, termed endophthalmitis that occurs due to the introduction of pathogenic organisms such as bacteria from the ocular surface into the intraocular environment, or trauma to the ocular surface tissues such as corneal or conjunctival abrasion.

Accordingly, new devices for performing intravitreal injections would be desirable. Ergonomic devices that simplify the injection procedure and reduce the risk of complications would be useful. Devices that accurately and atraumatically inject drugs, e.g., liquid, semisolid, or suspension-based drugs, into the eye would also be useful.

SUMMARY

Described here are devices, methods, and systems for delivering pharmaceutical formulations into the eye. The devices may be integrated. By "integrated" it is meant that various features that may be beneficial in delivering the pharmaceutical formulations into the eye, e.g., in a safe, sterile, and accurate manner, are combined into a single device. For example, features that may aid appropriate placement on the desired eye surface site, help position the device so that the intraocular space is accessed at the proper angle, help to keep the device tip stable without moving or sliding on the ocular surface once it has been positioned during the entire drug injection, adjust or control intraocular pressure, and/or help to minimize trauma, e.g., from the force of drug injection or contact or penetration of the eye wall itself, may be integrated into a single device. More specifically, the integrated devices may be used in minimizing trauma due to direct contact with the target tissue or indirectly through force transmission through another tissue or tissues such as the eye wall or vitreous gel, as well as minimizing trauma to the cornea, conjunctiva, episclera, sclera, and intraocular structures including, but not limited to, the retina, the choroid, the ciliary body, and the lens, as well as the blood vessels and nerves associated with these structures. Features that may be beneficial in reducing the risk of intraocular infectious inflammation such as endophthalmitis and those that may reduce pain may also be included. It should be understood that the pharmaceutical formulations may be delivered to any suitable target location within the eye, e.g., the anterior chamber or posterior chamber. Furthermore, the pharmaceutical formulations may include any suitable active agent and may take any suitable form. For example, the pharmaceutical formulations may be a solid, semi-solid, liquid, etc. The pharmaceutical formulations may also be adapted for any suitable type of release. For example, they may be adapted to release an active agent in an immediate release, controlled release, delayed release, sustained release, or bolus release fashion.

In general, the devices described here include a housing sized and shaped for manipulation with one hand. The housing typically has a proximal end and a distal end, and an ocular contact surface at the housing distal end. A conduit in its pre-deployed state will usually reside within the housing. The conduit will be at least partially within the housing in its deployed state. In some instances, the conduit is slidably attached to the housing. The conduit will generally have a proximal end, a distal end, and a lumen extending therethrough. An actuation mechanism may be contained within the housing that is operably connected to the conduit and a reservoir for holding an active agent. A trigger may also be coupled to the housing and configured to activate the actuation mechanism. In one variation, a trigger is located on the side of the device housing in proximity to the device tip at the ocular contact surface (the distance between the trigger and device tip ranging between 5 mm to 50 mm, between 10 mm to 25 mm, or between 15 mm to 20 mm), so that the trigger can be easily activated by a fingertip while the device is positioned over the desired ocular surface site with the fingers of the same hand. In another variation, a trigger is located on the side of the device housing at 90 degrees to a measuring component, so that when the device tip is placed on the eye surface perpendicular to the limbus, the trigger can be activated with the tip of the second or third finger of the same hand that positions the device on the ocular surface. In one variation, a measuring component is attached to the ocular contact surface. In some variations, a drug loading mechanism is also included.

The actuation mechanism may be manual, automated, or partially automated. In one variation, the actuation mechanism is a spring-loaded actuation mechanism. Here the mechanism may include either a single spring or two springs. In another variation, the actuation mechanism is a pneumatic actuation mechanism.

The application of pressure to the surface of the eye may be accomplished and further refined by including a dynamic resistance component to the injection device. The dynamic resistance component may include a slidable element coupled to the housing. In some variations, the slidable element comprises a dynamic sleeve configured to adjust the amount of pressure applied to the eye surface. In other variations, the dynamic resistance component is configured as an ocular wall tension control mechanism.

In one variation, the injection device includes a housing sized and shaped for manipulation with one hand, the housing having a proximal end and a distal end, a resistance band at least partially surrounding the housing having a thickness between about 0.01 mm to about 5 mm, a dynamic resistance component having proximal end and a distal end, an ocular contact surface at the housing or device distal end; a conduit at least partially within the housing, the conduit having a proximal end, a distal end, and a lumen extending therethrough, and an actuation mechanism coupled to the housing and operably connected to the conduit and a reservoir for holding an active agent.

In another variation, the injection device includes integrated components and includes a housing sized and shaped for manipulation with one hand, the housing having a proximal end and a distal end, and a sectoral measuring component coupled to a distal end of the housing or device. The sectoral measuring component may have a circumference or periphery, or have a central (core) member having a proximal end, a distal end, and a circumference, and comprising a plurality of radially extending members. The injection device may also include a conduit at least partially within the housing, the conduit having a proximal end, a distal end, and a lumen extending therethrough, an actuation mechanism coupled to the housing and operably connected to the conduit and a reservoir for holding an active agent, and a dynamic resistance component.

In yet a further variation, the injection device may include a housing sized and shaped for manipulation with one hand, the housing having a wall, a proximal end and a distal end, an ocular contact surface at the housing or device distal end, a conduit at least partially within the housing, the conduit having a proximal end, a distal end, and a lumen extending therethrough, an actuation mechanism coupled to the housing and operably connected to a reservoir for holding an agent, a dynamic resistance component, and a filter coupled to the device.

In use, the devices deliver drug into the intraocular space by positioning an ocular contact surface of the integrated device on the surface of an eye, where the device further comprises a reservoir for holding an active agent and an actuation mechanism, and applying pressure against the surface of the eye at a target injection site using the ocular contact surface, and then delivering an active agent from the reservoir into the eye by activating the actuation mechanism. The steps of positioning, applying, and delivering are completed with one hand. In some instances, a topical anesthetic is applied to the surface of the eye before placement of the device on the eye. An antiseptic may also be applied to the surface of the eye before placement of the device on the eye.

The application of pressure against the surface of the eye using the ocular contact surface may also generate an intraocular pressure ranging between 15 mm Hg to 120 mm Hg, between 20 mm Hg to 90 mm Hg, or between 25 mm Hg to 60 mm Hg. As further described below, the generation of intraocular pressure before deployment of the dispensing member (conduit) may reduce scleral pliability, which in turn may facilitate the penetration of the conduit through the sclera, decrease unpleasant sensation associated with the conduit penetration through the eye wall during an injection procedure and/or prevent backlash of the device.

The drug delivery devices, components thereof, and/or various active agents may be provided in systems or kits as separately packaged components. The systems or kits may include one or more devices as well as one or more active agents. The devices may be preloaded or configured for manual drug loading. When a plurality of active agents is included, the same or different active agents may be used. The same or different doses of the active agent may be used as well. The systems or kits will generally include instructions for use. They may also include anesthetic agents and/or antiseptic agents.

BRIEF DESCRIPTION OF THE DRAWINGS

FIGS. 1A-1B depict front views of exemplary ocular contact surfaces.

FIGS. 2A-2C show side views of additional exemplary ocular contact surfaces that include measuring components.

FIGS. 3A1-3A3 and FIGS. 3B1-3B3 show side views of other exemplary ocular contact surfaces.

FIG. 4A and FIGS. 4B1-4B2 depict perspective and front views of an exemplary flanged ocular contact surface.

FIGS. 5A1-5A2 and FIGS. 5B1-5B2 depict side and perspective views of exemplary flat and convex ocular contact surfaces.

FIGS. 6A1-6A2 and FIGS. 6B1-6B2 show side and front views of exemplary soft or semi-solid ocular contact surfaces.

FIGS. 7A1-7A2, FIGS. 7B1-7B2, FIGS. 7C1-7C2, and FIGS. 7D-7E show additional exemplary ocular contact surfaces, including ocular contact surfaces having a high-traction interface.

FIGS. 9A-9C show exemplary arrangements of measuring components around an ocular contact surface.

FIGS. 10A-10C depict other exemplary measuring components and how they work to measure a certain distance from the limbus.

FIGS. 11A-11D show further exemplary measuring components.

FIGS. 15A1-15A2 show side views of exemplary bevel angles.

FIGS. 16A-16D depict cross-sectional views of exemplary conduit geometries.

FIG. 17 depicts a cross-sectional view of additional exemplary conduit geometries.

FIGS. 23A-23C depict other examples of drug loading members.

FIGS. 24A-24D show an exemplary fenestrated drug loading member.

FIG. 29 is a cross-sectional view of the device and two-spring actuation mechanism shown in FIG. 28.

FIG. 30 is a cross-sectional view of the device shown in FIG. 28 after the two-spring actuation mechanism has been activated.

FIGS. 33A-33B depict the device of FIG. 28 with an exemplary loading port.

FIGS. 35A-35B provide cross-sectional views of the device shown in FIG. 34. FIG. 35A show the pneumatic actuation mechanism in a pre-activated state. FIG. 35B shows the pneumatic actuation mechanism after deployment of the conduit.

FIGS. 39A-39I depict various views of exemplary device tips.

FIGS. 41A-41B provide cross-sectional views of another exemplary device having a two-spring actuation mechanism.

FIGS. 45A-45J show various aspects of exemplary fine sleeve mobility control components.

FIG. 49A depicts a side view of the sleeve. FIG. 49B is a cross-sectional view of the sleeve shown in FIG. 49A taken along line B-B.

DETAILED DESCRIPTION

Figure 7D:
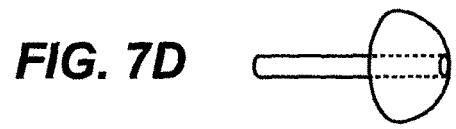

Described here are hand-held devices, methods, and systems for delivering, e.g., by injection, pharmaceutical formulations into the eye. The devices may integrate (combine) various features that may be beneficial in delivering the pharmaceutical formulations into the eye, e.g., in a safe, sterile, and accurate manner, into a single device. Thus, features that may aid appropriate placement on the eye, help positioning so that the intraocular space is accessed at the proper angle, adjust or control intraocular pressure, and/or help to minimize trauma to the sclera and intraocular structures, e.g., from the force of injection or penetration of the sclera itself, may be integrated into a single device. The devices, in whole or in part, may be configured to be disposable.

I. DEVICES

In general, the integrated devices described here include a housing sized and shaped for manipulation with one hand. The housing typically has a proximal end and a distal end, and an ocular contact surface at the housing distal end. A conduit tin its pre-deployed state may reside within the housing. The conduit will be at least partially within the housing in its deployed state. In some variations, the conduit is slidably attached to the housing. Additionally, the conduit will generally have a proximal end, a distal end, and a lumen extending therethrough. An actuation mechanism may be contained within the housing that is operably connected to the conduit and a reservoir for holding an active agent.

The devices or portions thereof may be formed from any suitable biocompatible material or combination of biocompatible materials. For example, one or more biocompatible polymers may be used to make, e.g., the device housing, ocular contact surface, measuring component, etc. Exemplary biocompatible and non-biodegradable materials include without limitation, methylmethacrylate (MMA), polymethylmethacrylate (PMMA), polyethylmethacrylate (PEM), and other acrylic-based polymers; polyolefins such as polypropylene and polyethylene; vinyl acetates; polyvinylchlorides; polyurethanes; polyvinylpyrollidones; 2-pyrrolidones; polyacrylonitrile butadiene; polycarbonates; polyamides; fluoropolymers such as polytetrafluoroethylene (e.g., TEFLON™ polymer); polystyrenes; styrene acrylonitriles; cellulose acetate; acrylonitrile butadiene styrene; polymethylpentene; polysulfones; polyesters; polyimides; natural rubber; polyisobutylene rubber; polymethylstyrene; silicone; and copolymers and blends thereof.

In some variations, the device or a portion of the device such as the drug reservoir, plunger, housing, ocular contact surface, or measuring component, is made of a material that includes a cyclic olefin series resin. Exemplary cyclic olefin resins include without limitation, commercially available products such as Zeonex® cyclo olefin polymer (ZEON Corporation, Tokyo, Japan) or Crystal Zenith® olefinic polymer (Daikyo Seiko, Ltd., Tokyo, Japan) and APEL™ cyclo olefin copolymer (COC) (Mitsui Chemicals, Inc., Tokyo, Japan), a cyclic olefin ethylene copolymer, a polyethylene terephthalate series resin, a polystyrene resin, a polybutylene terephthalate resin, and combinations thereof. In one variation, it may be beneficial to use a cyclic olefin series resin and a cyclic olefin ethylene copolymer that have high transparency, high heat resistance, and minimal to no chemical interaction with a pharmacological product such as a protein, a protein fragment, a polypeptide, or a chimeric molecule including an antibody, a receptor or a binding protein.

The cyclic olefin polymers or the hydrogenation products thereof can be ring-opened homopolymers of cyclic olefin monomers, ring-opened copolymers of cyclic olefin monomers and other monomers, addition homopolymers of cyclic olefin monomers, addition copolymers of cyclic olefin monomers and other monomers, and hydrogenation products of such homopolymers or copolymers. The above cyclic olefin monomers may include monocyclic olefin monomers, and polycyclic olefin monomers including bicyclic and higher cyclic compounds. Examples of the monocyclic olefin monomers suitable for the production of the homopolymers or copolymers of the cyclic olefin monomers are monocyclic olefin monomers such as cyclopentene, cyclopentadiene, cyclohexene, methylcyclohexene and cyclooctene; lower-alkyl derivatives thereof containing, as substituent groups, 1 to 3 lower alkyl groups such as methyl and/or ethyl groups; and acrylate derivatives thereof.

Examples of the polycyclic olefin monomers are dicyclopentadiene, 2,3-dihydrocyclopentadiene, bicyclo[2,2,1]-hepto-2-ene and derivatives thereof, tricyclo[4,3,0,1$^{2,5}$]-3-decene and derivatives thereof, tricyclo[4,4,0,1$^{2,5}$]-3-undecene and derivatives thereof, tetracyclo[4,4,0,1$^{2,5}$, 0$^{7,10}$]-3-dodecene and derivatives thereof, pentacyclo[6,5,1, 1$^{3,6}$,0$^{2,7}$,0$^{9,13}$ 4-pentadecene and derivatives thereof, pentacyclo[7,4, 0,1$^{2,5,0}$,0$^{8,13}$,1$^{9,12}$]-3-pentadecene and derivatives thereof, and hexacyclo[6,6,1,1$^{3,6}$,1$^{10,13}$,0$^{2,7}$,0$^{9,14}$]-4-heptadecene and derivatives thereof. Examples of bicyclo[2,2,1]-hepto-2-ene derivatives include 5-methyl-bicyclo[2,2,1]-hepto-2-ene, 5-methoxy-bicyclo[2,2,1]-hepto-2-ene, 5-ethylidene-bicyclo[2,2,1]-hepto-2-ene, 5-phenyl-bicyclo [2,2,1]-hepto-2-ene, and 6-methoxycarbonyl-bicyclo[2,2, 1-]-hepto-2-ene. Examples of tricyclo[4,3,0,1$^{2,5}$]-3-decene derivatives include 2-methyl-tricyclo[4,3,0,1$^{2,5}$]-3-decene and 5-methyl-tricyclo[4,3,0,1$^{2,5}$]-3-decene. Examples of tetracyclo[4,4,0,1$^{2,5}$]-3-undecene derivatives include 10-methyl-tetracyclo[4,4,0,1$^{2,5}$]-3-undecene, and examples of tricyclo[4,3,0,1$^{2,5}$]-3-decene derivatives include 5-methyl-tricyclo[4,3,0,1$^{2,5}$]-3-decene.

Examples of tetracyclo[4,4,0,1$^{2,5}$,0$^{7,10}$]-3-dodecene derivatives include 8-ethylidene-tetracyclo-[4,4,0,1$^{2,5}$, 0$^{7,10}$]-3-dodecene, 8-methyl-tetracyclo-[4,4,0,1$^{2,5}$,0$^{7,10}$]-3-dodecene, 9-methyl-8-methoxy-carbonyl-tetracyclo[4,4,0, 1$^{2,5}$,0$^{7,10}$]-3-dodecene, 5,10-dimethyl-tetracyclo[4,4,0,1$^{2,5}$, 0$^{7,10}$]-3-dodecene. Examples of hexacyclo[6,6,1,1$^{3,6}$,1$^{10,13}$, 0$^{2,7}$,0$^{9,14}$]-4-heptadecene derivatives include 12-methyl-hexacyclo[6,6,1,1$^{3,6}$,0$^{10,13}$,0$^{2,7}$,0$^{9,14}$]-4-heptadecene and 1,6-dimethyl-hexacyclo[6,6,1,1$^{3,6}$,1$^{10,13}$,0$^{2,7}$,0$^{9,14}$]-4-heptadecene. One example of the cyclic olefin polymer is an addition homopolymer of at least one cyclic olefin monomer or an addition copolymer of at least one cyclic olefin monomer and at least one other olefin monomer (for example, ethylene, propylene, 4-methylpentene-1, cyclopentene, cyclooctene, butadiene, isoprene, styrene, or the like). This homopolymer or copolymer can be obtained by polymerizing the above monomer or monomers, for example, while using as a catalyst a known catalyst which is soluble in a hydrocarbon solvent and is composed of a vanadium compound or the like and an organoaluminum compound or the like (Japanese Patent Application Laid-Open (Kokai) No. HEI 6-157672, Japanese Patent Application Laid-Open (Kokai) No. HEI 5-43663).

Another example of the cyclic olefin polymer is a ring-opened homopolymer of the above monomer or a ring-opened copolymer of the above monomers. It can be obtained by homopolymerizing the above monomer or copolymerizing the above monomers, for example, while using as a catalyst a known catalyst such as (1) a catalyst composed of a halide or the nitrate of a platinum group metal such as ruthenium, rhodium, palladium, osmium or platinum and a reducing agent or (2) a catalyst composed of a compound of a transition metal such as titanium, molybdenum or tungsten and an organometal compound of a metal in one of Groups I to IV of the periodic table such as an organoaluminum compound or organotin compound (Japanese Patent Application Laid-Open (Kokai) No. HEI 6-157672, Japanese Patent Application Laid-Open (Kokai) No. HEI 5-43663).

The homopolymer or copolymer may contain unsaturated bonds. The homopolymer or copolymer may be hydrogenated using a known hydrogenation catalyst. Examples of the hydrogenation catalyst include (1) Ziegler-type homogeneous catalysts which are each composed of an organic acid salt of titanium, cobalt, nickel or the like and an organometal compound of lithium, aluminum or the like, (2) supported catalysts which are each composed of a carrier such as carbon or alumina and a platinum metal such as palladium or ruthenium supported on the carrier, and (3) catalysts which are each composed of a complex of one of the above-described platinum group metal (Japanese Patent Application Laid-Open (Kokai) No. HEI 6-157672).

In some variations, the device or a portion of the device such as the drug reservoir is made of a material that comprises a rubber. Examples of suitable rubber materials include butyl rubbers such as butyl rubber, chlorinated butyl rubber, brominated butyl rubber, and divinylbenzene-copolymerized butyl rubber; conjugated diene rubbers such as polyisoprene rubber (high to low cis-1,4 bond), polybutadiene rubber (high to low cis-1,4 bond), and styrene-butadiene copolymer rubber; and ethylene-propylene-diene terpolymer rubber (EPDM). Crosslinkable rubber materials may also be used, and may be made by kneading the above-described rubber materials together with additives such as a crosslinking agent, a filler and/or reinforcement, a colorant, or an age resister.

In some variations, the biocompatible material is a biodegradable polymer. Non-limiting examples of suitable biodegradable polymers include cellulose and ester, polyacrylates (L-tyrosine-derived or free acid), poly($\beta$-hydroxyesters), polyamides, poly(amino acid), polyalkanotes, polyalkylene alkylates, polyalkylene oxylates, polyalkylene succinates, polyanhydrides, polyanhydride esters, polyaspartimic acid, polylactic acid, polybutylene digloclate, poly(caprolactone), poly(caprolactone)/poly(ethylene glycol) copolymers, polycarbone, L-tyrosin-derived polycarbonates, polycyanoacrylates, polydihydropyrans, poly(dioxanone), poly-p-dioxanone, poly($\epsilon$-caprolactone-dimethyltrimethylene carbonate), poly(esteramide), polyesters, aliphatic polyesters, poly(etherester), polyethylene glycol/poly(orthoester) copolymers, poly(glutarunic acid), poly(glycolic acid), poly(glycolide), poly(glycolide)/poly(ethylene glycol) copolymers, poly(lactide), poly(lactide-co-caprolactone), poly(DL-lactide-co-glycolide), poly(lactide-co-glycolide)/poly(ethylene glycol) copolymers, poly(lactide)poly(ethylene glycol) copolymers, polyphosphazenes, polyphosphesters, polyphophoester urethanes, poly(propylene fumarate-co-ethylene glycol), poly(trimethylene carbone), polytyrosine carbonate, polyurethane, terpolymer (copolymers of glycolide lactide or dimethyltrimethylene carbonate), and combinations, mixtures or copolymers thereof.

Additives may be added to polymers and polymer blends to adjust their properties as desired. For example, a biocompatible plasticizer may be added to a polymer formulation used in at least a portion of a device to increase its flexibility and/or mechanical strength, or to provide color contrast with respect to the surface of the eye. In other instances, a biocompatible filler such as a particulate filler, fiber and/or mesh may be added to impart mechanical strength and or rigidity to a portion of a device.

The devices described here can be manufactured, at least in part, by injection or compression molding the above-described materials.

In some instances, it may be beneficial to include a removably attached or integrated viewing and/or magnifying element on the device. For example, a magnifying glass and/or illumination source such as a LED light may be removably attached to the device to facilitate the visualization of the tip of the device and the injection site. The improved visualization may help to more precisely and safely position the device at a target location, e.g., about 3.5 mm to 4 mm posterior to the corneo-scleral limbus, so that complications of intraocular injection such as retinal detachment, ciliary body bleeding, or trauma to the intraocular lens can be potentially avoided. The magnifying glass may be made from any suitable material, e.g., it may be made from any suitable non-resorbable (biodegradable) material previously described, but will typically be light-weight so that it does not affect the balance of the injection device. The magnifying glass and/or illumination source, e.g., the LED, may be disposable.

Housing

The housing of the device generally contains the drug reservoir and actuation mechanism. In its first, non-deployed state (pre-deployed state), the conduit may reside within the housing. The housing may be of any suitable shape, so long as it allows grasping and manipulation of the housing with one hand. For example, the housing may be tubular or cylindrical, rectangular, square, circular, or ovoid in shape. In some variations, the housing is tubular or cylindrical, similar to the barrel of a syringe. In this instance, the housing has a length between about 1 cm and about 15 cm, between about 2.5 cm and about 10 cm, or about 4 cm and about 7.5 cm. For example, the housing may have a length of about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, or about 15 cm. The surface of the housing may also be texturized, roughened, or otherwise modified in certain areas, e.g., with protrusions, ridges, etc., to aid the grip and or manipulation of the housing by the user. Grips may be associated with any one of the actuation mechanisms further described below. The grips are generally configured to help the operator maintain a steady grip on the device using, e.g., two, three or four fingers. The plunger actuation lever may be located on the device housing in the close proximity of the grip, for example, integrated with the grip, or between about 1.0 mm and 10 mm of the grip, so that the operator is able to easily use the fingers holding the device to actuate, e.g., slide, the actuation lever while maintaining a steady grip and without compromising the hold/control of the device. The distance that the actuation lever may travel may be between about 2.0 mm and about 8.0 mm, or between about 1.0 mm and about 15 mm). Maintaining a steady grip while actuating the drug injection mechanism is useful because it helps to localize the injection site on the eye surface with about a 0.5 mm precision accuracy The housing may be made from any suitable material. For example, and as previously stated, the components of the device may be made from any suitable biocompatible material or combination of biocompatible materials. Materials that may be beneficial in making the housing include, without limitation, a cyclic olefin series resin, a cyclic olefin ethylene copolymer, a polyethylene terephthalate series resin, a polystyrene resin, and a polyethylene terephthalate resin. In one variation, it may be beneficial to use a cyclic olefin series resin and a cyclic olefin ethylene copolymer that have a high transparency, a high heat resistance, and minimal to no chemical interaction with a pharmacological product such as a protein, a protein fragment, a polypeptide, or a chimeric molecule including an antibody, a receptor or a binding protein. Additional materials that may be beneficial in making the housing include, without limitation, fluoropolymers; thermoplastics such as polyetheretherketone, polyethylene, polyethylene terephthalate, polyurethane, nylon, and the like; and silicone. In some variations, the housing may be made from a transparent material to aid confirmation of conduit deployment and/or drug delivery. Materials with suitable transparency are typically polymers such as acrylic copolymers, acrylonitrile butadiene styrene (ABS), polycarbonate, polystyrene, polyvinyl chloride (PVC), polyethylene terephthalate glycol (PETG), and styrene acrylonitrile (SAN). Acrylic copolymers that may be useful include, but are not limited to, polymethyl methacrylate (PMMA) copolymer and styrene methyl methacrylate (SMMA) copolymer (e.g., Zylar 631® acrylic copolymer).

Ocular Contact Surfaces

The devices described herein generally include an atraumatic ocular contact surface at the distal end of the housing. In some variations, the ocular contact surface is fixedly attached to the housing proximal end. In other variations, the ocular contact surface is removably attached to the housing proximal end. The ocular contact surface will typically be sterile. In some instances, the ocular contact surface is disposable. In use, the ocular contact surface of the device is placed on the surface of the eye.

The ocular contact surface may be of any suitable configuration, e.g., size, shape, geometry, etc., as long as it allows atraumatic placement of the device on the ocular surface. In some variations, the ocular contact surface is ring-shaped (e.g., FIGS. 1A-1B). When the ocular contact surface takes the shape of a ring, it may have a diameter of about 0.3 mm to about 8 mm, about 1 mm to about 6 mm, or about 2 mm to about 4 mm. In other variations, the ocular contact surface is oval or circular in shape.

More specifically, as shown in the front views of FIGS. 1A-1B, the device tip comprises a ring-shaped ocular contact surface where the distance between the inner diameter and outer diameter of the ring forms a rim. In this instance, the ring-shaped ocular contact surface may be configured as having a wider ocular contact surface (10) (rim) and smaller internal opening (12) (FIG. 1A), or narrower ocular contact surface (14) (rim) with larger internal opening (16) (FIG. 1B). The dispensing member (conduit) may be an injection needle that is hidden inside and protected by the device tip. A membrane may also be provided that extends across the internal opening, and which may be flush with the ocular contact surface or recessed within the lumen of the device tip where the injection needle resides.

As shown in FIGS. 39A-39B, the tip of the dispensing member may be recessed relative to end of the device housing tip comprising the ocular contact surface in the resting state, so that when the device tip is placed in contact with any surface such as the skin or the eye wall, the tip of the dispensing member is separated from the surface by a distance marked with arrows in FIG. 39B. This distance may ensure that the dispensing member tip does not come in direct contact with any surface prior to the injection procedure, which prevents accidental bacterial contamination of the dispensing member from sources such as skin secretions, ocular secretions or tears, and minimizes the risk of introducing intraocular infectious agents during the intraocular injection procedure that may cause endophthalmitis.

In some variations, the tip of the dispensing member is recessed relative to, and is separated from the closest end of the device housing by a distance ranging from about 0.01 mm to about 10 mm, from about 0.1 mm to about 5 mm, or from about 0.5 mm to about 2 mm.

An enclosure may be provided on the distal end of the device that completely covers the dispensing member to prevent it from contacting eye lashes or eye lids, and to prevent it from being exposed to potentially contaminated surfaces at all times. Here the dispensing member may extend from the enclosure and penetrate the eye wall and into an eye cavity without being exposed to ocular appendages such as eyelids or eye lashes that harbor bacteria. The eye is an immune-privileged organ and, thus, any bacterial contamination has the propensity to result in intraocular infection. Enclosure of the dispensing member may protect it from contacting ocular appendages harboring bacteria, thereby minimizing the risk of sight-threatening intraocular infection. In one variation, the dynamic sleeve (further described below) is configured as the sterile enclosure. The dynamic sleeve may also be covered by a membrane that prevents ocular surface tears from entering the orifice of the device tip and potentially contaminating the dispensing member before it is deployed.

In other variations, the outer surface of the device tip may be configured to include a raised surface that forms a seal around the exit site of the dispensing member from the device tip. The seal may function to prevent ocular tears from circulating through the potential injection site once the device tip has been positioned on the eye surface. The raised surface may be configured to be annular, oval, square, rectangular, triangular or any other suitable shape or geometry.

In another variation, the ocular contact surface of the device tip that comes in direct contact with the eye surface is ring-shaped, where there is a clearing between the internal wall of the device housing and the dispensing member of about 360 degrees, which is marked by arrows in FIG. 39C. Here, if the ring-shaped ocular interface surface becomes contaminated with an infectious agent and is placed onto the eye surface, the dispensing member will come in contact and penetrate through the eye surface that is separated from the contaminated device tip by the area of clearing, which prevents accidental bacterial contamination of the dispensing member and minimizes the risk of introducing intraocular infection that may cause endophthalmitis. In contrast, the lack of such clearing around the dispensing member, as shown in FIG. 39D, may allow accidental infectious contamination of the device tip at the site of injection.

In some variations, there is a clearing between the internal wall of the device housing and the dispensing member ranging from about 0.1 mm to about 5 mm, from about 0.3 mm to 3 mm, or from about 0.5 mm to about 2 mm.

In other variations, there is a solid membrane or partition (105) that separates the tip of the dispensing member (107) from the external environment, as shown in FIG. 39E, where the membrane or partition may be water-impermeable and/or be air-impermeable. The membrane or partition may ensure that there is no air movement in or out of the device creating an air seal and maintaining a certain constant air pressure inside the device.

Furthermore, the membrane or partition may ensure that the dispensing member tip does not come in contact with any source of accidental bacterial contamination such as tears and ocular secretions prior to the injection procedure, which prevents accidental bacterial contamination of the dispensing member and minimizes the risk of introducing intraocular infection during the intraocular injection procedure that may cause endophthalmitis.

The membrane or partition that separates the tip of the dispensing member from the end of the device housing may comprise a material selected from the group consisting of biocompatible and non-biodegradable materials including without limitation, methylmethacrylate (MMA), polymethylmethacrylate (PMMA), polyethylmethacrylate (PEM), and other acrylic-based polymers; polyolefins such as polypropylene and polyethylene; vinyl acetates; polyvinylchlorides; polyurethanes; polyvinylpyrollidones; 2-pyrrolidones; polyacrylonitrile butadiene; polycarbonates; polyamides; fluoropolymers such as polytetrafluoroethylene (e.g., TEFLON™ polymer); or fluorinated ethylene propylene (FEP); polystyrenes; styrene acrylonitriles; cellulose acetate; acrylonitrile butadiene styrene; polymethylpentene; polysulfones; polyesters; polyimides; natural rubber; polyisobutylene rubber; polymethylstyrene; silicone; derivatives and copolymers and blends thereof.

In some variations, the membrane or partition (30) may be recessed inside the device tip so that when the device tip is placed in contact with any surface such as the skin or the eye surface, the said membrane or partition is separated from the said surface by a distance marked with arrows, as depicted in FIG. 39E. The distance may ensure that the dispensing member tip (31) does not come in direct contact with any surface prior to the injection procedure, which prevents accidental bacterial contamination of the dispensing member from sources such as skin secretions, ocular secretions or tears, and minimizes the risk of introducing intraocular infection during the intraocular injection procedure that may cause endophthalmitis.

The membrane or partition may be recessed relative to and separated from the end of the device housing at the ocular interface by a distance ranging from about 0.01 mm to about 10 mm, from about 0.1 mm to about 5 mm, or from about 0.5 mm to about 2 mm.

In further variations, a measuring component (32) (further described below) may be recessed relative to the end of the device housing (33) at the ocular contact surface (FIGS. 39F-39H), so that when the device tip (34) comes in contact with the eye surface (35) (FIG. 39I), the measuring component (32) does not come in contact with the eye surface (35). This configuration may minimize the risk of trauma to the delicate tissue covering the eye surface such as the non-keratinizing epithelia of the cornea and conjunctiva. Avoiding direct contact between the measuring member and the ocular surface may be beneficial in minimizing the risk of ocular surface trauma such as corneal or conjunctival abrasion, which prevents further serious complications such as bacterial injection including corneal ulcer. In alternative variations, the tip of the measuring member (32) may be angled away or towards the eye (FIGS. 39G and 39H, respectively). The measuring component may be recessed relative to the end of the device housing by a distance ranging from about 0.01 mm to about 5 mm, from about 0.1 mm to about 3 mm, or from about 0.5 mm to about 2 mm.

In some variations, as shown in FIGS. 2A-2C, the device tip may also comprise a ring-shaped ocular contact surface and a measuring means that helps to determine the proper location of the injection site at a certain distance relative to and perpendicular to the corneo-scleral limbus. In one variation, the measuring component (20) is located on one side of the device tip (22). In another variation, more than one measuring component is located on more than one side of the device tip. Here the tip of the measuring component is flat (FIG. 2C) and does not substantially protrude above the ocular contact surface. In other variations, the tip of the measuring component is raised (FIGS. 2A-2B) above the ocular contact surface, which enables it to prevent the eyelid from sliding over and on top of the measuring component, thus preventing the eyelid from coming into contact with the sterile ocular contact surface of the device tip or the dispensing member. This in turn may reduce the risk of accidental contamination and intraocular infection during the injection procedure.

In other variations, the ocular contact surface comprises a flange (e.g., FIGS. 3A1-3A3, FIGS. 3B1-3B3, FIG. 4A, and FIGS. 4B1-4B2). The flange may provide an expanded contact surface between the device tip and the eye surface, thus increasing the stability of the device when it is positioned on the ocular surface, and decreasing the pressure force per unit area of the device-ocular interface. Reducing the pressure force per unit area of the device-ocular interface in turn may reduce the potential for conjunctival damage by the device tip when it is pressed against the eye wall. Avoiding such conjunctival damage is desirable because the conjunctiva is covered by delicate non-keratinizing epithelium containing multiple sensory nerve endings and pain receptors.

In some variations, the flange may have thin edges that come in contact with the ocular surface, and which allows the eye lid to travel over and on top of the flange, but prevents the eye lid from coming in contact with the sterile ocular contact surface of the device tip. The ocular contact surface may also be a ring-shaped flange (e.g., FIGS. 4A and 4B1-4B2). Such a ring-shaped flange may also prevent the eye lid from coming in contact with the sterile ocular contact surface of the device tip.

More specifically, as shown in FIG. 3, the flange may have a thin edge (FIG. 3A1), which allows the eye lid to slide over the said flange and come in contact with the shaft of the device tip. In an alternative variation, the said flange may be thick (FIG. 3B1) in order to prevent the eye lid from sliding over it and keeping it from coming in contact with the device shaft, thus preventing inadvertent contamination of the injection site. When the flange at the ocular contact surface of the device tip is thick, its edges, such as those at its ocular surface may be rounded in order to prevent accidental damage to the ocular surface tissues such as the conjunctiva that is covered with delicate non-keratinizing epithelium rich in nerve endings and pain receptors. In alternative variations of the device tip, the ocular contact interface may be flat (FIGS. 3A1 and 3B1), convex (FIGS. 3A2 and 3B2), or concave (FIGS. 3A3 and 3B3) to reduce the chance of accidental damage to ocular surface tissues such as the conjunctiva while providing a means of applying a force onto the eye wall and increasing intraocular pressure in order to facilitate the needle penetration through the eye wall, as well as to partially immobilize the eye during the injection procedure by providing the traction interface of the ocular contact surface. FIGS. 4A and 4B1-4B2 illustrate perspective and front views of a flanged ocular contact surface.

In yet further variations, the ocular contact surface may be configured to be flat, convex, concave, or slanted (e.g., FIGS. 5 and 7). In FIGS. 5A1-5A2, the device tip has a flat ocular contact surface. In an alternative variation, the device tip has a protruding or convex ocular contact surface (FIGS. 5B1-5B2), which may improve contact between the internal opening of the device tip and the ocular surface when the device tip is pressed against the eye wall resulting in eye wall indentation. In yet another variation, the ocular contact surface of the device tip is indented or concave, which reduces the risk of accidental damage to the ocular surface tissue such as the conjunctiva. Such configurations of the ocular contact surface of the device tip may reduce the chance of accidental damage to ocular surface tissues, such as the conjunctiva, while providing a means of applying a pressure force onto the eye wall and increasing the intraocular pressure in order to facilitate the needle penetration through the eye wall, as well as to partially immobilize the eye during the injection procedure by providing the device-ocular surface traction interface.

More specifically, as shown in FIG. 7, the ocular contact surface may be flat and perpendicular to the long axis of the said device (FIGS. 7A1-7A2), or is flat and slanted relative to the long axis of the said device (7B1-7B2) (e.g., oriented at an angle other than 90 degrees, such as from about 45 degrees to about 89 degrees relative to the long axis of the device), or is convex and perpendicular to the long axis of the device (FIG. 7C1), or is convex and slanted relative to the long axis of the device (FIG. 7C2), or is rounded (FIG.

Figure 7E:

7D), or is oval (FIG. 7E). In one variation, the ocular interface is rounded or oval (e.g., similar to the tip of a Q-tip). The thickness of the ocular contact surface may be from about 0.01 mm to about 10 mm, from about 0.05 mm to about 5 mm, or from about 0.1 mm to about 2 mm.

The ocular contact surface may include one or more features that help to stabilize it on the eye surface. For example, in one variation, the ocular contact surface comprises a plurality of traction elements, e.g., bumps, ridges, raised details above the plane of the ocular contact surface, etc., that increase surface traction of the ocular contact surface on the eye surface without being abrasive. Such an ocular contact surface may provide a medium- or high-traction interface to stabilize the device on the surface of the eye and prevent it from moving during intraocular drug delivery. In another variation, the ocular contact surface includes an adherent interface such as a suction mechanism. Varying the type of material used to make the ocular contact surface may also help prevent its slippage on the ocular surface.

The materials used to make the ocular contact surface may also help to prevent abrasion, scratching, or irritation of the eye surface. Exemplary non-abrasive materials that may be employed include without limitation, nylon fiber, cotton fiber, hydrogels, spongiform materials, styrofoam materials, other foam-like materials, silicone, plastics, PMMA, polypropylene, polyethylene, fluorinated ethylene propylene (FEP), and polytetrafluoroethylene (PTFE). These materials may be smooth-hard, semi-hard, or soft, and may be beneficial in preventing conjunctival abrasion, subconjunctival hemorrhage during transcleral needle deployment, or other accidental trauma to the ocular surface tissues (FIG. 6). Materials typically used in contact lens manufacturing may also be employed.

In some variations, the edges of the ocular contact surface are also rounded to prevent accidental damage to the ocular surface tissues such as the conjunctiva that is covered with delicate non-keratinizing epithelium rich in nerve endings and pain receptors. In this instance, as shown in FIG. 6, the ocular contact surface may have a circumference corresponding to the circumference of the device tip (FIGS. 6A1-6A2). In other variations, the circumference of the ocular contact surface may protrude beyond the circumference of the shaft of the device tip, thus forming a flange (FIGS. 6B1-6B2). The flange may increase the ocular contact surface of the device tip while maintaining the slim profile of the shaft of the tip, enabling its easy insertion into the interpalpebral fissure of the eye.

The ocular contact surface may also provide an interface surface that is pliable or deformable, and which conforms to the surface of the eye when placed against the said eye surface during the intraocular drug delivery procedure. The surface of the eye that comes in direct contact with the said interface surface of the disclosed device includes, but is not limited to, the surface of the eye over the pars plana region defined as the circumferential area between about 2 mm and 7 mm posterior to and surrounding the limbus, or the corneo-scleral limbal area between about 2 mm anterior and about 2 mm poster to and circumferential to the limbus. The interface surface that conforms to the curvature of the surface of the eye may enable the formation of an optimal contact interface between the device and the eye, and may ensure sterility of the intraocular drug delivery process and immobilization of the eye, which in turn may enhance the safety of the injection procedure. Examples of ocular interface materials for the device are those that are generally able to conform to the surface of the eye (that is deformable or pliable) particularly to the curvature of the external surface of the eye in the area of pars plana about 2-5 mm posterior to the corneo-scleral limbus for intravitreal drug application, as well as to the area of the corneo-scleral limbus for anterior chamber drug applications. As previously stated, materials that are non-abrasive to the non-keratinizing conjunctival and corneal epithelium of the ocular surface may be used. Specifically, the materials and their configurations (e.g., foam, braid, knit, weave, fiber bundle, etc.), may include those capable of forming medium- or high-traction surfaces (e.g., hydrogels or cotton) that enable immobilization of the eye globe during the injection procedure.

In some variations, the material of the ocular contact surface changes its properties upon contact with fluid, e.g., by reducing its traction coefficient such as in cotton fiber, which may reduce the risk of conjunctival abrasion upon contact of the ocular contact surface with the eye surface. In other variations, the material comprising ocular contact surface does not change its physical and chemical properties when exposed to fluid that covers the surface of the eye such as tears.

The ocular contact surfaces described here may be beneficial in preventing conjunctival and/or episcleral bleeding during intraocular needle injection. For example, a device comprising a ring-shaped ocular interface may be pressed against the eye wall, which in turn applies pressure to the conjunctival and episcleral vessels, thereby reducing blood flow therethrough. Given the reduced blood flow through these vessels, the risk of subconjunctival bleeding during intraocular injection procedure may be reduced. Following the completion of intraocular drug application, the needle is withdrawn, but the ring-shaped tip may remain pressed against the eye wall, thus applying continuous pressure onto the conjunctival and episcleral vessels and further reducing the risk of bleeding and/or minimizing the extent of bleeding.

In some variations, the device comprises an ocular contact surface that functions as a drug reservoir. Here a drug may be incorporated into, or coated on, the material of the ocular contact surface. The drug may then diffuse, leech, etc., from the ocular contact surface onto the surface of the eye. Exemplary materials for inclusion of drugs are hydrogels and their derivatives.

The ocular contact surface may also cover the dispensing member (conduit) such as an injection needle (e.g., it may be a cap that entirely covers the needle), which may enable the injector to apply pressure onto the eye by pressing the tip (e.g., the distal end of the cap) against the eye wall. This in turn may increase the intraocular pressure before the needle comes in contact with the eye wall and, thus, may facilitate needle penetration because the eye wall is more taut in comparison to an eye wall being penetrated by a needle on a conventional syringe. Needle penetration is typically more difficult with a conventional syringe because the lower intraocular pressure that is generated makes the eye wall more deformable and mobile. In addition, the device tip that covers the dispensing member (conduit), such as an injection needle, may also protect the said dispensing member from being contaminated by its accidental contact with eye lids.

Intraocular Pressure Control Mechanisms (Ocular Wall Tension Control Mechanisms)

The control of intraocular pressure (IOP) during the drug delivery procedure, e.g., intraocular injection or intravitreal injection, may be beneficial. The application of limited intraocular pressure before deployment of the dispensing member (conduit) may reduce scleral pliability, which in turn may decrease any unpleasant sensation on the eye surface during an injection procedure and/or prevent backlash of the device. The term "backlash" typically refers to the inability of the conduit to smoothly penetrate the eye wall due to scleral pliability and elasticity, which makes the sclera indent to a certain point and push the conduit and device backwards before the conduit penetrates into and through the sclera. Accordingly, the devices described here may include one or more IOP control mechanisms, also referred to herein as ocular wall tension control mechanisms. This is because ocular wall tension is proportionally related to, and determined in part, by intraocular pressure. Other factors that may effect wall tension are scleral thickness and rigidity, which can be variable due to patient age, gender, and individual variations.

The IOP mechanisms may control IOP during the placement and positioning of the device tip at the target location on the ocular surface, and/or intraocular or intravitreal positioning of the dispensing member (conduit) during intraocular or intravitreal injection of a drug. For example, the IOP mechanisms may control IOP prior to and during the intraocular or intravitreal positioning of a dispensing member being used for trans-scleral or trans-corneal penetration. Once penetration of the ocular surface by the dispensing member occurs, IOP will typically decrease. This decrease in IOP may occur immediately after penetration of the ocular surface by the dispensing member.

In some variations, the IOP control mechanisms allow (enable) the devices to generate an IOP between 15 and 120 mm Hg during the placement and positioning of the device tip at a target location on the ocular surface, and/or intraocular positioning of the dispensing member. In other variations, the IOP control mechanisms allow (enable) the devices to generate an IOP between 20 and 90 mm Hg during the placement and positioning of the device tip at a target location on the ocular surface, and/or intraocular positioning of the dispensing member. In yet further variations, the IOP control mechanisms allow (enable) the devices to generate an IOP between 25 and 60 mm Hg during the placement and positioning of the device tip at a target location on the ocular surface, and/or intraocular positioning of the dispensing member.

The IOP control mechanisms may also allow (enable) the devices to maintain the IOP between 10 and 120 mm Hg, or between 15 and 90 mm Hg, or between 20 and 60 mmHg during any duration of time of the intraocular injection procedure. In some variations, the drug injection rate is slowed or completely aborted by the device if the intraocular pressure exceeds a certain predetermined value, for example 120 mm Hg, or 60 mm Hg, or 40 mm Hg. Here the IOP control mechanism may be configured to detect a IOP level during the intraocular drug injection of, e.g., 90 mmHg, or 60 mm Hg, or 40 mm Hg.

The IOP control mechanism may include a spring, or it may comprise a mechanical or an electrical control mechanism. In general, the IOP control mechanism will be configured to balance the frictional forces of the injection plunger and fluid injection resistance pressure (force required to push fluid through the needle into the pressurized eye fluids). The IOP control mechanisms may be coupled to the device housing and actuation mechanism in a manner that allows automatic adjustment of the force of dispensing member deployment and plunger advancement. That is, the IOP control mechanism may be configured to effect a predetermined level of force of the dispensing member and a predetermined intraocular pressure level. Again, use of the IOP control mechanisms may generate higher than the resting IOP prior to dispensing member deployment so that scleral elasticity and the potential for device backlash is decreased, and to facilitate scleral penetration by the dispensing member.

Figure 40:
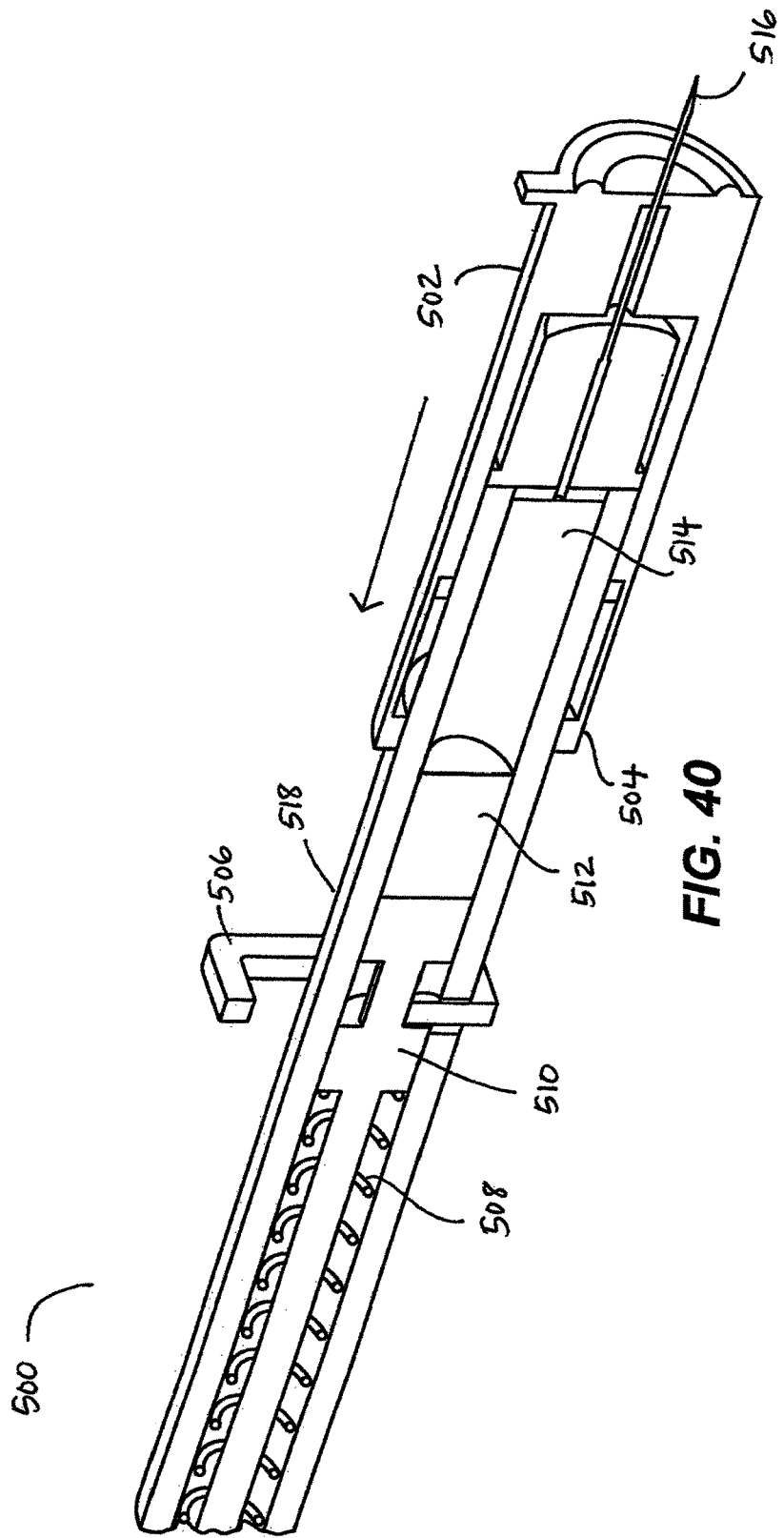
FIG. 40 shows an exemplary device with a sliding cap.

In one variation, the IOP control mechanism is a pressure relief valve that bypasses the injection stream once a maximum pressure is reached. In another variation, the IOP mechanism is a pressure accumulator that dampens the IOP within a specified range. Some variations of the IOP control mechanism may include a pressure sensor. In yet another variation, the IOP control mechanism includes a slidable cap that covers the dispensing member prior to its deployment, but which may slide or retract along the surface of the device housing to expose, deploy, or advance the dispensing member e.g., upon attainment of a predetermined IOP level. Sliding of the cap may be manually adjustable, e.g., using a dial, or automatically adjustable, step-wise, or incremental in nature. For example, as shown in FIG. 40, integrated injection device (500) includes, among other elements, a cap (502), a stop (504), a trigger (506), a spring (508), a plunger (510), a seal (512), a drug reservoir (514), a needle (516), and a syringe (518). In use, when cap (502) is placed against the ocular surface and pressure applied against the ocular surface, cap (502) slidably retracts proximally (in the direction of the arrow) to stop (504) as the syringe (518) and needle (516) are advanced. The trigger (506), e.g., a lever, may then be depressed to release spring (508), which advances plunger (510) and seal (512) to inject drug from the drug reservoir (514) through needle (516). Once the drug is injected, cap (502) slides back over the needle (516).

A locking mechanism may also be used to prevent sliding of the cap, cover or ocular contact surface, or prevent deployment of the dispensing member until a predetermined IOP is reached. The locking mechanism may also be used to prevent sliding of the cap, cover, or ocular contact surface if a predetermined IOP is not reached. For instance, the locking mechanisms included on the devices described here that include a slidable cover, cap, etc., may be released manually or automatically when the IOP reaches a predetermined level, such as between 20 mm Hg and 80 mm Hg. Such locking mechanisms may include without limitation, high traction surfaces, locking pins, interlocking raised ridges, or any other type of locking mechanism that prevents the tip of the device, e.g., the cap or cover of the device, from sliding and thus exposing the needle.

In yet further variations, the IOP control mechanism includes a high-traction surface or raised ridges on the cap, cover, or ocular contact surface situated over the dispensing member. Such features may be disposed on the inner surface of the cap, cover, or ocular contact surface and configured so that upon sliding in the proximal direction, the high-traction surface or raised ridges mate with corresponding structures (e.g., crimps, dimples, protrusions, other raised ridges) on the surface of the device housing or other appropriate device component to provide resistance of the cap, cover, or ocular contact surface against the eye wall (thus increasing ocular wall tension and IOP). In this instance, the IOP control mechanism comprises a dynamic resistance component, as further described below. As stated above, the cap, cover, or ocular contact surface may be configured so that sliding is manually or automatically adjustable, step-wise, or incremental in nature. When raised ridges are employed, any suitable number may be used, and they may be of any suitable size, shape, and geometry. For example, the raised ridges may be circumferentially disposed within the cap, cover, or ocular contact surface. In some instances, the raised ridges are configured with surfaces of differing slope.

For example, the distal surface may be configured to be steeper than the proximal surface. With this design, incremental sliding and incremental increases in IOP may be generated when the cap, cover, or ocular contact surface is slid proximally, but sliding of the cap, cover, or ocular contact surface back over the dispensing member may also be accomplished due to the decreased slope of the proximal ridge surface.

Dynamic Resistance Component

The application of pressure to the surface of the eye may be accomplished and further refined by including a dynamic resistance component to the injection device. The dynamic resistance component may be configured to detach from the injection device. The dynamic resistance component may include a slidable element and/or a fully rotatable (e.g., rotate 360 degrees) or partially rotatable (e.g., rotate less than 360 degrees) element coupled to the housing. The dynamic resistance component may be configured so that it can be fully or partially rotated about the long axis of the device using only one finger (e.g., the middle finger) while holding the device with the thumb and the index finger of the same hand. In some variations, the slidable element comprises a dynamic sleeve configured to adjust the amount of pressure applied to the eye surface, as further described below. As previously stated, certain variations of the ocular wall tension control mechanism function as dynamic resistance components.

The dynamic resistance component may also be configured as a dynamic sleeve. Similar to the slidable cap previously described, the dynamic sleeve may be configured to increase intraocular pressure and tension of the eye wall prior to needle injection. However, the dynamic sleeve is capable of being manually manipulated to thereby adjust the amount of pressure applied on surface of the eye (and thus, the amount of eye wall tension). Having the ability to manually adjust the applied pressure may allow the injector (user) to have improved control of the injection site placement and the injection angle, and also enhances the user's ability to stably position the device on the ocular surface prior to needle deployment. In general, the dynamic sleeve is designed to enable the user to precisely position the device tip at the targeted site on the eye surface and to firmly press the device tip against the eye wall to increase wall tension and intraocular pressure. The dynamic sleeve may be used to raise intraocular pressure to a predetermined level, as described above, prior to the initiation of sleeve movement and needle deployment. It should be understood that the terms "dynamic sleeve," "sleeve," "dynamic sleeve resistance control mechanism," and "sleeve resistance mechanism" are used interchangeably throughout. The dynamic sleeve will generally be configured such that when the user exerts a pulling force (e.g., retraction) on the sleeve, this movement may facilitate needle exposure and reduce the amount of pressure force (down to 0 Newton) ("N" refers to the unit of force "Newton") needed to be applied to the eye wall in order to slide the sleeve back and expose the needle. The dynamic sleeve may also be configured such that when the user exerts a pushing force (e.g., advancement) on the sleeve, this movement may counteract and impede needle exposure, which may allow the device tip to apply increased pressure to the eye wall prior to the initiation of sleeve movement and needle exposure.

Figure 42:
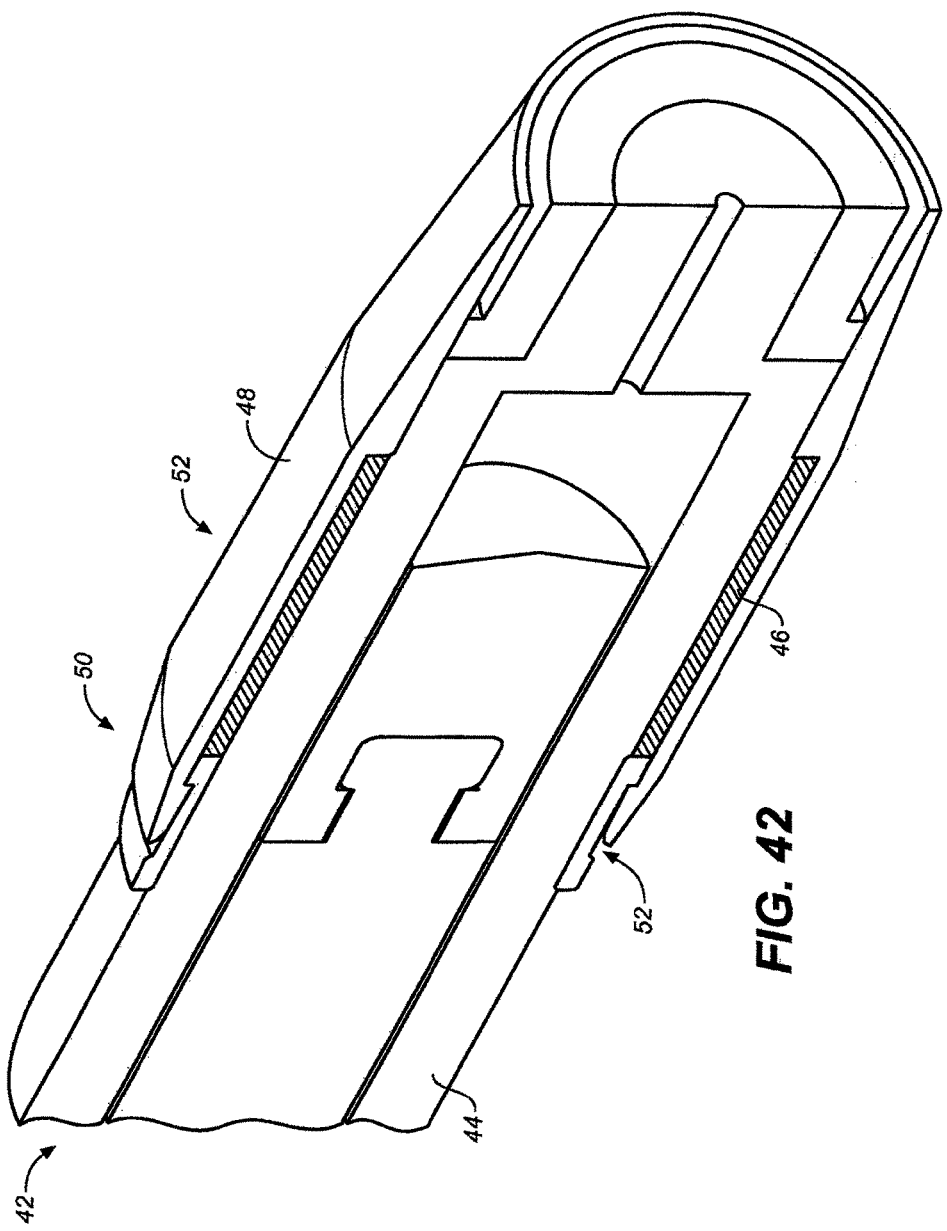
FIG. 42 depicts an enlarged sectional view an exemplary dynamic sleeve.
Figure 46:
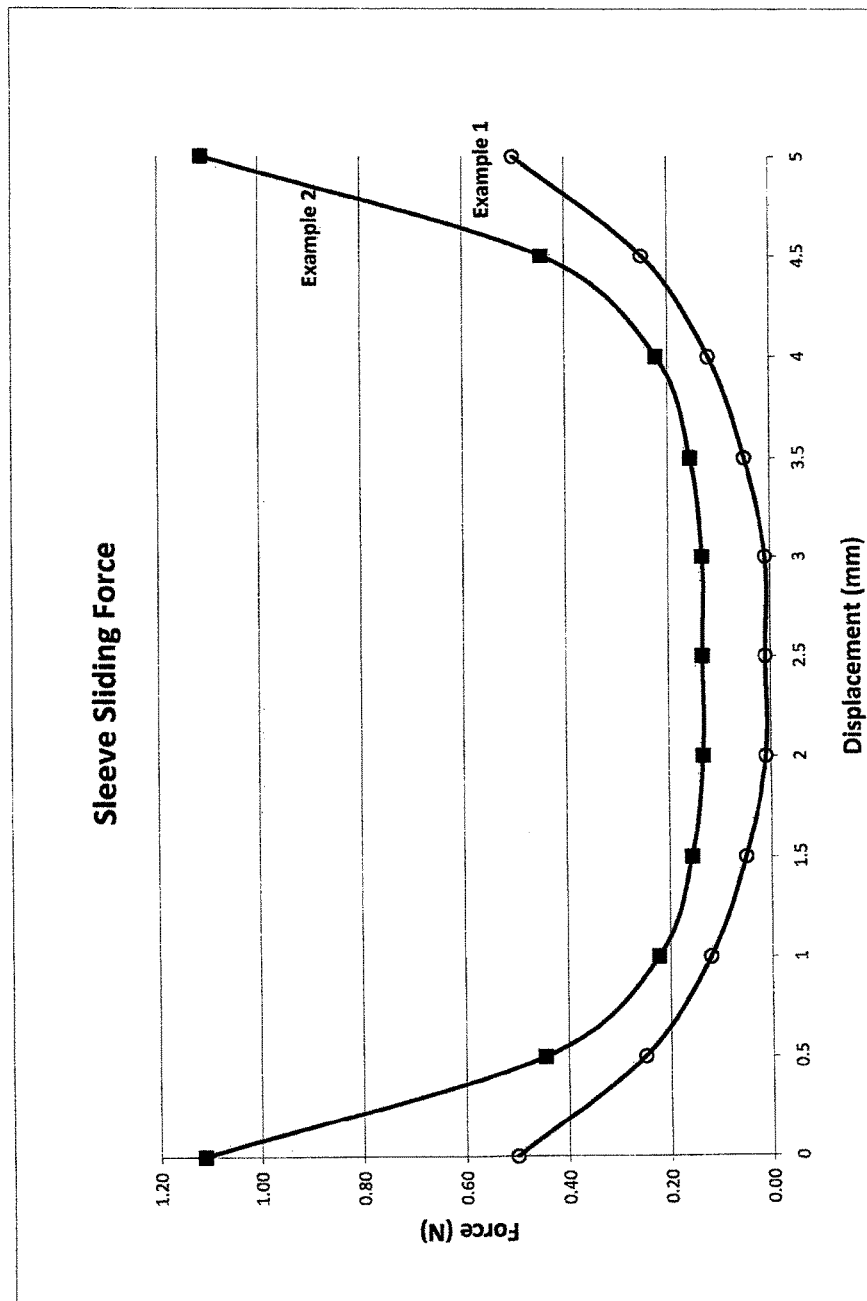
FIG. 46 is a graphic depiction of the amount of resistance force generated by a dynamic sleeve according to one variation.

Some variations of the dynamic sleeve provide a variable force that follows a U-shaped curve, as described further in Example 1 and FIG. 46. Here the highest resistance is encountered at the beginning and the end of dynamic sleeve movement along the housing with decreased resistance between the start and end points of dynamic sleeve travel. In use, this translates to having an initial high-resistance phase (upon initial placement on the eye wall) followed by a decrease in resistance to sleeve movement during needle advancement into the eye cavity. When the needle is fully deployed, the dynamic sleeve will typically be at the end of its travel path, and increased resistance would again be encountered. This increase in resistive force allows the sleeve to come to a smooth, gradual stop (instead of an abrupt hard stop at the end point) to minimize the risk of transmitting damaging amounts of force to the inert eye wall (which in turn minimizes the risk of causing discomfort or injury to the eye). Here an exemplary dynamic sleeve may be configured to be tapered at the proximal end and distal end. Referring to the sectional view in FIG. 42, integrated injection device (42) includes a housing (44), a resistance band (46) wholly or partially surrounding the housing, and a dynamic sleeve (48) that can be slidably advanced and retracted upon the housing (44). When partially surrounding the housing, the resistance band may be referred to as a resistance strip. The dynamic sleeve (48) has a proximal end (50) and a distal end (not shown) that are tapered. The tapered ends may provide higher traction at the beginning and the end of the dynamic sleeve travel path along the device housing (44) (that is at the beginning and end of needle deployment). The taper at the proximal end (50) provides higher traction and resistance at the beginning of dynamic sleeve movement when it contacts resistance band (46). The thickness of the resistance band (46) may be varied to adjust the amount of resistance desired. For example, the thickness of the resistance band may range from about 0.01 mm to about 5 mm, or range from about 0.1 mm to about 1 mm. Specifically, the thickness of the resistance band may be about 0.05 mm, about 0.1 mm, about 0.2 mm, about 0.3 mm, about 0.4 mm, about 0.5 mm, about 0.6 mm, about 0.7 mm, about 0.75 mm, about 0.8 mm, about 0.9 mm, about 1.0 mm, about 1.5 mm, about 2.0 mm, about 2.5 mm, about 3.0 mm, about 3.5 mm, about 4.0 mm, about 4.5 mm, or about 5.0 mm. The width of the resistance band may also vary and be about 1.0 mm, about 1.5 mm, about 2.0 mm, about 2.5 mm, about 3.0 mm, about 3.5 mm, about 4.0 mm, about 4.5 mm, or about 5.0 mm. Upon reaching the wider middle segment (52), lower-traction and lower resistance movement is encountered, followed by higher traction and higher resistance at the end of needle deployment as the taper at the distal end of the dynamic sleeve is reached. As the dynamic sleeve becomes progressively more tapered at the distal end, more traction is produced against the device housing until it gradually comes to a complete stop. Instead of both ends being tapered, in some variations one of the proximal end and distal end of the dynamic sleeve may be tapered.

Variable traction force may also be provided by components such as circular raised bands or ridges on the outside surface of the device tip. These components may provide counter-traction when approximated against another circular raised band or ridge on the inside surface of the movable dynamic sleeve (inner bands or ridges). When the outer and inner bands or ridges are in contact with each other before the dynamic sleeve begins to move, they generate high traction and high resistance to dynamic sleeve movement. Once the dynamic sleeve starts to move, the raised band on the outside of the device housing moves past the raised band on the inside of the dynamic sleeve, which may result in a rapid decrease in resistance to dynamic sleeve movement and, therefore, decreased pressure on the eye wall by the device tip. The shape of the raised interlocking bands or ridges will generally determine the shape of resistance decrease. For example, the resistance decrease may follow a sine-shaped profile.

In another variation, the dynamic sleeve may generate a force that continuously decreases from its highest point before needle deployment (when the dynamic sleeve completely covers the needle), to its lowest point when the dynamic sleeve begins to move to expose the needle tip. Here the force remains low until the end of dynamic sleeve travel and complete needle deployment. This pattern of resistance decrease may follow a sine-shaped curve.

Slidable advancement of the dynamic sleeve may generate a force between itself and the housing ranging from 0 N to about 2 N. In some instances, slidable advancement of the dynamic sleeve generates a force between itself and the housing ranging from about 0.1 N to about 1 N.

Measuring Components

The devices described here may include a measuring component that may be useful in determining the location of the intraocular injection site on the eye surface. Integrated devices will generally include a measuring component. Some variations of the device may include a ocular contact surface having a high-traction surface integrated with a measuring component. The measuring component may be fixedly attached or removably attached to the ocular contact surface. The measuring component may also be configured to fully (360 degrees) or partially rotate (less then 360 degrees) about the long axis of the device housing. Inclusion of a rotatable (dynamic) measuring component may allow the operator to maintain a comfortable grasp of the device without having to change or reposition the finger placement pattern in order to appropriately orient the measuring component toward the limbus in any meridian either in the left or right eye of a mammal (for example perpendicular to the limbus), in order to accurately determine the injection site and before stably positioning the device tip on the eye surface. A rotating (dynamic) measuring component may also enable sterile localization of injection site in any meridian/clock hour relative to limbus circumference, while avoiding contact with the eyelids or eyelashes.

Figure 8:
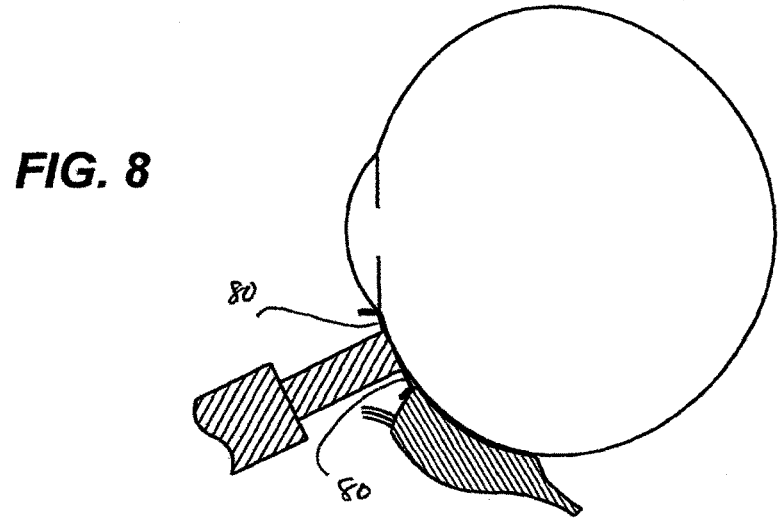
FIG. 8 illustrates how an exemplary measuring component works to retract the eyelid and measure a certain distance from the limbus.

As previously stated, the measuring component may be raised above the ocular surface so that it prevents the eye lid from coming in contact with the sterile ocular contact surface of the device tip (e.g., FIGS. 2A-2B and 8). The specific configuration of the measuring component may also help to minimize the risk of inadvertent contamination of the sterile drug dispensing member (conduit) such as an injection needle. Such contamination may result from various causes such as the sterile needle coming in inadvertent contact with an eyelid or other non-sterile surface. The measuring components may also be colored in a manner to provide color contrast against the surface of the eye including the conjunctiva, the sclera, and the iris. The distance from the deployed needle tip to the tip of each individual measuring component may be about 4 mm. Here the distance from the needle tip to the outer edge of corneo-scleral limbus may be about 3.5 mm. In some instances, e.g., when the measuring component comprises two tabs, and the tabs are rotated so that the tips of the tabs are simultaneously touching the outer edge of corneo-scleral limbus, the injection site is located at 3.5 mm from limbus (ranging from 1 to 4 mm).

In general, the measuring component will enable the intraocular injection site to be more precisely placed at a specific distance from, and posterior or anterior to, the corneal-scleral junction termed "the limbus." In some variations, the measuring component may provide for placement of the intraocular injection site from about 1 mm to about 5 mm, from about 2 mm to about 4.5 mm, or from about 3 mm to about 4 mm, from and posterior to the limbus. In another variation, the measuring component may provide for placement of the intraocular injection site from about 2 mm to about 5 mm posterior to the limbus, or about 3.5 mm posterior to the limbus. In other variations, the measuring component may provide for placement of the intraocular injection site from within about 3 mm or about 2 mm, from and anterior to, the limbus, or between about 0.1 mm and about 2 mm from and anterior to the limbus. In one variation, the measuring component provides for placement of the intraocular injection site between about 1 mm anterior to the limbus and about 6 mm posterior to the limbus. In another variation, the measuring component provides for placement of the intraocular injection site between about 3 mm to about 4 mm posterior to the limbus.

The measuring components may have any suitable configuration. For example, the measuring components may be located on one side of the ocular contact surface or on more than one side of the ocular contact surface (e.g., FIGS. 9, 10, and 11). Here, when the tip of the measuring component is placed right next to the corneo-scleral limbus, the site of the intraocular needle injection is placed at a particular distance from the limbus, e.g., between about 3 mm and about 4 mm posterior to the limbus.

In alternative variations, the measuring component comprises one or more members (e.g., FIGS. 9, 10, and 11). These members may radially extend from the ocular contact surface. Having more than one member comprise the measuring component may be beneficial in ensuring that the distance between the limbus and injection site is measured perpendicular to the limbus and not tangentially as it may be the case when the measuring means comprise a single member. When the tips of one or more than one radial member comprising the measuring component are aligned along the corneo-scleral limbus, the site of the intraocular needle injection is placed at a particular distance from the limbus, such as between about 3 mm and about 4 mm posterior to the limbus.

More specifically, as shown in FIG. 8, the device tip having an ocular contact surface comprises a measuring component (80) that enables the determination of the injection site at a certain distance relative to the corneo-scleral limbus. As previously stated, in one variation the measuring component is located on one side of the device tip. In another variation, more than one measuring component is located on more than one side of the device tip. In yet further variations, the tip of the measuring component may be raised, bent, etc., which prevents the eye lid from sliding over the measuring component and coming in accidental contact with the dispensing member (conduit) of device. Also in FIG. 8, the dispensing member (conduit) is shown as being completely shielded inside the device tip.

FIG. 9 provides further detail about another variation of the measuring component. Here the device tip comprises a ring-shaped ocular contact surface (90) and a measuring component (91) that enables the determination of the injection site at a certain distance relative to the corneo-scleral limbus. The outer circumference of the device tip that comes into contact with the surface of the eye has, e.g., a ring shaped ocular interface, and the dispensing member such as an injection needle may be hidden inside and protected by the device tip. In FIG. 9, the measuring components (91) are located on one side of the device tip (FIGS. 9A-9B) or on more than one side of the device tip (FIG. 9C). Thus, when the tip of the measuring component is placed next to the corneo-scleral limbus, the site of intraocular needle injection is placed at a specific distance from the limbus, such as between about 3 mm and about 4 mm posterior to the limbus. Any suitable number of measuring components may be provided on the device tip, e.g., attached to the ocular contact surface. When a plurality of measuring components are used, they may be arranged around the ocular contact surface in any suitable fashion. For example, they may be circumferentially disposed around the ocular contact surface or on one side of the ocular contact surface. They may be equally or unequally spaced around the circumference of the ocular surface. In other variations, the measuring components may be symmetrically spaced or asymmetrically spaced around the circumference of the ocular contact surface. These configurations may be beneficial in allowing the injector to rotate the device along its long axis.

FIGS. 10A-10C provide additional views of measuring components that are similar to those shown in FIGS. 9A-9C. In FIG. 10, a ring-shaped ocular contact surface (93) is shown having a measuring component (93) that enables the determination of the injection site at a certain distance relative to and perpendicular to the corneo-scleral limbus (94). The measuring components are depicted on one side of the device tip, or in another variation, on more than one side of the device tip. Again, the measuring components may comprise one or more members. Having more than one member comprise the measuring component may be beneficial in ensuring that the distance between the limbus and injection site is measured perpendicular to the limbus and not tangentially as it may be the case when the measuring component comprise a single member. When the tips of all members comprising the measuring component are aligned along the corneo-scleral limbus, the site of the intraocular needle injection is placed at a particular distance from the limbus, such as between about 3 mm and about 4 mm posterior to the limbus.

More than one measuring component is also shown in FIGS. 11A-11D. Here the measuring components (95) are depicted as extending from a common attachment point (96) on the ocular contact surface. When the tips of all members comprising the said measuring component are aligned along the corneo-scleral limbus, the site of the intraocular needle injection is placed at a particular distance from the limbus, such as between about 3 mm and about 4 mm posterior to the limbus.

Figure 44A:
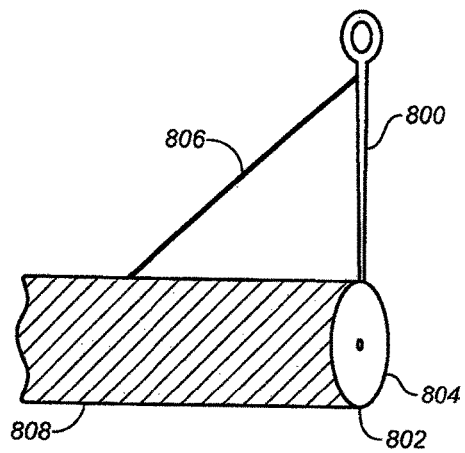
FIGS. 44A-44D depict exemplary positional indicator components.
Figure 44B:
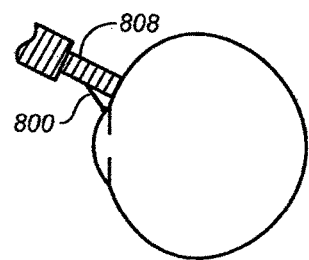
Figure 44C:
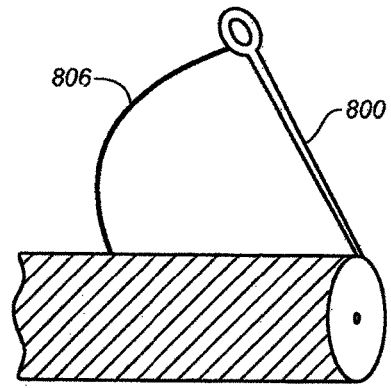
Figure 44D:
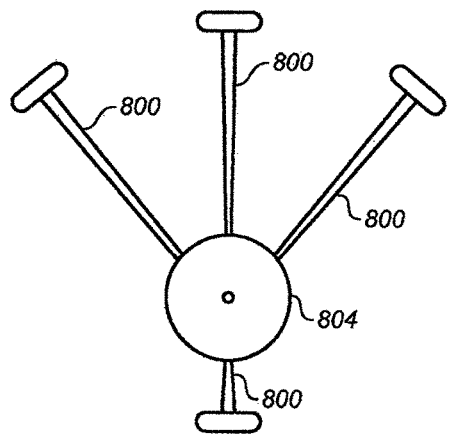

Alternatively, the measuring components may be configured as one or more flexible measuring strips. Flexible materials that may be used to make the measuring strips include flexible polymers such as silicones. As shown in FIG. 44A, the measuring strip (800) may extend from the device tip (802), usually from the side of the ocular contact surface (804), so that the distance between the limbus and injection site can be measured perpendicular to the limbus. A positional indicator component (806) may be employed to ensure that the measuring strip (800) is properly used. For example, as shown in FIG. 44B, correct positioning of the measuring strip (800) (so that a 90 degree angle is formed between the measuring strip and device housing (808)) may be determined when the positional indicator component is substantially taut. In contrast, a slack positional indicator component (as shown in FIG. 44C) would indicate incorrect positioning. The positional indicator component may be a cord. In one variation, the integrated device comprises at least three measuring strips. In another variation, the integrated device includes at least four measuring strips. When a plurality of measuring strips are used, they may be configured in any suitable manner around the tip of the integrated device (equally spaced around the circumference of the ocular contact surface, symmetric or asymmetrically placed around the circumference of the ocular contact surface, etc.). For example, as shown in FIG. 44D, the measuring strips may be configured to span the desired 90 degree angle (45 degrees plus 45 degrees between the farthest strips) to allow for a 90 degree rotation of a control lever without having to reposition the hand of the user.

Figure 12:
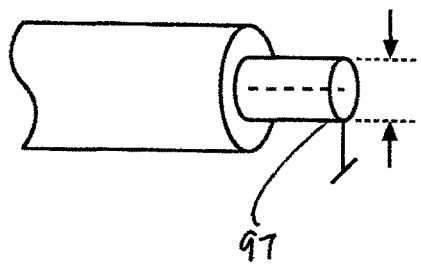
FIG. 12 shows an exemplary device that includes a marking tip member.
Figure 13:
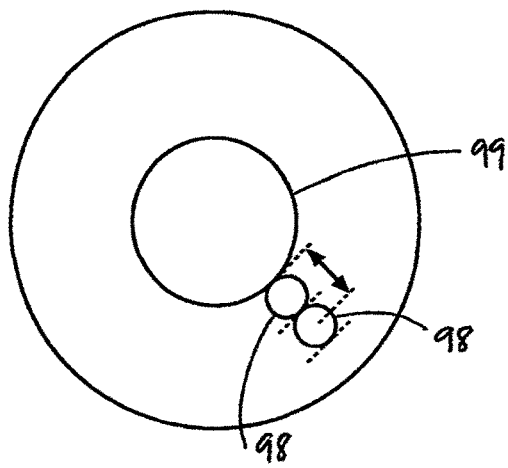
FIG. 13 illustrates how marks made on the surface of the eye by an exemplary marking tip member can be used to position the device at a target injection site.

In some variations, the measuring component may be configured as a marking tip member (97). As shown in FIG. 12, the marking tip member (97) at its distal end (closer to the eye) that interfaces with the ocular surface and leaves a visible mark (98) on the conjunctival surface when pressed against it (e.g., FIG. 13). The marker-tip enables intraocular injections to be carried out through a safe area of the eye relative to the corneo-scleral limbus (99), such as between about 3 mm and about 4 mm posterior to the limbus, over the pars plana region of the ciliary body of the eye. The diameter of the marking tip may range from about 1 mm to about 8 mm, or from about 2 mm to about 5 mm, or from about 2.3 mm to about 2.4 mm (e.g., FIG. 12).

In further variations, the measuring component may be a sectoral measuring component. The sectoral measuring component may be configured to span a sector of between about 1 degree and about 180 degrees of arc (e.g., between about 45 degrees and 90 degrees of arc) at the distal end of device or housing. In general, by "sectoral" it is meant that only a portion or section of the measuring component includes elements for taking measurements. For example, a sectoral measuring component may include radially extending members that are spaced from about 1 degree to about 90 degrees about the circumference of the device tip. During precise localization of the injection site, a sectoral measuring component configured in this manner may enhance sterility of the procedure because the measuring component can be oriented toward the limbus and away from periocular appendages such as the eyelids and eye lashes. Here the sectoral measuring component may avoid contact with the appendages, thus minimizing the risk of bacterial contamination and intraocular infection, while enabling precise localization of the injection site relative to the limbus in a sterile manner.

Figure 47:
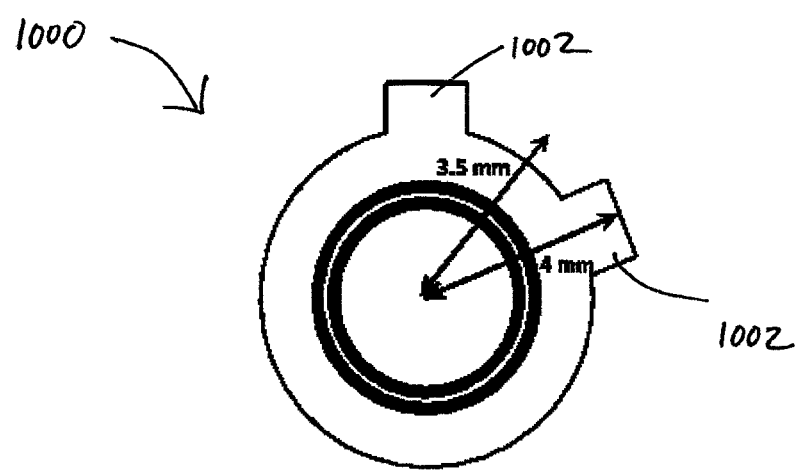
FIG. 47 depicts an end view of an exemplary sectoral measuring component.

In one variation, the sectoral measuring component may comprise a central (core) member having a proximal end and a distal end, and comprising a plurality of radially oriented spokes or tabs as the radially extending members, which are equal in length. Central member may be round, oval, square, rectangular or triangular in shape having a circumference or a perimeter. When central member is round, its diameter may be between about 1.0 mm and about 8.0 mm, or between about 3.0 mm and about 6.0 mm. Radially extending members may have the same fixed angle between any two adjacent members, for example, between 1 degree and 90 degrees, or between 15 degrees and 45 degrees. The radially extending members may also have the same length, so that the distance between the needle exit point and the tip of each individual radial member tip is substantially the same, for example between about 1.0 mm and about 5.0 mm, or between about 3.0 mm and about 4.0 mm. With this configuration, the sectoral measuring component may provide fine adjustment of device positioning on the ocular surface around the limbus circumference while rotating the entire device between 1 and 180 degrees (or between 1 and 90 degrees) and using any one or plurality of spokes or tabs to measure the distance between injection site and the limbus. As shown in FIG. 47, using any single tab or spoke (1002), or any two adjacent tabs or spokes (1002) of a sectoral measuring component (1000) that simultaneously touch the limbus line enables the measurement of two fixed distances relative to the limbus, for example 4 mm and 3.5 mm, respectively. More specifically, when the measuring component is rotated so that the tip of only one tab or spoke touches the limbus line while the tab or spoke is perpendicular to the limbus line, the injection site is localized at about 4 mm (ranging from about 3 mm to about 5 mm) from the limbus. When the measuring component is rotated so that the tips of two tabs or spokes are simultaneously touching the limbus line, the injection site is at about 3.5 mm from limbus (ranging from about 1 mm to about 4 mm).

In another variation, three divergent measuring tabs or spokes may comprise the measuring component. In a further variation, two divergent measuring tabs or spokes may comprise the measuring component. The divergent measuring tabs or spokes may span a curvilinear distance between about 30 degrees and about 180 degrees or between about 45 degrees and about 90 degrees on the distal surface of the device tip. Having the measuring tabs or spokes protrude only on one side of the device tip that is oriented towards the limbus and away from the eyelid may be helpful in ensuring that the measuring tabs do not become contaminated by touching the eyelids or eyelashes.

Conduits

The intraocular drug delivery devices described here may include any suitable conduit (or dispensing member) for accessing the intraocular space and delivering active agents therein. The conduits may have any suitable configuration, but will generally have a proximal end, a distal end, and a lumen extending therethrough. In their first, non-deployed (pre-deployed) state, the conduits will generally reside within the housing. In their second, deployed state, i.e., after activation of the actuation mechanism, the conduit, or a portion thereof, will typically extend from the housing. By "proximal end" it is meant the end closest to the user's hand, and opposite the end near the eye, when the devices are positioned against the eye surface.

The distal end of the conduit will generally be configured to be sharp, beveled, or otherwise capable of penetrating the eye surface, e.g., the sclera. The conduit employed may be of any suitable gauge, for example, about 25 gauge, about 26 gauge, about 27 gauge, about 28 gauge, about 29 gauge, about 30 gauge, about 31 gauge, about 32 gauge, about 33 gauge, about 34 gauge, about 35 gauge, about 36 gauge, about 37 gauge, about 38 gauge, or about 39 gauge. The wall of the conduit may also have any suitable wall thickness. For example, in addition to regular wall (RW) thickness, the wall thickness of the conduit may be designated as thin wall (TW), extra/ultra thin wall (XTW/UTW), or extra-extra thin wall (XXTW). These designations are well known to those of skill in the relevant art. For example, the conduit may be a fine gauge cannula or needle. In some variations, the conduits may have a gauge between about 25 to about 39. In other variations, the conduits may have a gauge between about 27 to about 35. In yet further variations, the conduits may have a gauge between about 30 to about 33.

Figure 14A:
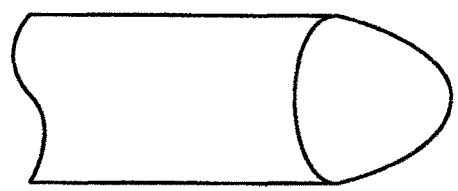
FIGS. 14A-14C show perspective views of exemplary sharp conduits.
Figure 14B:
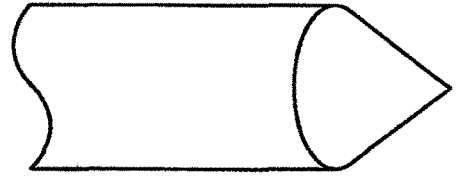
Figure 14C:
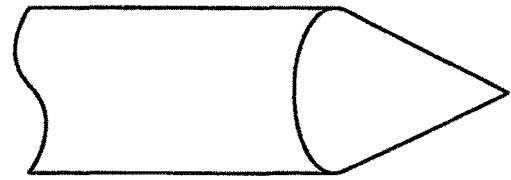

The conduits may have a sharp, pointed tip (FIGS. 14B-14C and FIGS. 15A1-15A2), rather than a rounded one (FIG. 14A) as in conventional needles. The pointed needle tip is formed by the lateral side surfaces that are straight at the point of their convergence into the tip, and at the point of their convergence forming a bevel angle (the angle formed by the bevel and the shaft of the needle), which may range from between about 5 degrees and about 45 degrees (FIG. 14B), between about 5 degrees and about 30 degrees, between about 13 degrees to about 20 degrees, or between about 10 degrees and about 23 degrees (FIG. 14C).

The sharp, pointed needle tip may provide improved penetration of the needle through the fibrillar, fibrous scleral tissue, which is the major structural cover of the eye and consists of a network of strong collagen fibers. Thus, such a needle tip during its penetration through the eye wall may create less resistance and, thus, decrease the impact force that is transmitted to the intraocular structures, such as the retina and the crystalline lens, in turn causing less damage to intraocular structures during the intraocular injection process (compared to conventional needles).

In addition, such a narrow bevel angle may enable the needle to cause less sensation when it penetrates through the eye wall (the outer cover of the said eye wall being richly innervated with sensory nerve fibers endings particularly densely located in the conjunctiva and cornea), which may be an issue when intraocular injections are involved compared to other less sensitive sites.

The narrow bevel angle may also allow for a longer bevel length and larger bevel opening and, thus, a larger opening at the distal end of the injection needle. With such a configuration, the force of drug injection into an eye cavity may be reduced, thus reducing the chances of intraocular tissue damage by a forceful stream of injected substance, which may occur with conventional short-beveled needles.

In some variations, the conduits are injection needles having one or more flat surface planes, as well as one or more side-cutting surfaces, as illustrated in FIGS. 16 and 17. Examples include a needle shaft comprising multiple surface planes separated by sharp ridges (FIGS. 16A-16C), as well as a needle tip comprising sharp side-cutting surfaces located on either side of the beveled surface of the needle about 90 degrees from the beveled surface (FIG. 17). The conduit may also be bi-beveled, i.e., have two bevels facing about 180 degrees from each other that is located on the opposite sides of the conduit. The conduit may also be coated (e.g., with silicone, PTFE, etc.) to facilitate its penetration through the eye wall.

Figure 18A:
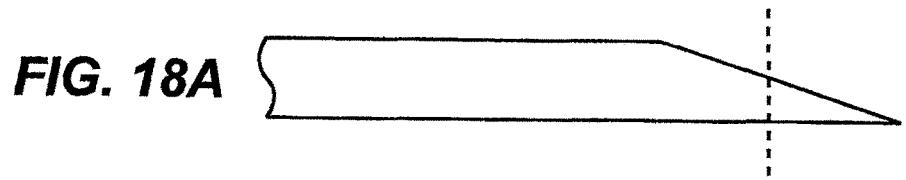
FIGS. 18A-18C show side and cross-sectional views (taken along line A-A) of an exemplary flattened conduit.
Figure 18B:
Figure 18C:

In other variations, the conduit may be configured to be wholly or partially flattened in at least one dimension, as shown in the cross-sectional view of FIG. 18C taken along the line A-A of FIG. 18A. For example, the conduit may be flattened in the anterior-posterior dimension (that is from the beveled side of the needle towards its opposite side. In one variation, both the external and internal surfaces of the needle are flattened and represent ovals on cross-section. In another variation, the internal surface of the needle is round and represents a circle on cross-section, while the external surface of the needle is flattened to enable its easier penetration through the fibrous scleral or corneal tissue of the eye wall. In another variation, more than one external surface plane of the needle is flattened to enable its easier penetration through the fibrous eye wall, while the internal opening of the said needle may be of any shape including round or oval.

As previously stated, in its second, deployed state, the conduit or needle extends from the housing. The portion of the needle that extends from the housing can be referred to as the exposed needle length. Upon activation of the actuation mechanism, the needle goes from its first, non-deployed state (pre-deployed state) (where it is entirely within the housing of the device), to its second, deployed configuration outside the housing, where a certain length of it is exposed. This exposed length may range from about 1 mm to about 25 mm, from about 2 mm to about 15 mm, or from about 3.5 mm to about 10 mm. These exposed needle lengths may enable complete intraocular penetration through the sclera, choroid and ciliary body into the vitreous cavity, while minimizing the risk of intraocular damage. In some variations, the exposed needle length ranges from about 1 mm to about 5 mm, or from about 1 mm to about 4 mm, or from about 1 mm to about 3 mm. Here the exposed needle lengths may enable complete intraocular penetration through the cornea into the anterior chamber, while minimizing the risk of intraocular damage.

Figure 19:
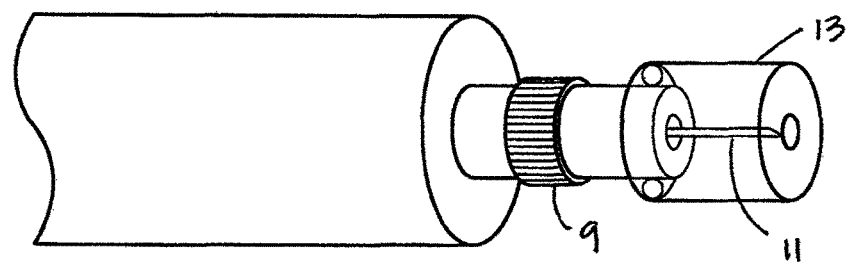
FIG. 19 shows an exemplary mechanism for controlling exposure of the conduit.
Figure 20:
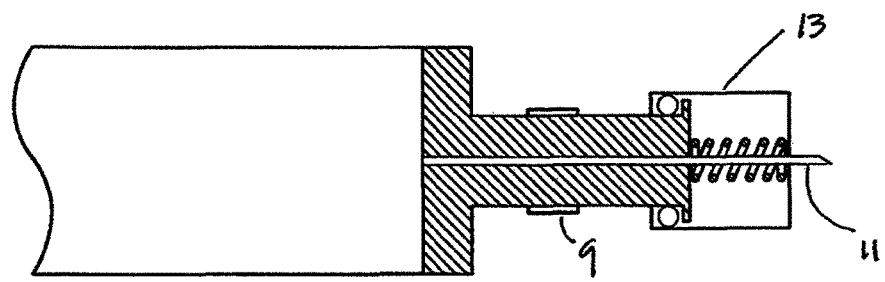
FIG. 20 provides another exemplary conduit exposure control mechanism.

In some variations, the devices may include an exposure control mechanism (9) for the dispensing member (11) (conduit) (FIGS. 19 and 20). The exposure control mechanism (9) generally enables one to set the maximal length of the dispensing member exposure during dispensing member deployment. In one variation, the exposure control mechanism works by providing a back-stop for the needle-protective member (13). In another variation, the exposure control mechanism (9) may be a rotating ring member with a dialable gauge. Needle exposure could be adjusted by the millimeter or a fraction of the millimeter, e.g., 1 mm, 1.5 mm, 2 mm, 2.5 mm, 3 mm, etc. Here the device may be equipped with a retraction mechanism that controls needle retraction into a needle-protective member. Such a needle-retraction mechanism may be spring-actuated (FIG. 20).

Figure 21:
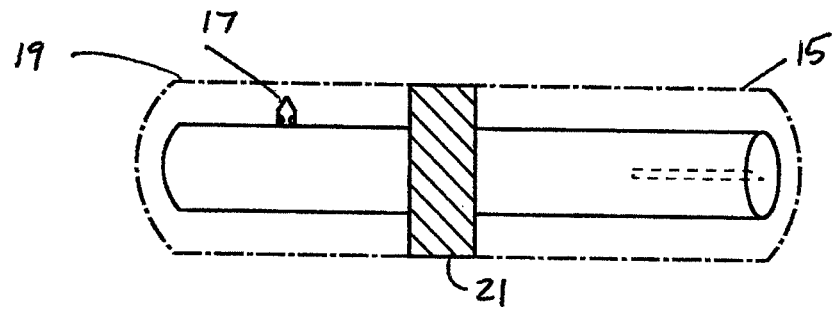
FIG. 21 shows an exemplary device having a front cover and back cover.

The devices may also include a removable distal (towards the eye) member that covers and protects the conduit (e.g., the front cover (15) in FIG. 21). In one variation, the devices may also include a removable proximal (away the eye) member that covers and protects the proximal part of the device, e.g., comprising a loading dock mechanism (17) (e.g., the back cover (19) in FIG. 21).

Some variations of the devices described herein comprise a needle stabilization mechanism configured to provide a steady and consistent needle alignment that is perpendicular to the ocular contact surface, and, therefore, perpendicular to the eye surface. This allows the operator to precisely control the angle of needle penetration into the eye by controlling the position of the device tip and housing relative to the eye surface. For example, the needle stabilization mechanism may be configured so that the needle exits the device tip through its central point (e.g., at the geometric center of a round tip) at 90 degrees relative to the tip outer surface (e.g., the ocular contact surface). In some instances, an injection angle other than 90 degrees (when the long axis of the device is not completely perpendicular to the eye surface at the injection site), may lead to inadvertent intraocular trauma to the crystalline lens or the retina. However, in other instances it may be useful for the needle to exit the tip at an angle less than 90 degrees relative to eye surface, in a direction parallel to the limbus.

Reservoirs

The reservoir is generally contained within the housing and may be configured in any suitable manner, so long as it is capable of delivering an active agent to the intraocular space using the actuation mechanisms described herein. The reservoir may hold any suitable drug or formulation, or combination of drugs or formulations to the intraocular space, e.g., the intravitreal space. It should be understood that the terms "drug" and "agent" are used interchangeably herein throughout. In one variation, the drug reservoir is silicone oil-free (lacks silicone oil or one of its derivatives) and is not internally covered or lubricated with silicone oil, its derivative or a modification thereof, which ensures that silicone oil does not get inside the eye causing floaters or intraocular pressure elevation. In another variation, the drug reservoir is free of any lubricant or sealant and is not internally covered or lubricated with any lubricating or sealing substance, which ensures that the said lubricating or sealing substance does not get inside the eye causing floaters or intraocular pressure elevation.

In some variations, the reservoir is made of a material that contains a cyclic olefin series resin, a cyclic olefin ethylene copolymer including commercially available products such as Zeonex® cyclo olefin polymer (ZEON Corporation, Tokyo, Japan) or Crystal Zenith® olefinic polymer (Daikyo Seiko, Ltd., Tokyo, Japan) and APEL™ cyclo olefin copolymer (COC) (Mitsui Chemicals, Inc., Tokyo, Japan), a cyclic olefin ethylene copolymer, a polyethylene terephthalate series resin, a polystyrene resin, a polybutylene terephthalate resin, and combinations thereof. In one variation, it may be beneficial to use a cyclic olefin series resin and a cyclic olefin ethylene copolymer that have a high transparency, a high heat resistance, and minimal to no chemical interaction with a pharmacological product such as a protein, a protein fragment, a polypeptide, or a chimeric molecule including an antibody, a receptor or a binding protein.

Exemplary agents may be selected from classes such as anti-inflammatories (e.g., steroidal and non-steroidal), anti-infectives (e.g., antibiotics, antifungals, antiparasitics, antivirals, and antiseptics), cholinergic antagonists and agonists, adrenergic antagonists and agonists, anti-glaucoma agents, neuroprotection agents, agents for cataract prevention or treatment, anti-oxidants, antihistamines, anti-platelet agents, anticoagulants, antithrombics, anti-scarring agents, anti-proliferatives, anti-tumor agents, complement inhibitors (e.g., anti-C5 agents, including anti-C5a and anti-C5b agents), vitamins (e.g., vitamin B and derivatives thereof, vitamin A, depaxapenthenol, and retinoic acid), growth factors, agents to inhibit growth factors, gene therapy vectors, chemotherapy agents, protein kinase inhibitors, tyrosine kinase inhibitors, PEGF (pigment epithelial growth factor), small interfering RNAs, their analogs, derivatives, conjugates, and modifications thereof, and combinations thereof.

Particular agent classes that may be useful include without limitation, anti-neovascularization agents, anti-VEGF agents, anti-PDGF agents, anti-vascular permeability agents, protein kinase C inhibitors, EGF inhibitors, tyrosine kinase inhibitors, steroidal anti-inflammatories, nonsteroidal anti-inflammatories, anti-infectives, anti-allergens, cholinergic antagonists and agonists, adrenergic antagonists and agonists, anti-glaucoma agents, neuroprotection agents, agents for cataract prevention or treatment, anti-proliferatives, anti-tumor agents, complement inhibitors, vitamins, growth factors, agents to inhibit growth factors, gene therapy vectors, chemotherapy agents, protein kinase inhibitors, small interfering RNAs, aptamers, antibodies or antibody fragments, growth factor receptors and receptor fragments, analogs, derivatives, and modifications thereof, and combinations thereof.

Non-limiting, specific examples of drugs that may be used alone or as part of a combination drug therapy include Lucentis™ (ranibizumab), Avastin™ (bevacizumab), Macugen™ (pegaptanib), steroids, e.g., dexamethasone, dexamethasone sodium phosphate, triamcinolone, triamcinolone acetonide, and fluocinolone, taxol-like drugs, integrin or anti-integrin agents, vascular endothelial growth factor (VEGF) trap (aflibercept) (VEGF receptor fragments or analogs), anecortave acetate (Retaane), and limus family compounds. Non-limiting examples of members of the limus family of compounds include sirolimus (rapamycin) and its water soluble analog SDZ-RAD, tacrolimus, everolimus, pimecrolimus, and zotarolimus, as well as analogs, derivatives, conjugates, salts, and modifications thereof, and combinations thereof.

Topical anesthetic agents may also be included in the reservoirs. For example, lidocaine, proparacaine, prilocaine, tetracaine, betacaine, benzocaine, ELA-Max®, EMLA® (eutectic mixture of local anesthetics), and combinations thereof may be used.

Some variations of the injection devices described herein include a filter that filters the contents of the reservoir as it is delivered into the eye. For example, the filter may be used to remove infectious agents and enhance sterility of an active agent formulation before injection into the eye. Thus, inclusion of a filter into the device may be useful because the eye is an immune-privileged site, and introduction of even a small quantity of pathogens such as bacteria may cause sight-threatening intraocular infection (endophthalmitis). The filter may also be used to remove impurities, e.g., silicone droplets, from an active agent formulation prior to injection into the eye. This may be useful for intraocular drugs because a small impurity injected into a subject's eye may result in the subject seeing it as floater(s) that may be intractable, which significantly worsens the quality of vision.

In one variation, the filter pore size is between about 0.2 µm (microns) and about 10 µm (microns), between about 0.2 µm (microns) to about 4 µm (microns), or between about 0.1 µm (microns) and about 500 µm (microns) to facilitate filtration of bacterial pathogens, particulate matter or impurities such as silicone droplets from the outgoing drug being injected intraocularly. Thickness of the said may range from between about 50 µm (microns) to about 250 µm (microns), or from between about 10 µm (microns) to about 10000 µm (microns).

The filter may be made from any suitable non-reactive material, such as a low protein-binding material. Exemplary filter materials include without limitation, thermoplastic fluoropolymers such as PVDF (polyvinylidene fluoride); mixed cellulose esters; nylons; polyesters; nitrocelluloses; acrylic polymers such as Versapor® acrylic copolymer; polyethersulfones such as found in Supor™ filters; a combination, a mixture, or a blend thereof.

The filter may be integrated with the device housing, the reservoir, the conduit, or any part of the device. In one variation, the filter is internal to the device. For example, the filter is configured to be inside the drug reservoir, or inside the conduit, or at the junction between reservoir and conduit. In another variation, filter is detachable or removable from the device. In one variation, the filter is located within the reservoir at its distal end. In another variation, the filter is located at the proximal end of the lumen of the conduit. The filter may also be placed at any location within and along the lumen of the conduit, e.g., at its proximal end, in the middle, or at the distal end of the conduit.

The reservoirs and devices described here may be suitable for intraocular administration of a very small volume of a solution, suspension, gel or semi-solid substance. For example, a volume between about 1 µl and about 200 µl, or between about 10 µl and about 150 µl, or between about 20 µl and about 100 µl may be delivered. To that end, the device will generally have a very small "dead space," which enables intraocular administration of very small volumes.

The device reservoirs may be pre-loaded during the manufacturing process or loaded manually before the intraocular injection, as further described below.

Drug Loaders

Front loading of an injection device when the drug is loaded through the injection needle generally dulls the needle tip and removes at least some of the lubricant coating from the needle making it more difficult and uncomfortable for the needle to penetrate the target tissue. There is also a higher risk of contaminating the injection needle while manipulating it with a drug container. Back loading, for example through the plunger, often leads to wasting a significant amount of the drug, for example, more than 0.05-0.1 mL, which is undesirable with expensive agents, as well as when smaller drug volumes are used, as is typically the case for intravitreal injections. Here total volumes in the range of 0.05-0.1 ml are generally used. When a detachable needle is used, drug may be lost in the syringe luer and needle hub when the loading needle is exchanged with an injection needle, and contamination of the sterile drug conduit may occur. Thus, it would be beneficial to have a front-loading mechanism that allows for direct loading of the drug into drug reservoir without passing the drug through the tip of the drug conduit, exchanging or detaching the drug conduit, or losing a significant volume of the drug during the loading process.

Figure 22:
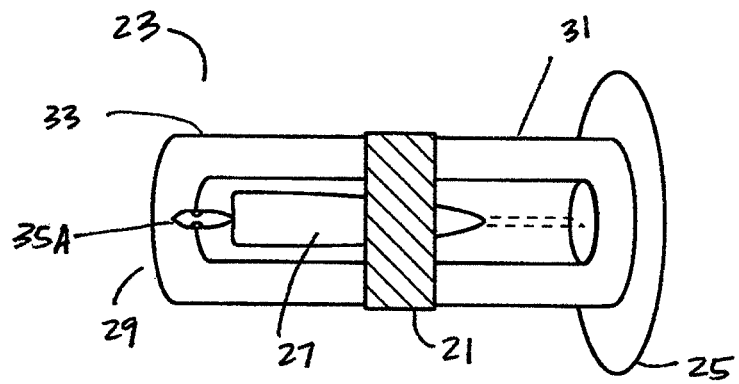
FIG. 22 illustrates how the device may be filled with a pharmaceutical formulation using an exemplary drug loading member.

In view of the above, when a drug or formulation is to be loaded into the reservoir of the devices described herein prior to intraocular injection, a loading member may be employed. The loading member may be removably attached to the distal end of the housing. For example, the loading member may function as a loading dock that quantitatively controls the volume of a liquid, semi-liquid, gelatinous, or suspension drug that is to be loaded into the device. For example, the loading member may comprise a dial mechanism (21) that allows the operator to preset a particular volume of a drug to be loaded into the device (FIGS. 21 and 22). The loading may occur with a precision raging from about 0.01 µl and about 100 µl, or from about 0.1 µl and 10 µl. Such a loading member may allow for loading the device reservoir with a liquid, semi-liquid, gelatinous or suspended drug in a particular volume equal or less than that of the drug storage container, which allows for airless loading of the drug into the device. This may be beneficial because air injected into the eye will result in the sensation of seeing "floaters" by the patient, which may be uncomfortable and distracting to the patient particularly during driving or other similar activities.

Figures 25A, 25B:
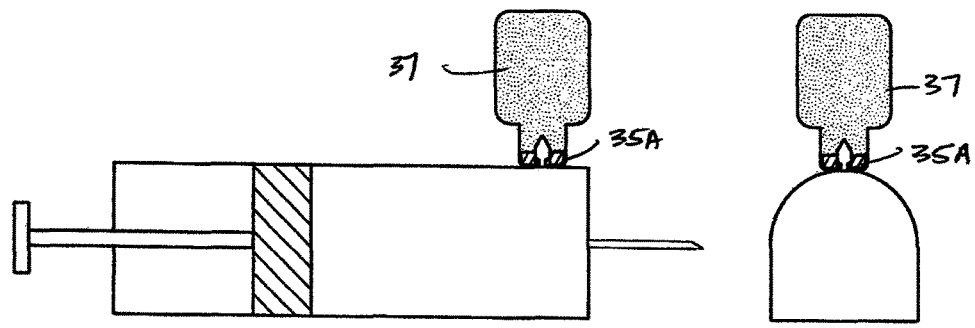
FIGS. 25A-25B show an exemplary fenestrated drug loading member interfaced with a drug source.

As shown in FIG. 22, the drug loading mechanism (23) includes a wide base member (25) for upright loading of the reservoir (27) through its proximal (further from the eye) end (29). Also shown are exemplary front (31) and back (33) covers, as well as a dialable control mechanism (21) for setting the loading and/or injection volume(s). In other variations, the devices comprise a loading mechanism such as a loading dock (35A), wherein the dock (35A) interfaces with a drug storage container (FIGS. 25A-25B) such as a vial known to those skilled in the art and penetrates through the vial stopper to gain access to the drug contained inside the vial so that the drug could be loaded into the device reservoir. In FIGS. 25A-25B, the dock mechanism is located in the dependant position so that the drug vial (37) is positioned directly above the dock so that the drug moves from the vial downward in the direction of gravity.

In one variation, the dock mechanism comprises a needle or a sharp cannula that has openings or fenestrations (39) at its base. The said openings or fenestrations are positioned immediately adjacent to the internal aspect of the vial stopper when the loading dock penetrates into the drug vial while in the desired loading position, which in turn enables airless drug loading into the device as well as complete drug removal from the storage container. Airless drug loading may be beneficial because it may prevent the patient from seeing small intraocular air bubbles or "floaters." Complete drug removal is also beneficial given that small drug volumes and expensive medications are typically used.

In other variations, for example, when the devices have a flat side surface (FIGS. 24A-24D) or a flat front or back surface (FIG. 22), the loading mechanism includes a loading dock located 180 degrees from the flat surface. This results in a loading dock pointing straight upwards, which enables its penetration into a drug container in the dependent position, which in turn enables airless drug delivery into the device, as well as complete drug removal from the storage container and its loading into the said device without drug retention and loss in the storage container.

In further variations, as shown in FIGS. 33A-33B, an access port (loading port) (144) may be provided at the distal end of the needle assembly (125) that allows drug from a storage container (146) to be loaded into the reservoir (122). Access port (144) may be placed at any suitable location on the needle assembly (125) or housing (102) to provide access to the reservoir. For example, if desired, the access port may be placed in the front wall (i.e., side or lateral wall) of the housing or even the ocular contact surface (not shown) so that drug loading occurs from the front of the device. The lateral access port may be configured to load drug through the wall of the device housing and into the reservoir in a manner that directs the drug toward the plunger seal and away from the internal opening of the injection needle. This way the small amount of the medication to be loaded does not get splashed over the front part of the drug reservoir. In some variations, the lateral access port is round or oval. When the access port is round, it may have a diameter ranging from between about 1.0 mm and 5.0 mm. The lateral access port may be positioned at about a 1 degree to about a 90 degree angle with respect to the axis of the plunger. With this orientation, direct visualization of drug loading may occur while moving the plunger.

Access port (144) may comprise a seal or a plug configured to seal the reservoir against air or fluid leak, and/or external bacterial contamination and may be made from any suitable material, e.g., silicone, rubber, or any soft thermoplastic polymer such as, but not limited to, polyurethane, Kraton™ styrenic block copolymers consisting of polystyrene blocks and rubber blocks, polyethylene, polypropylene, polyvinyl chloride, or combinations thereof that allows sealable penetration by a sharp conduit.

Figure 52A:
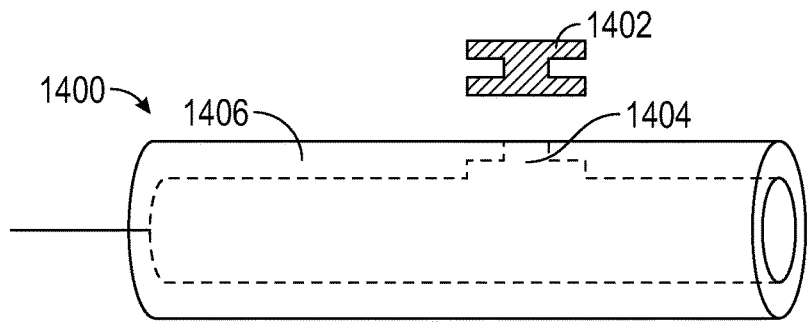
FIGS. 52A-52C show an exemplary access (drug loading) port in the injection device housing as well as an exemplary stopper for sealing an injection device access port, and how the location of the stopper corresponds with the location of an opening in a reservoir.
Figure 52B:
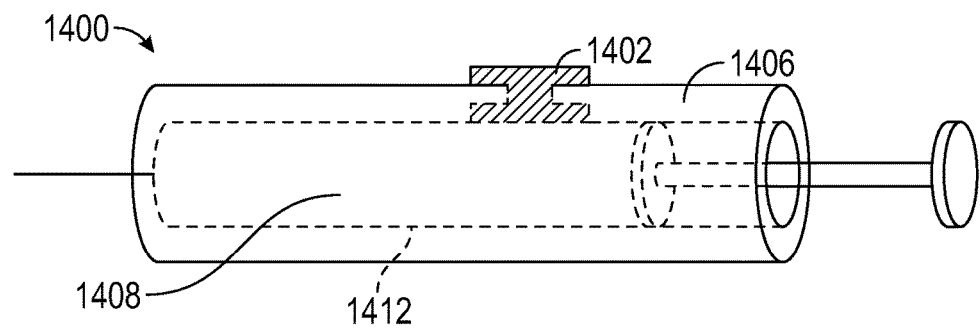
Figure 52C:
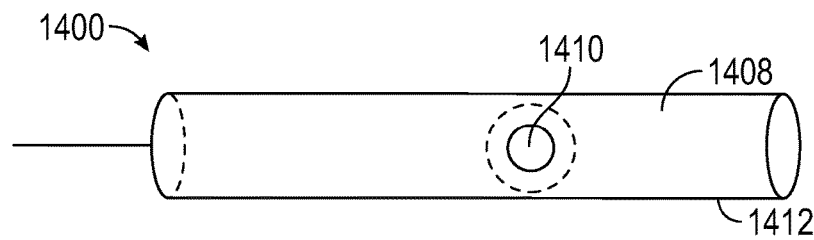

In some variations, the access port stopper or seal may comprise a fully or partially encircling sleeve. Here the sleeve may also serve as a finger grip or a holder. In another variation, and as shown in FIGS. 52A-52C, the injection device (1400) may include an H-shaped stopper or plug (1402) for sealing the access port (1404) that provides access through the housing wall (1406) of the device (1400) into the reservoir (1408). An opening (1410), e.g., in the wall of a needle assembly (1412) that contains the reservoir (1408), may be provided so that drug loading may occur through the access port (1404) and opening (1410) into the reservoir (1408). Here the H-shaped stopper or plug (1402) is flush with the internal surface of the reservoir (1408) when it is inserted to seal the access port (1404).

One or multiple membranes (148) may also be provided, e.g., in the ocular contact surface (108) to seal the internal compartment of the housing against air leak and/or external bacterial contamination. For example, the thickness of the membrane or the combined plurality of membranes may range from about 0.025 mm to about 5.0 mm, or range from about 0.1 mm to about 1 mm. One or multiple small apertures (150) may also be included in the wall of the housing (102) to help control air outflow from the housing (102). The number and diameter of the apertures (150) may be varied to control the rate of (needle assembly and) needle deployment.

Figure 38:
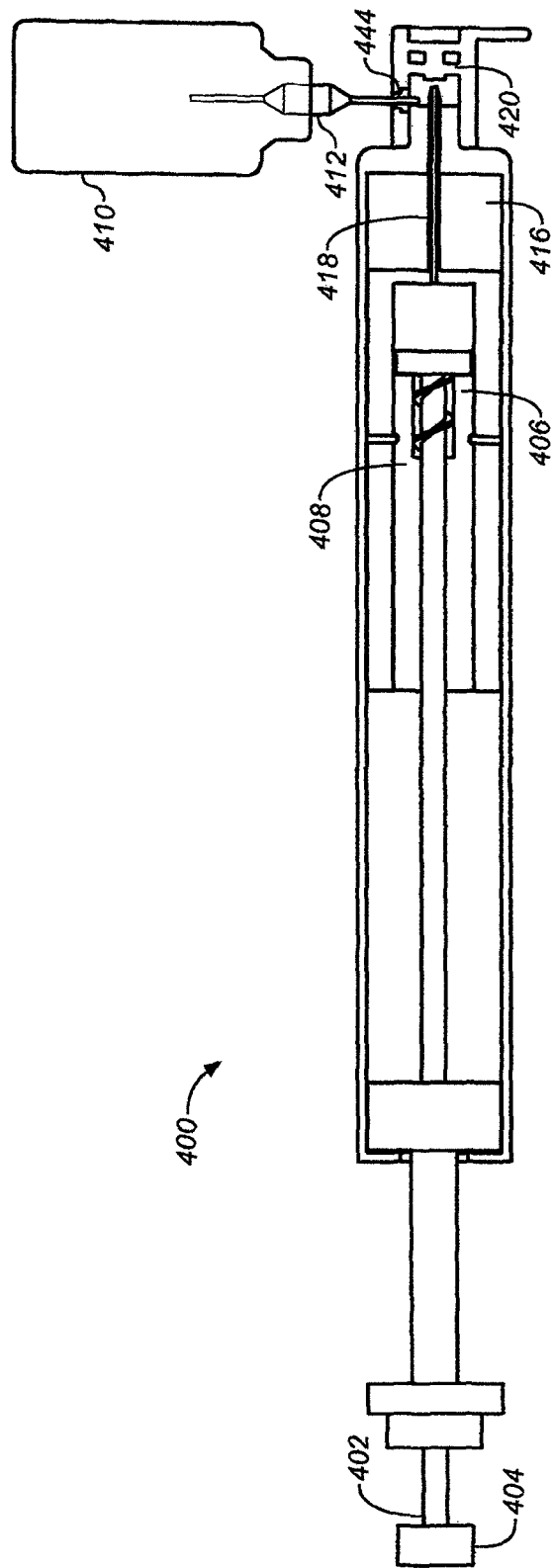
FIG. 38 is a side, cross-sectional view of an exemplary drug-loading piston.

In some variations, e.g., when a pneumatic actuation mechanism is used, drug loading may be controlled by a drug-loading piston. For example, as shown in FIG. 38, the device (400) may include a drug-loading piston (402) having a proximal end (404) and a distal end (406). The distal end (406) is adapted to include a threaded portion (408). Thus, during loading of a drug from container (410) through adaptor (412) and access port (414), the drug-loading piston (402) can be rotated and withdrawn to create negative pressure within the reservoir (416). This negative pressure in turn draws the drug through the needle (418) and into the reservoir (416). A receptacle (420) may also be provided at the distal end of the device for holding initially loaded drug prior to transfer into the reservoir (416).

Some variations of the drug loading devices include a filter that filters the contents of the drug container as it is delivered into the reservoir. For example, the filter may be used to remove infectious agents and enhance sterility of an active agent formulation before delivery into the reservoir. Thus, inclusion of a filter into the drug loader may be useful because the eye is an immune-privileged site, and introduction of even a small quantity of pathogens such as bacteria may cause sight-threatening intraocular infection (endophthalmitis). The filter may also be used to remove impurities, e.g., silicone droplets, from an active agent formulation as it is transferred to the reservoir and prior to injection into the eye. This may be useful for intraocular drugs because a small impurity injected into a subject's eye may result in the subject seeing it as floater(s) that may be intractable, which significantly worsens the quality of vision.

In one variation, the filter pore size is between about 0.2 μm (microns) and about 10 μm (microns) to facilitate filtration of bacterial pathogens from the outgoing drug being injected intraocularly. In another variation, the filter pore size is between about 0.1 μm (microns) and about 500 μm (microns) to facilitate filtration of particulate matter or impurities such as silicone droplets from the outgoing drug being injected intraocularly. In yet a further variation, the filter pore size is between about 0.2 μm (microns) to about 4.0 μm (microns). Thickness of the said filter may range from between about 50 μm (microns) to about 250 μm (microns), or from between about 10 μm (microns) to about 10000 μm (microns).

The filter may be made from any suitable non-reactive material, such as a low protein-binding material. Exemplary filter materials include without limitation, thermoplastic fluoropolymers such as PVDF (polyvinylidene fluoride); mixed cellulose esters; nylons; polyesters; nitrocelluloses; acrylic polymers such as Versapor® acrylic copolymer; polyethersulfones such as found in Supor™ filters; a combination, a mixture, or a blend thereof.

The filter may be integrated with the drug loading device housing, the reservoir, a conduit, or any suitable part of the device. In another variation, filter is detachable or removable from the device. In one variation, the filter is located within the reservoir at its distal end. In another variation, the filter is located at the proximal end of the lumen of the conduit. The filter may also be placed at any suitable location within and along the lumen of the conduit, e.g., at its proximal end, in the middle, or at the distal end of the conduit.

Actuation Mechanisms

The devices described here generally include an actuation mechanism within the housing that deploys the conduit from the housing and enables the delivery of drug from the device into the intraocular space. In other variations, the conduit is deployed by an actuation mechanism contained within a separate cartridge that can be removably attached to the device housing, e.g., using snap-fit or other interlocking elements. The actuation mechanisms may have any suitable configuration, so long as they provide for accurate, atraumatic, and controlled delivery of drug into the intraocular space. For example, the actuation mechanisms may deliver a drug or formulation into the eye by way of intraocular injection at a rate ranging from about 1 µl/sec to about 1 ml/sec, from about 5 µl/sec to about 200 µl/sec, or from about 10 µl/sec to about 100 µl/sec. The actuation mechanisms may generally provide a force of needle deployment that is strong enough to penetrate the eye wall comprising the conjunctiva, sclera and the pars plana region of the ciliary body, but less than that causing damage to the intraocular structures due to high velocity impact. This force depends on several physical factors, including but not limited to, the needle gauge utilized, the speed/rate of needle deployment at the point of contact between the needle tip and the eye wall which in turn determines the impact force. An exemplary range of force that may be generated by the actuation mechanisms is about 0.1 N (Newton) to about 1.0 N (Newton). The velocity of needle deployment may also range between about 0.05 seconds and about 5 seconds.

Figure 26A:
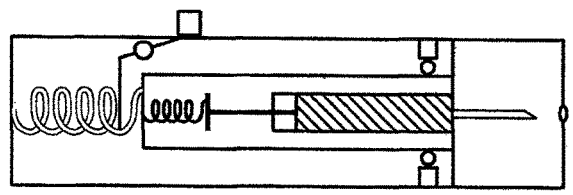
FIGS. 26A-26C depicts a side, cross-sectional view of an exemplary two-spring actuation mechanism.
Figure 26B:
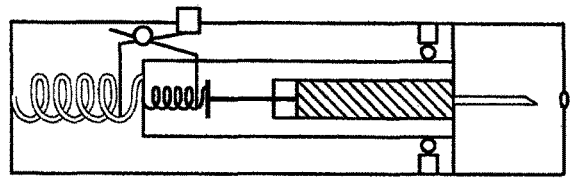
Figure 26C:
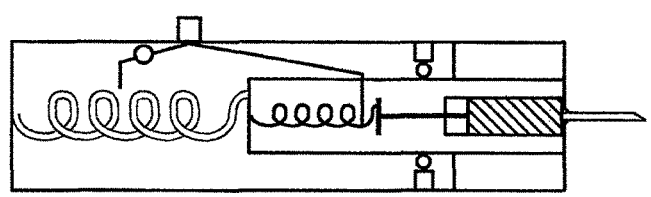
Figure 27:
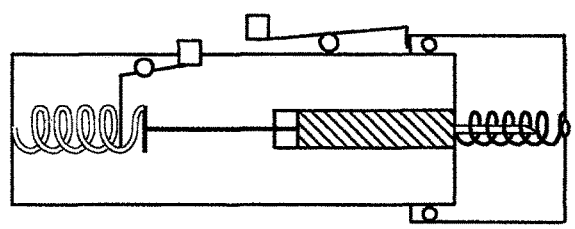
FIG. 27 is a side, cross-sectional view of another exemplary two-spring actuation mechanism.

In some variations, the actuation mechanism is a single-spring mechanism. In other variations, the actuation mechanism is a two-spring mechanism. In further variations, the actuation mechanism is pneumatic, e.g., employing negative pressure such as vacuum, or a positive pressure driven mechanism. In further variations, the actuation mechanism is driven magnetically or electrically, e.g., by a piezo-electric or magnetic rail mechanism. These types of actuation mechanisms may be configured to allow independent control of the rate and force of drug injection (controlled, e.g., by the first spring member in the two-spring variation), and the rate and force of the dispensing member deployment (controlled, e.g., by the second spring member in the two-spring variation). Exemplary two-spring mechanisms are shown in FIGS. 26 and 27.

Figure 28:
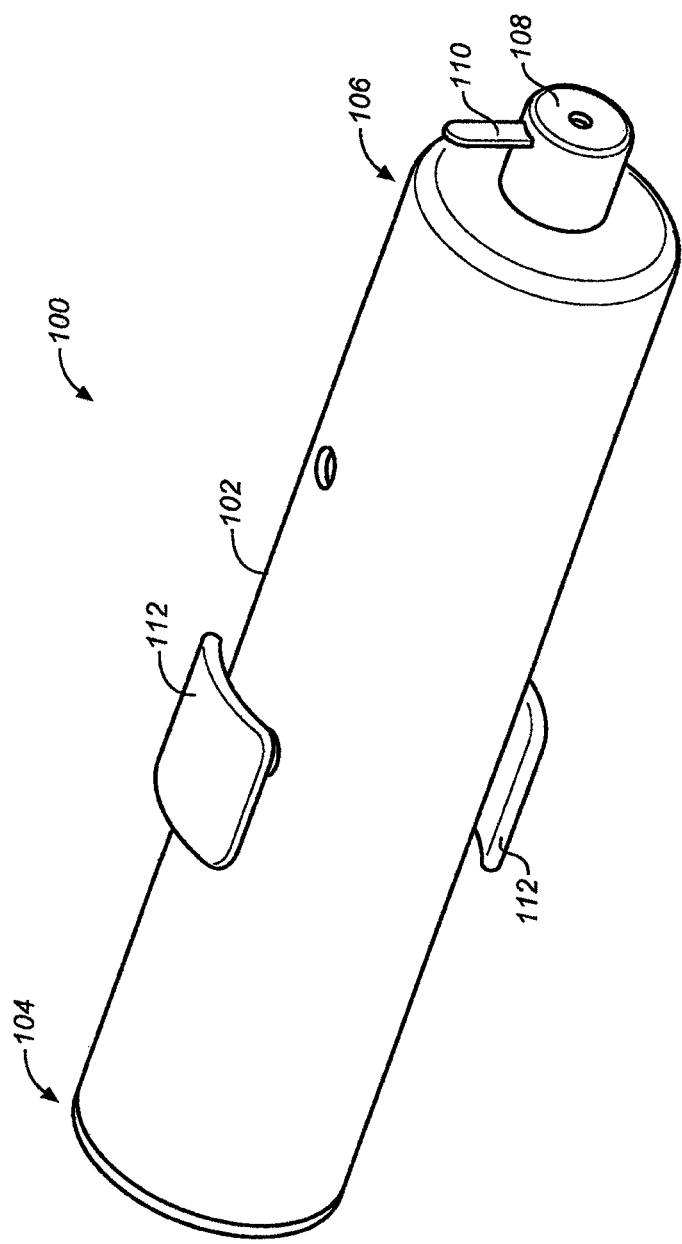
FIG. 28 depicts a perspective view of a device including a further example of a two-spring actuation mechanism in its pre-activated state.

FIG. 28 also depicts an exemplary integrated intraocular drug delivery device with a two-spring actuation mechanism. In FIG. 28, the device (100) includes a housing (102) having a proximal end (104) and a distal end (106). An ocular contact surface (108) is attached to the distal end (106). A measuring component (110) is attached to one side of the ocular contact surface (108). As further described below, a trigger (112) that is operatively coupled to the housing (102) works with the first spring (114) and the second spring (116) of the actuation mechanism to deploy pins (118) through openings (120) in the housing (102), to thereby deliver drug from the reservoir (122). First spring (114), second spring (116), pins (118), openings (120), and reservoir (122) are better shown in FIG. 29. Also in FIG. 29, a conduit, e.g., needle (124), is depicted within the housing in its first non-deployed state. Needle (124) is configured as being part of an assembly (125) such that movement of the assembly results in corresponding movement of the needle (124). A stop (115) is provided at the proximal end (127) of the assembly (125), which is connected to the distal end of the first spring (114) and the proximal end of the second spring (116). The springs, as well as other components of the device may be connected via medical grade adhesives, friction or snap fit, etc.

In FIG. 30, the second spring (116) is operatively connected to a plunger (132) by friction fit within a compartment (134) of the plunger (132). In the pre-activated state, as shown in FIG. 29, the plunger (132) and second spring (116) are held in place by pins (118). The pins (118) are removably engaged to the plunger (132) at plunger groove (138), and lock the plunger (132) in place via friction fit against the plunger groove (138) and housing (102).

Figure 31B:
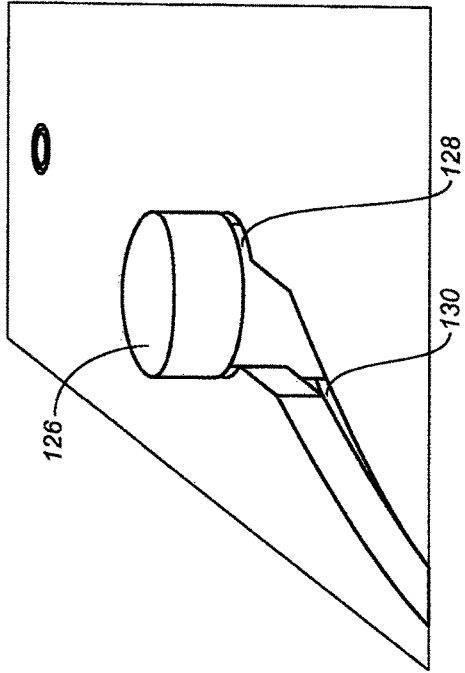
FIGS. 31A-31C illustrate how the trigger in FIG. 28 actuates the first spring of the two-spring actuation mechanism to deploy the conduit.
Figure 31A:
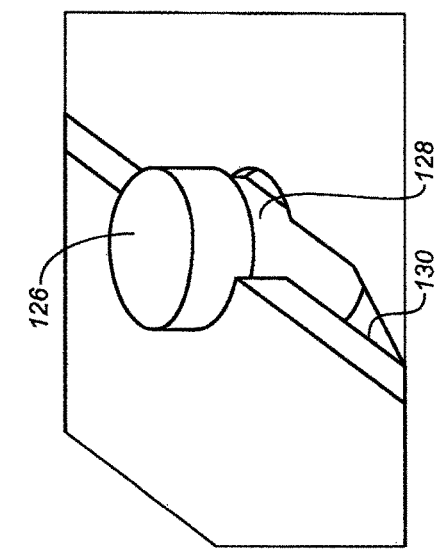
Figure 31C:
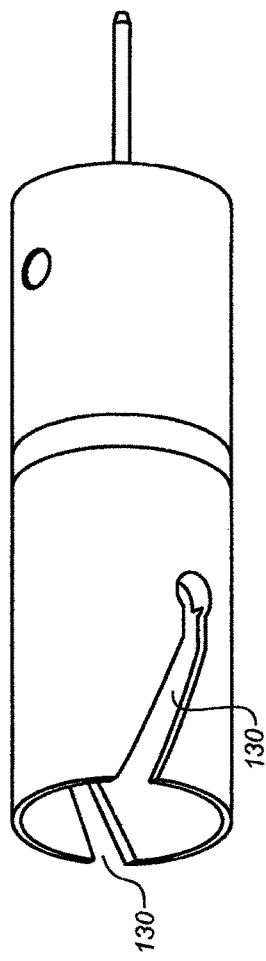

Activation of the first spring (114) of the actuation mechanism by activating the trigger deploys the needle (124) into the intraocular space, i.e., it moves the needle (124) from its first non-deployed state (FIG. 29) to its second deployed state (FIG. 30). Referring to FIGS. 30 and 31A-31C, activation of the first spring (114) occurs by depression of trigger (112) by, e.g., one or two fingers, which also depresses buttons (126). As shown in FIGS. 31A and 31B, buttons (126) are configured with a button groove (128) that allows the buttons (126) to align with channels (130) in the housing (102). Once aligned with the channels (130), the buttons (126) may be slidingly advanced along the channels (130). The channels may be of any suitable length. The distance from the distal end of the channel to the distal end of the housing may range from about 10 to about 20 mm. In one variation, the distance from the distal end of the channel to the distal end of the housing is about 16 mm. The rate of movement along the channels (130) may be controlled manually by the user, automatically controlled by the force of spring expansion, or a combination of both. This movement of the buttons (126) allows expansion of the first spring (114) against stop (115) so that the needle assembly (125) and needle (124) can be deployed. The channels in the housing may have any suitable configuration. For example, as shown in FIG. 31C, the channels (130) may be spiral cut within the housing to allow rotation or a corkscrew type movement of the needle upon advancement, which may facilitate needle penetration through the eye wall.

Figure 32A:
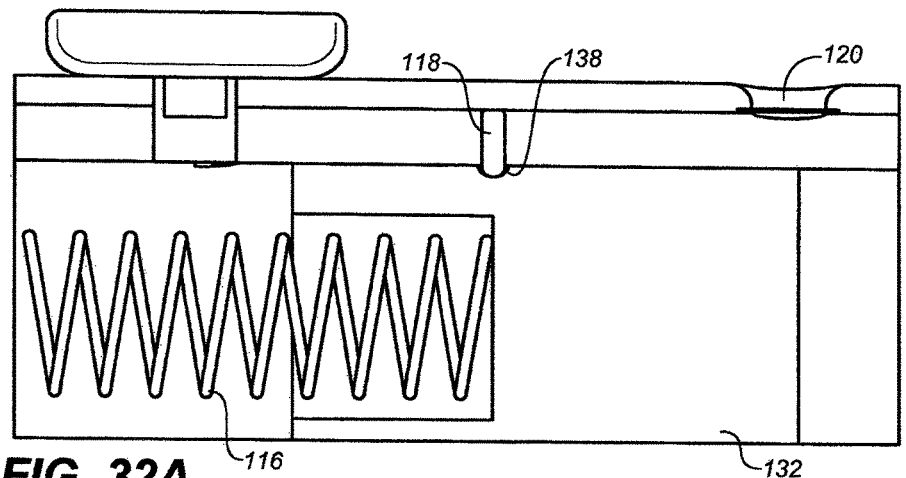
FIGS. 32A-32C are expanded views that illustrate how release of the locking pins in FIG. 28 work to activate the second spring of the two-spring actuation mechanism.
Figure 32B:
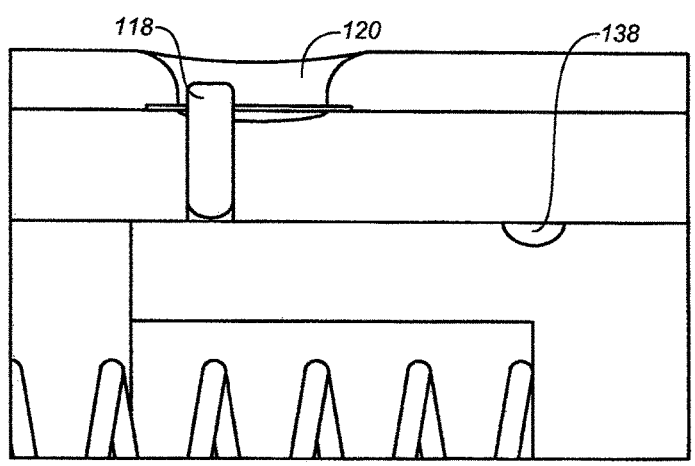
Figure 32C:
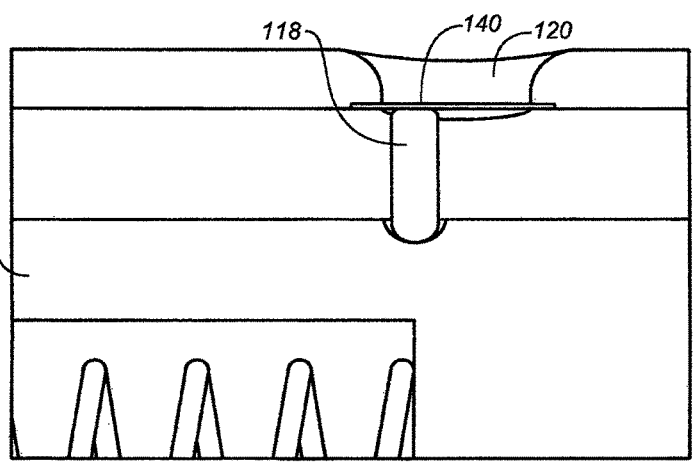

Activation of the first spring (114) will typically result in activation of the second spring (116) to deliver drug out of the device and into the intraocular space. For example, as shown in FIG. 30, the expansion force of first spring (114) against stop (115) that is also connected to the proximal end of the second spring (116) works to expand the second spring (116) so that the assembly (125) is advanced within the housing (102). As illustrated in FIGS. 32A-32C, when the pins (118) that are removably engaged to plunger (132) reach openings (120), they are deployed out through the openings (120). Expulsion of the pins (118) from the device, then allows free expansion of the second spring (116) against plunger (132), to thereby push drug residing with reservoir (122) out of the device. The openings (120) may be covered by a membrane or seal (140) that can be penetrated by the pins (118) to give a visual indication that the drug has been delivered.

A two-spring actuation mechanism, as shown in FIGS. 41A-41B may also be used. Referring to FIG. 41A, integrated device (600) includes an actuation mechanism comprising a first spring (602) and a second spring (604). In use, when trigger (606), e.g., a lever, is depressed, first spring (602) is released to advance shaft (608) in the direction of the arrow, which in turn advances needle (610) out of the tip of the device (600). Continued advancement of the shaft (608) advances the injection sleeve (612) and top seal (614) so that drug within reservoir (616) may be delivered through needle (610). Referring to FIG. 41 B, once the drug has been injected, tabs (618) removably engage housing openings (620) to thereby release second spring (604), which then moves shaft (608) backward to retract needle (610) (not shown).

Figure 36:
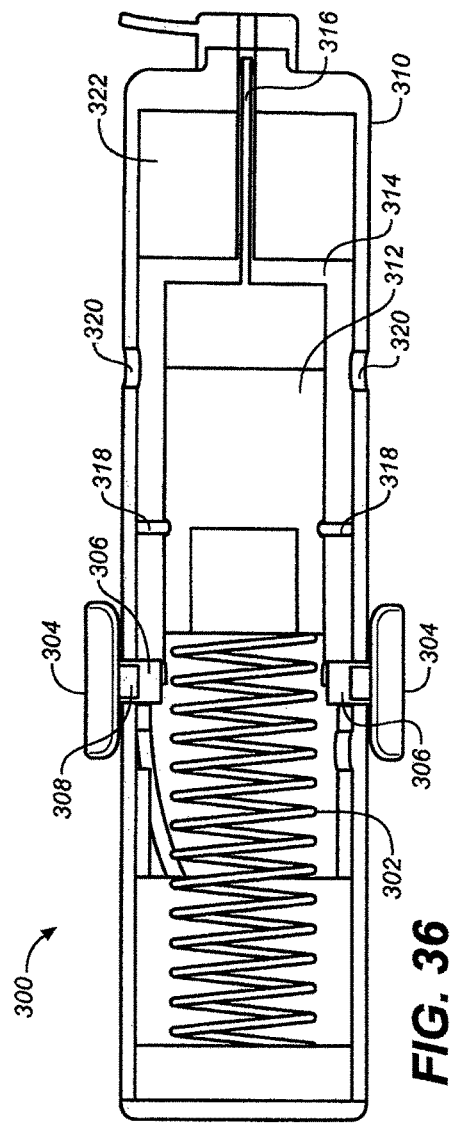
FIG. 36 is a cross-sectional view of an exemplary device including a single spring actuation mechanism.
Figure 37:
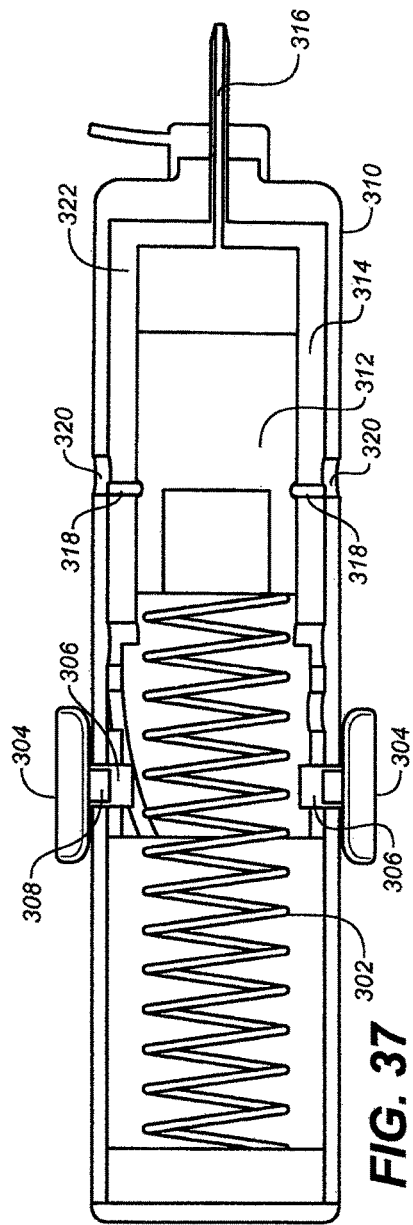
FIG. 37 is a cross-sectional view of the device shown in FIG. 36 that showing the single spring actuation mechanism after deployment of the conduit.

In some variations, a single-spring actuation mechanism is employed, as shown in FIGS. 36 and 37. When a single spring is used, the actuation mechanism is configured much like the two-spring mechanism described above except that the second spring is removed. Thus, in its pre-activated state, as shown in FIG. 36, a device (300) with a single spring (302) may activate the single spring (302) by depression of trigger (304) by, e.g., one or two fingers, which also depresses buttons (306). The buttons (306) are configured with a button groove (308) that allows the buttons (306) to align with channels (not shown) in the housing (310). Once aligned with the channels, the buttons (306) may be slidingly advanced along the channels. This movement of the buttons (306) allows expansion of the spring (302) against plunger (312) so that the needle assembly (314) and needle (316) can be deployed. When the pins (318) that are removably engaged to plunger (312) reach openings (320) within the housing (310), they are deployed out through the openings (320). Expulsion of the pins (318) from the device, then allows further expansion of the spring (302) against plunger (312), to thereby push drug residing with reservoir (322) out of the device. Although not shown here, the openings (320) may be covered by a membrane or seal that can be penetrated by the pins (318) to give a visual indication that the drug has been delivered.

Figure 34:
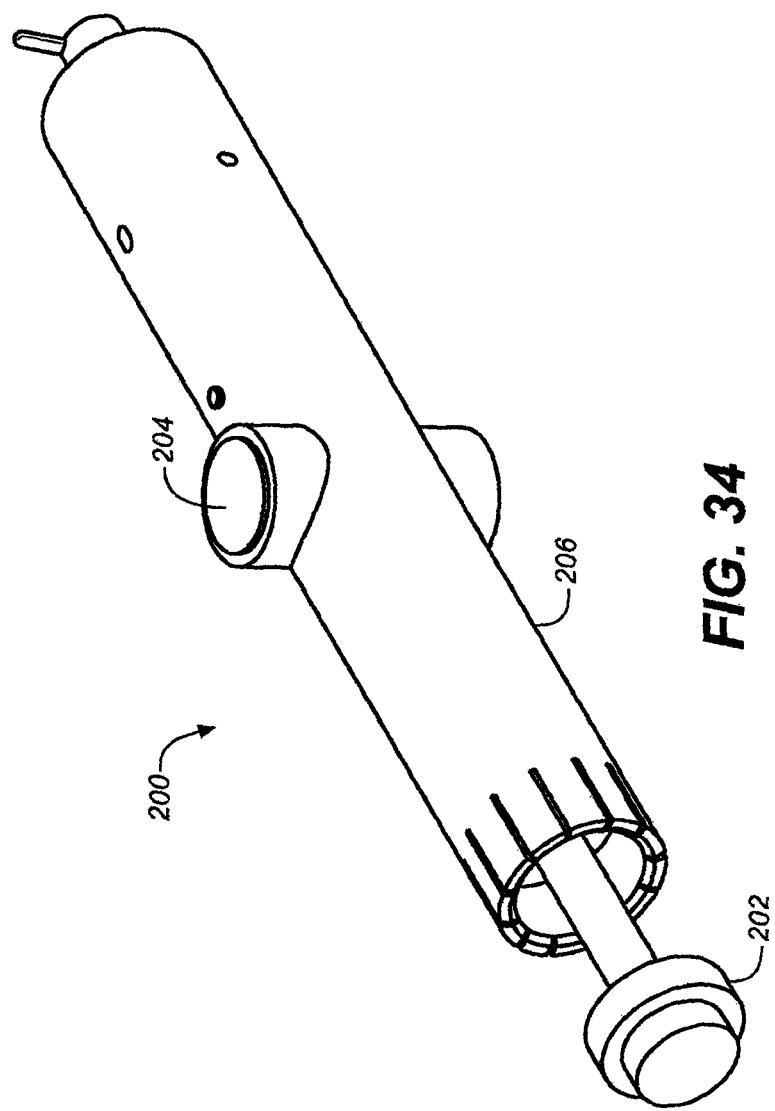
FIG. 34 is a perspective view of an exemplary device with a pneumatic actuation mechanism.

A pneumatic actuation mechanism may also be employed. In one variation, as depicted in FIGS. 34 and 35A and 35B, the pneumatic actuation mechanism includes a plunger, pins, and housing openings in the same fashion as described for the single- and two-spring mechanisms. However, instead of using a spring to deploy the needle assembly and plunger, a piston is used to slidingly advance the needle assembly within the housing. For example, in FIG. 34, a device with a pneumatic actuation mechanism (200) includes a piston (202) and trigger (204). The piston (202) is used to compress air into the housing (206) of the device (202). If desired, the amount of compressed air the piston includes in the device may be controlled by a dial or other mechanism (not shown). The proximal end of the housing may also be configured, e.g., with a flange, crimps, or other containment structure, that allows translational movement of the piston (202) into the housing but not out of the housing. Upon depression of a trigger (208), a pair of locking pins (210) are also depressed to thereby allow the compressed air generated by the piston (202) to push the needle assembly (212) forward. This advancement of the needle assembly (212) deploys the needle (214) out of the device (FIG. 35B). As previously stated, pins (216) similar to those above that lock the plunger (218) in place are also provided. Upon their expulsion from the device out of openings (220) in the housing (206) due to forward movement of the needle assembly (212), the compressed air further moves the plunger (218) forward to thereby push drug residing with reservoir (222) out of the device. Rotational pins (224) may also be included, which upon release by the sliding needle assembly (212) allow rotation of the needle assembly (212) with respect to the housing (206).

As previously stated, a trigger may be coupled to the housing and configured to activate the actuation mechanism. In one variation, the trigger is located on the side of the device housing proximate the device tip at the ocular interface surface (e.g., the distance between the trigger and device tip may range between 5 mm to 50 mm, between 10 mm to 25 mm, or between 15 mm to 20 mm), so that the trigger can be activated by a fingertip while the device is positioned over the desired ocular surface site with the fingers on the same hand. In another variation, the trigger is located on the side of the device housing at 90 degrees to the measuring component, so that when the ocular contact surface is placed on the eye surface perpendicular to the limbus, the trigger can be activated with the tip of the second or third finger of the same hand that positions the device on the ocular surface.

Some variations of the device may include a control lever for initiating plunger movement. In these instances, the control lever may actuate the plunger in a mechanical manner, e.g., by spring-actuation, similar to that described above. In other variations, actuation of the plunger may occur through a combination of mechanical and manual features. For example, the initiation of plunger movement may be aided by a manual force applied onto the control lever, while a spring-actuated mechanism for generating a mechanical force is also employed to move the plunger forward inside the device barrel to inject drug. In instances where the control lever is connected to the plunger, the initiation of plunger movement and drug injection is controlled by the manual component, whereas the rate of fluid injection is controlled by the mechanical force. Here a reduced manual force may be applied to the plunger due to its combination with a co-directional mechanical force, thus facilitating the stability of device positioning on the ocular surface at a precise injection site.

The control lever may be placed between 10 mm and 50 mm from the tip of the device that interfaces with the eye surface, or between 20 mm and 40 mm from the tip of the device. Positioning of the control lever in this manner may enable atraumatic and precise operation of the device with one hand.

Figure 43A:
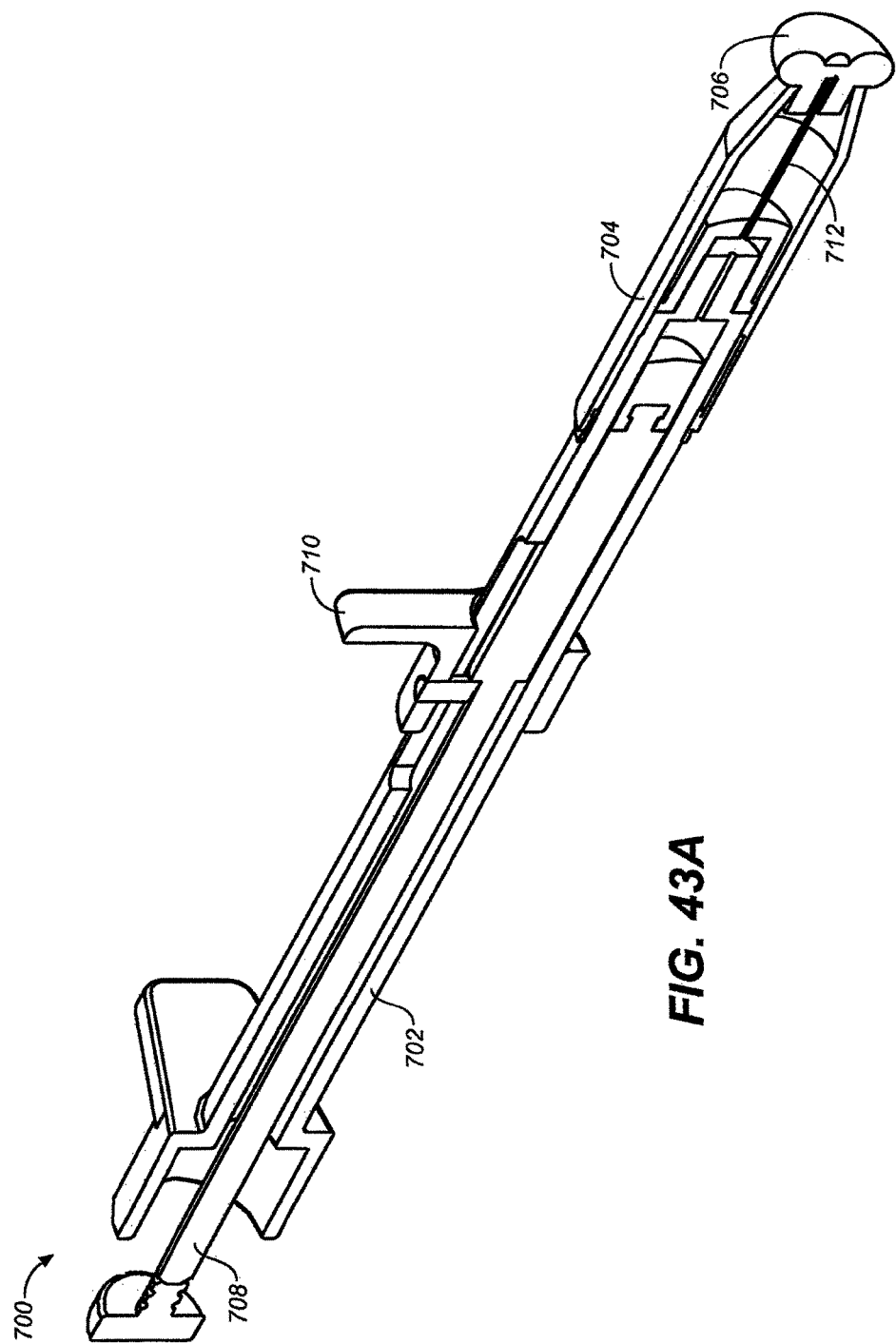
FIGS. 43A-43D illustrate an exemplary method of advancement of a dispensing member and drug injection.
Figure 43B:
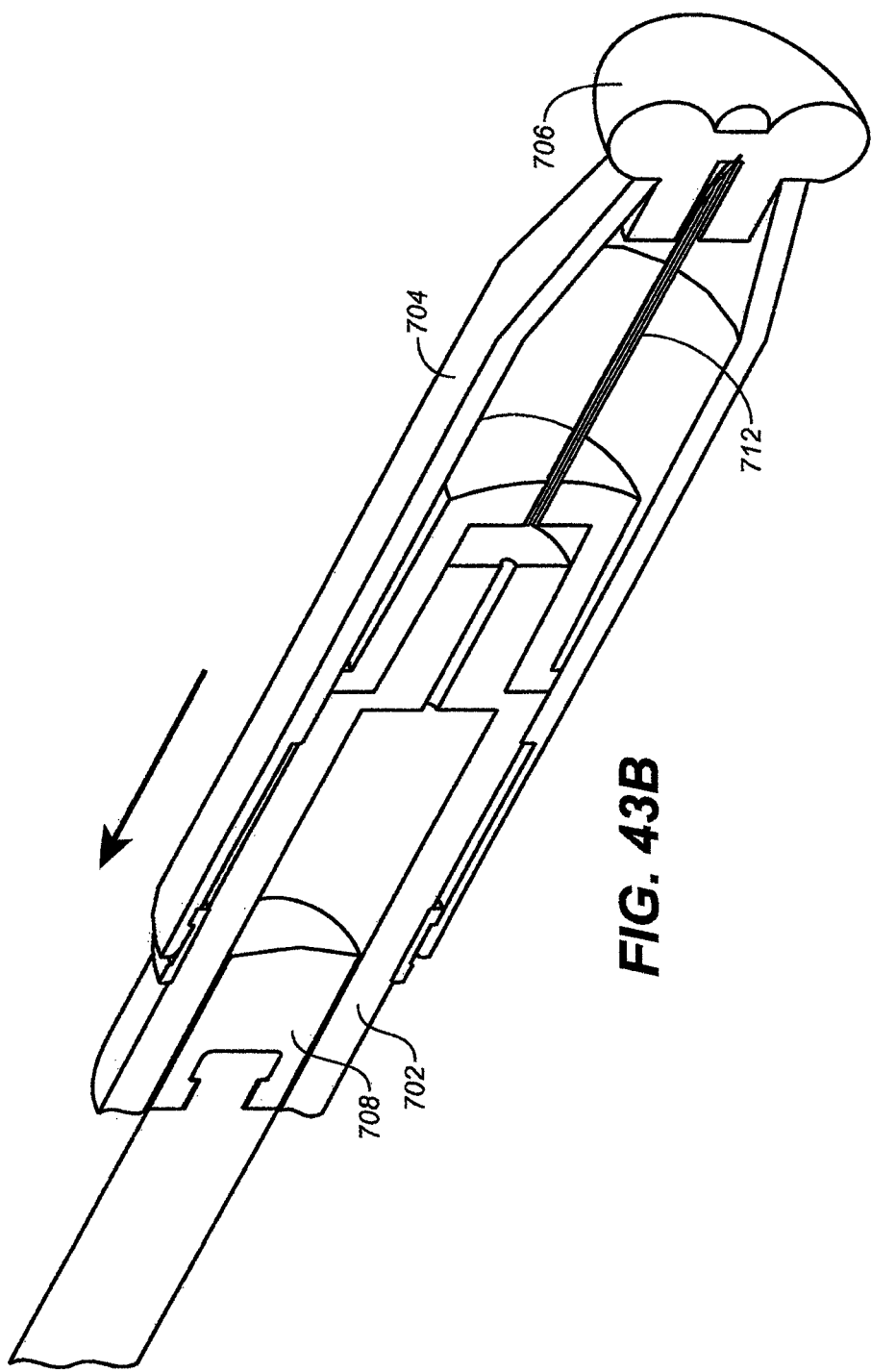
Figure 43C:
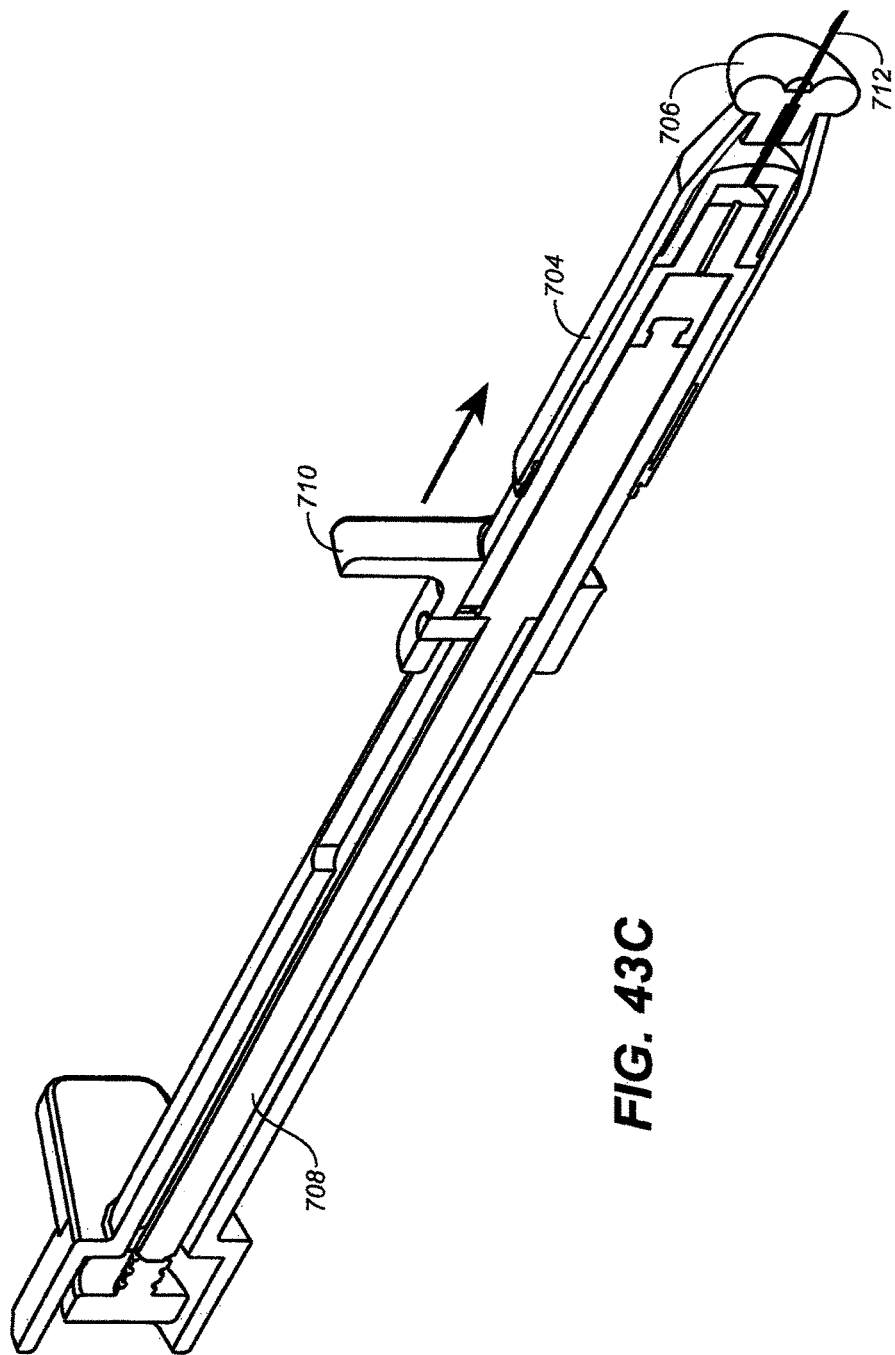
Figure 43D:
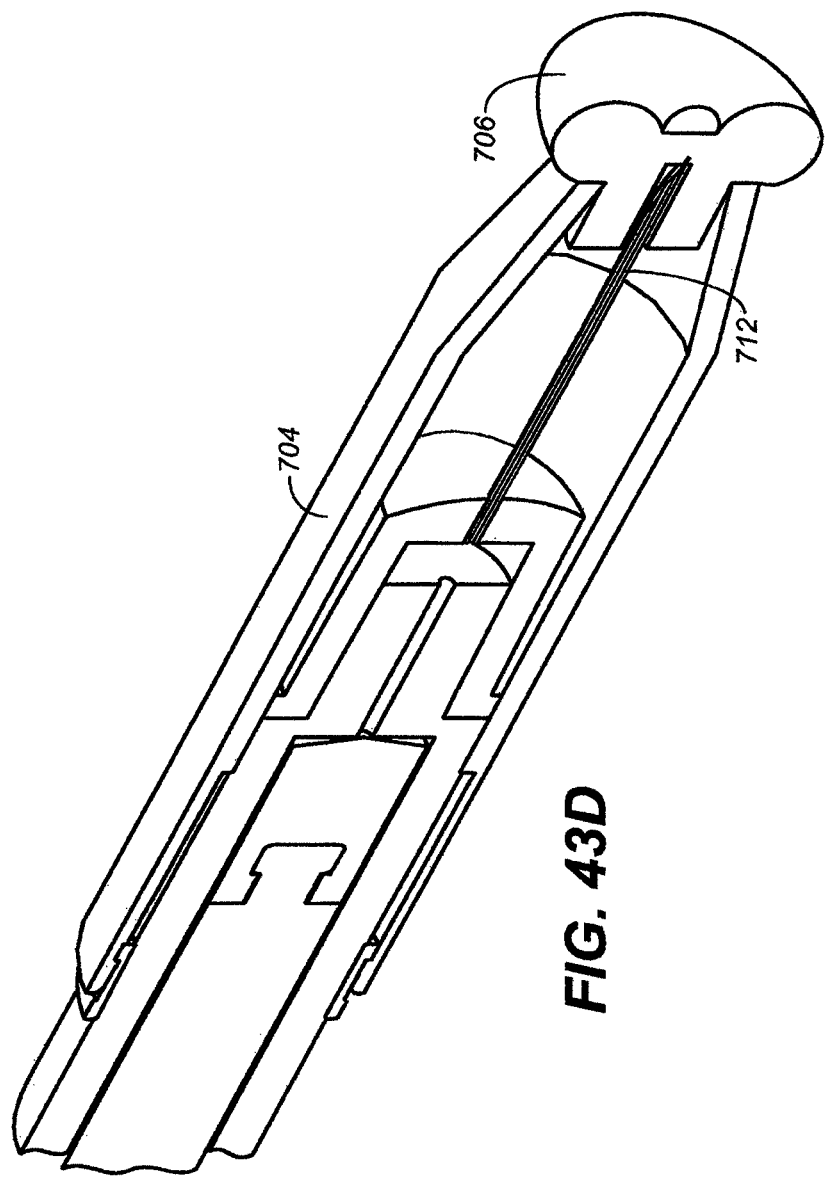

As illustrated in FIGS. 43A-43D, exemplary integrated device (700) includes a housing (702), a dynamic sleeve (704) slidable thereon, an ocular contact surface (706), a plunger (708), and a control lever (710) for manually actuating the plunger (708) to inject drug through needle (712). An expanded sectional view of the ocular contact surface (706), dynamic sleeve (706), plunger (708), and needle (712) shown in FIG. 43 A is shown in FIG. 43B. In use, after placing the ocular contact surface (706) on the eye, the applied pressure may automatically slide the dynamic sleeve (704) back (in the direction of the arrow) to expose the needle and allow needle penetration through the eye wall. The control lever (710) may then be slidably advanced manually (in the direction of the arrow in FIG. 43C) to advance plunger (708). When injection of the drug through the needle (712) is complete, the dynamic sleeve (704) may be slidably advanced manually to cover the needle, as shown in FIG. 43D.

The dynamic sleeve may be slidably advanced or retracted manually by a fine mobility control mechanism, also referred to as a mobility control mechanism. In these instances, the dynamic sleeve may comprise a high-traction surface located on the outer surface of the sleeve, which may aid movement of the sleeve with a fingertip. In one variation, the high-traction surface may be engraved or contain markings with a serrated pattern. In other variations, as shown in FIG. 45A, a platform or pad (e.g., a fingertip pad) (900) may be attached to the outer surface of the sleeve (902) to help manually advance or retract the sleeve. The platform or pad may also include a high-traction surface (904), the perspective, side, and top views of which are illustrated in FIGS. 45B, 45C, and 45D, respectively. Platform or pad (900) will typically include a base (912) for attachment to the sleeve (902). Base (912) may be of any suitable configuration. For example, the base of the platform or pad may be configured as a cylinder (FIG. 45H) or with a narrowed portion (portion of lesser diameter), such as a dumbbell or apple core shape (FIG. 45I). In yet further variations, the fine mobility control mechanism is configured as raised, circular flange located at or near the proximal edge of the dynamic sleeve. In one example, the circular flange is raised about 1 mm to about 1.5 mm over the outer surface of the dynamic sleeve, so that the operator has a tactile feel of its surface, and is able to control movement of the sleeve when applying a retractive (pulling) or pushing force to it.

Figure 45E:
Figure 45F:

Some variations of the devices described herein include a grip having a retraction slot or channel that works in combination with the dynamic resistance component to inject drug into the eye. Referring to FIG. 45 A, grip (906) may be a component coupled (usually fixedly attached) to the device housing (908) at the proximal end (912) of the sleeve (902). The grip (906) may be configured to include a retraction slot (910) in its wall. In use, when the sleeve (902) is retracted, as shown by the direction of the arrow in FIG. 45J, the base (912) of the pad or platform is moved into the slot (910). The retraction slot (910) may be configured as a channel of uniform width (FIG. 45F), or as a channel with a keyhole-type configuration, e.g., having a narrowed portion (FIG. 45G) or enlarged portion (FIG. 45E) at the slot proximal or distal end. The retraction slot may provide sensory feedback, e.g., when the endpoint of retraction is reached. The configuration of the base of the platform or pad may be chosen so that it provides a friction fit with the slot. For example, when the slot has a narrowed portion, the base may also have a narrowed portion.

When grips are employed, the devices may also include a locking mechanism. In one variation, when the end point of the sleeve retraction and needle exposure/deployment is reached, the wide portion of the sleeve slot is aligned with the wide portion of a grip slot and with an opening in the housing and an opening in the plunger shaft, allowing the platform base to be inserted into the plunger shaft to lock it relative to the platform that become an actuation lever for manual drug injection. The narrow part of the base enters the narrow part of the sleeve slot, which unlocks the platform relative to the sleeve allowing its movement towards device tip. In another variation, when the platform base reaches the end point of the retraction slot, it may be depressed into an opening in the plunger shaft and becomes a locking pin to connect the platform and the plunger. When it is depressed, its narrow portion enters the keyhole-shaped slot in the sleeve, and becomes movable within the slot moving towards the tip of the sleeve (unlocks the platform base and sleeve).

The mobility control mechanism may be beneficial when the user desires to control the amount of pressure exerted by the device tip on the eye surface in order to deploy the needle during its intraocular penetration. With a mobility control mechanism, the user may use a fingertip to either reduce or increase counter-forces that regulate the sleeve movement and needle exposure.

For example, if the user exerts the pulling force onto the said high-traction surface (that is pulling the high-traction surface of the sleeve away from the device tip), this movement may facilitate needle exposure and reduce the amount of pressure force (down to 0 Newton) needed to be applied to the eye wall in order to slide the sleeve back and expose the needle. In another variation, if the user exerts a pushing force (that is pushing the high-traction surface of the sleeve towards the device tip), this movement may counteract and impedes needle exposure, which may allow the device tip to apply increased pressure to the eye wall prior to the initiation of sleeve movement and needle exposure.

In use, the platform or pad may be slid with a second or third finger. Again, this allows the injector to manually modulate the sleeve resistance and movement along the device tip. For example, by pushing the pad and thus the sleeve forward with a fingertip, the injector provides some resistance at the beginning of the procedure when the device tip is being positioned on the eye surface (and the needle needs to remain completely covered). Then the injector would release his/her fingertip from the sleeve pad to enable needle deployment and its transscleral penetration. Some variations of the device may also include a step or a ring-shaped ridge at the end of the sleeve path, so that after the sleeve is pulled back past this step, it would automatically trigger spring-actuated plunger movement. The fingertip pad could be used to pull the sleeve back past the said step at the end of needle deployment in order to actuate the plunger movement and drug injection.

When a platform or pad is employed, it may reduce the amount of pressure the device exerts on the eyeball before the sleeve begins to move to expose the needle, and thus, allow customization of the amount of applied pressure from patient to patient.

In another aspect, the dynamic sleeve may provide gradual needle exposure as it penetrates through the eye wall so that the needle is exposed 1 mm or less when it meets most resistance at the eye surface. Here the rest of the needle is located inside the sleeve with at least its most distal unexposed point or a longer segment being protected inside the narrow exit orifice or canal. Such sleeve design may minimize the risk of needle bending compared to the conventional syringe with a long exposed needle. This design may enable the utilization of smaller a gauge needle without increased risk of it being bent as it penetrated through the eye wall. The smaller needle gauge may render it more comfortable and less traumatic during its intraocular penetration.

Some variations of the devices described here may comprise an endpoint shock absorber. The endpoint shock absorber may be a component that cushions the eye against the force transmitted by the dynamic sleeve and the needle when they come to an abrupt stop. The transmitted force wave may be harmful for the delicate structures inside the eye such as the lens, retina and the choroidal vasculature. Inclusion of an endpoint shock absorber may allow the needle to come to a soft and gradual stop at the end of its deployment path when it is fully extended through the eye wall into the intraocular cavity. In one variation, the shock absorber is provided as a tapered surface at the distal end or distal portion of the dynamic sleeve. In another variation, the shock absorber is a soft sleeve located at the base of the drug conduit (such as at the hub of an injection needle). Here the soft sleeve may be configured to contact the tip of the device when the needle is fully deployed. In yet another variation, the shock absorber is the soft tip of the device, where the soft tip is configured to contact the hub of the needle when the needle is fully deployed. Exemplary materials suitable to make the endpoint shock absorbers include without limitation, methylmethacrylate (MMA); polymethylmethacrylate (PMMA); polyethylmethacrylate (PEM) and other acrylic-based polymers; polyolefins such as polypropylene and polyethylene, vinyl acetates, polyvinylchlorides, polyurethanes, polyvinylpyrollidones, 2-pyrrolidones, polyacrylonitrile butadiene, polycarbonates, polyamides, fluoropolymers such as polytetrafluoroethylene (e.g., TEFLON™ polymer); polystyrenes; styrene acrylonitriles; cellulose acetate; acrylonitrile butadiene styrene; polymethylpentene; polysulfones; polyesters; polyimides; natural rubber; polyisobutylene rubber; polymethylstyrene; silicone; and derivatives, copolymers and blends thereof.

The devices described herein may also include a visual feedback mechanism configured to allow the operator to precisely determine when the needle has been deployed to the desired extent, and to safely initiate drug injection. Furthermore, during the needle deployment process, the eyes of the operator should be pointed at the device tip-eye interface. Thus, it would be beneficial for the visual feedback mechanism to be located in close proximity to the device tip-eye interface, so as not to distract the operator from closely monitoring the device position during the entire intraocular drug delivery procedure. With such a configuration, the operator does not have to take his/her eyes off of the device-ocular interface during the entire injection procedure, minimizing the risk of accidental trauma during unexpected movement of the eye or head of the subject. In some variations, the visual feedback mechanism may be coupled to a mechanical stopper at the end-point of the needle deployment process. Here the visual feedback mechanism may be configured as an elongated measuring tip band, where the tip comes up to a stop against the needle base or hub, which determines the end-point of needle deployment when the sleeve has been fully retracted. Another example of the visual feedback mechanism is a band or a spacer placed on the needle base, so that the band comes up to a stop against the inside surface of the tip, which determines the end-point of needle deployment when the sleeve has been fully retracted.

Figure 48:
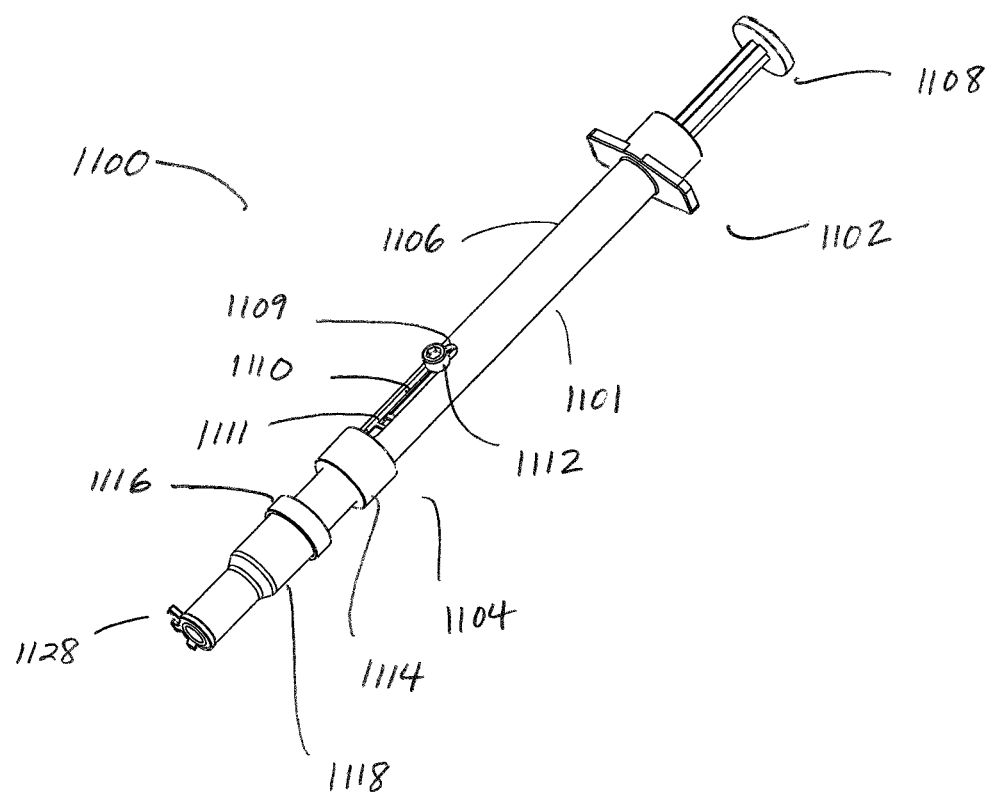
FIG. 48 shows a perspective view of one variation of an intraocular injection device.

The devices described herein may be integrated or non-integrated. An exemplary injection device is shown in FIG. 48. In the figure, injection device (1100) comprises a housing (1101) having a wall (1106), a proximal end (1102), a distal end (1104), and a lumen (not shown) extending between the proximal end (1102) and distal end (1104). A plunger (1108) is slidable at least partially through the lumen. A longitudinally extending channel (1110) having a proximal end (1109) and a distal end (1111) formed through the wall (1106) is provided at the device distal end (1104). A plunger actuation lever such as knob (1112) is configured so that slidable advancement of the knob (1112) from the channel proximal end (1109) to the channel distal end (1111) also slidably advances the plunger (1108) to deliver medication into the eye. The channels may be of any suitable length. The distance from the distal end of the channel (1111) to the distal end of the housing (1104) may range from about 10 to about 20 mm. In FIG. 48, the distance from the distal end of the channel (1111) to the distal end of the housing (1104) is about 16 mm. The injection device of FIG. 48 also includes a cover or sleeve (1114) that overlays an opening or aperture in the housing wall (not shown) through which a drug loader (as previously described) may be placed. The drug loader would deliver medication from a drug vial to the reservoir of the device. The cover or sleeve (1114) may partially, substantially or entirely surround the housing and be made from materials such as rubber or silicone. The drug loader may puncture the cover or sleeve and extend through the opening or aperture of the housing so that medication can be filled into the reservoir.

Figure 49A:
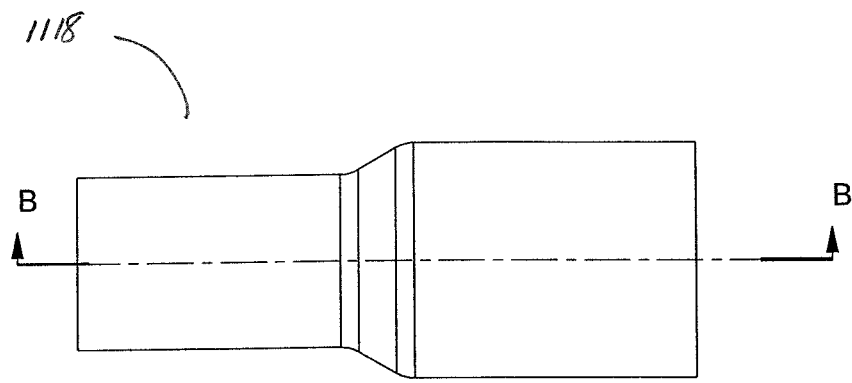
FIGS. 49A and 49B are expanded views of the exemplary dynamic sleeve shown in FIG. 48.
Figure 49B:
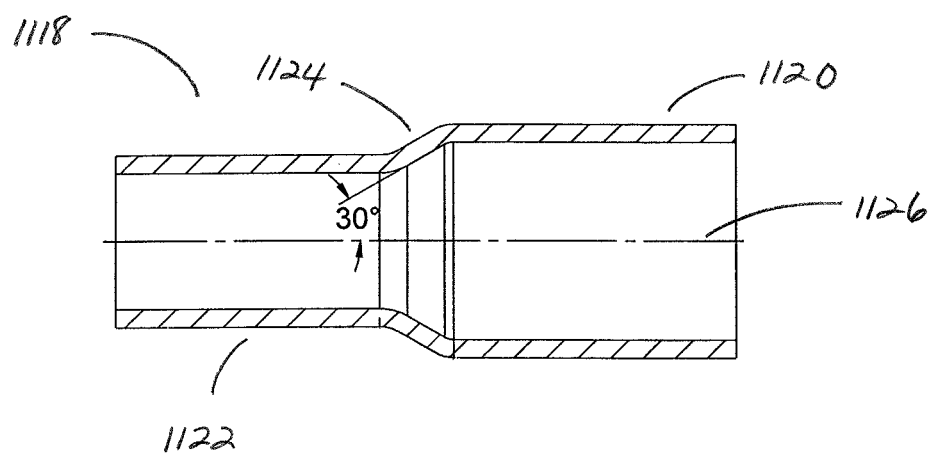

In FIG. 48, the injection device also includes a flange (1116). As previously described, flange (1116) may be part of a fine mobility control mechanism. The flange (1116) may be configured as a raised, circular flange located at or near the proximal edge of a dynamic sleeve (1118). As shown in more detail in FIG. 49B, dynamic sleeve (1118) has a first section (1120) and a second section (1122). The inner diameter of first section (1120) will typically be greater than the inner diameter of second section (1122). For example, the inner diameter of the first section may be about 7.0 mm and the inner diameter of the second section may be about 4.8 mm. The length of the first and second sections may also vary. In FIG. 49B, the length of the first section (1120) may be about 9.0 to 10 mm and the length of the second section (1122) may be about 9.0 to 10 mm. A ramped portion (1124) may also connect the first and second portions (1120 and 1122). Ramped portion (1124) may be configured so that an angle is created with the longitudinal axis (1126) of the device, e.g., an angle of 30 degrees as shown in FIG. 49B.

Figure 50:
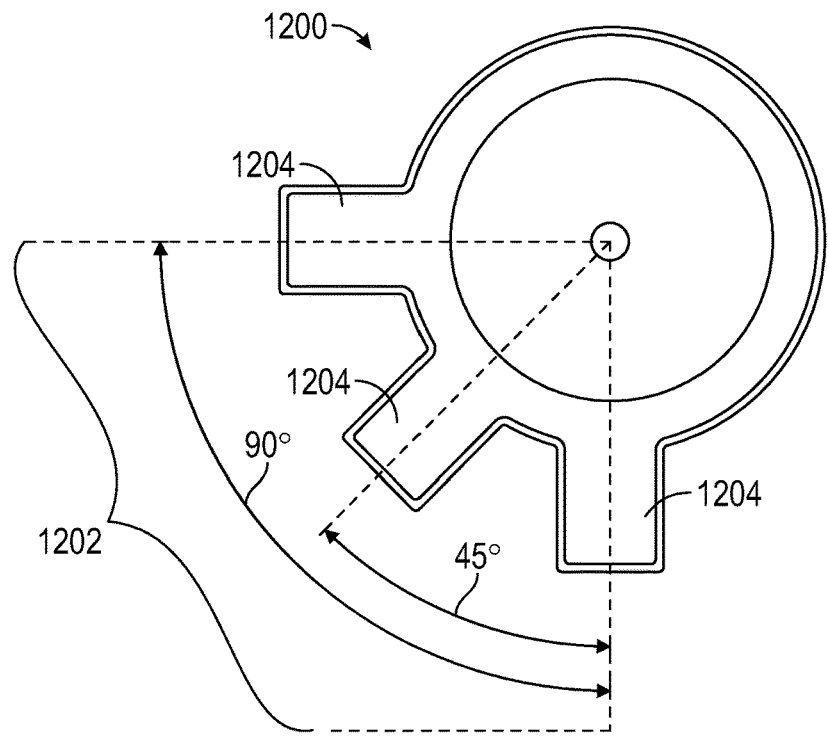
FIG. 50 is an expanded end view of the sectoral measuring component shown in FIG. 48.
Figure 51:
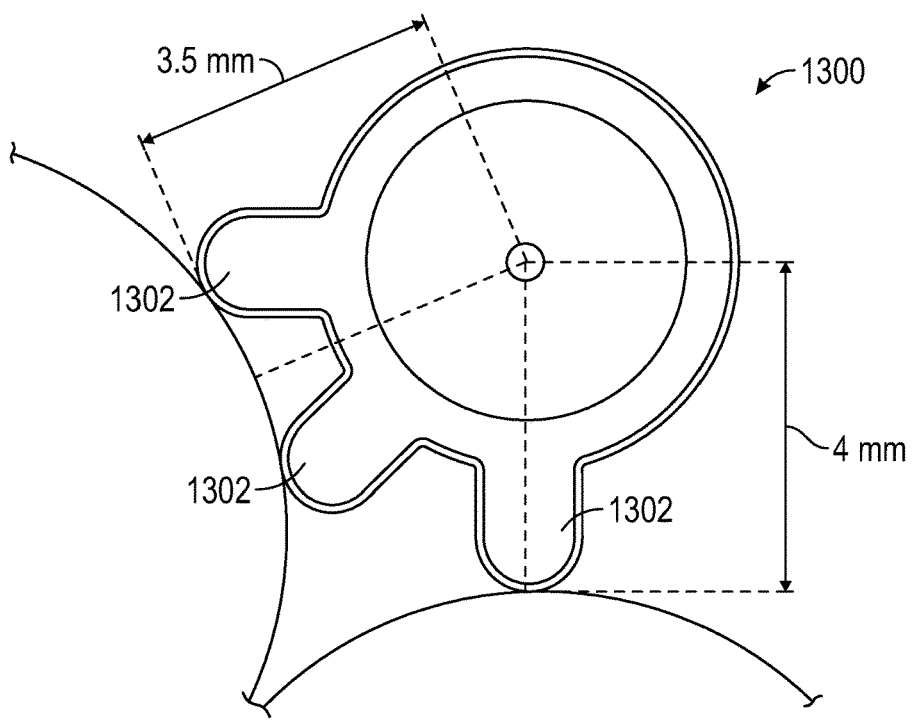
FIG. 51 depicts a sectoral measuring component according to another variation on the surface of the eye at the corneo-scleral limbus.

The injection device of FIG. 48 also includes a sectoral measuring component (1128). The sectoral measuring component in this as well as other variations has a circumference (that spans 360 degrees) and a longitudinal axis. Radially extending members such as tabs or spokes may be provided around the circumference of the sectoral measuring component in any suitable manner, e.g., equidistant from each other, symmetrically or asymmetrically spaced around the circumference, but typically in a manner that avoids contact with the eyelid(s) and eyelashes to maintain its sterility. Thus, the radially extending members will generally be provided on a section (portion) of the circumference and will generally span a certain number of degrees of arc around the circumference. For example, and as specifically shown in FIG. 50, sectoral measuring component (1200) has a section (1202) having three radially extending members (1204). The section (1202) spans an area (e.g., arc) around the circumference of 90 degrees. In this configuration, the radially extending members are spaced around the circumference 45 degrees apart from each other. In another variation, as shown in FIG. 51, sectoral measuring component (1300) is configured similarly to that illustrated in FIG. 50 except that the distal ends of the radially extending members (1302) are rounded.

II. METHODS

Methods for using the integrated intraocular drug delivery devices are also described herein. In general, the methods include the steps of positioning an ocular contact surface of the device on the surface of an eye, applying pressure against the surface of the eye at a target injection site using the ocular contact surface, and delivering an active agent from the reservoir of the device into the eye by activating an actuation mechanism. The steps of positioning, applying, and delivering are typically completed with one hand.

The application of pressure against the surface of the eye using the ocular contact surface may also be used to generate an intraocular pressure ranging between 15 mm Hg to 120 mm Hg, between 20 mm Hg to 90 mm Hg, or between 25 mm Hg to 60 mm Hg. As previously stated, the generation of intraocular pressure before deployment of the dispensing member (conduit) may reduce scleral pliability, which in turn may facilitate the penetration of the conduit through the sclera, decrease any unpleasant sensation on the eye surface during an injection procedure, and/or prevent backlash of the device. Intraocular pressure control may be generated or maintained manually or automatically using pressure relief valves, pressure sensors, pressure accumulators, pressure sensors, or components such as slidable caps having locking mechanisms and/or ridges as previously described.

Use of the devices according to the described methods may reduce pain associated with needle penetration through the various covers of the eye wall such as the conjunctiva that is richly innervated with pain nerve endings. The anesthetic effect at the injection site during an intraocular injection procedure may be provided by applying mechanical pressure on the conjunctiva and the eye wall over the injection site before and/or during the needle injection. The application of mechanical pressure to the eye wall may also transiently increase intraocular pressure and increase firmness of the eye wall (and decrease its elasticity), thereby facilitating needle penetration through the sclera. Furthermore, the application of mechanical pressure to the eye wall may displace intraocular fluid within the eye to create a potential space for the drug injected by the device.

The devices may be used to treat any suitable ocular condition. Exemplary ocular conditions include without limitation, any type of retinal or macular edema as well as diseases associated with retinal or macular edema, e.g., age-related macular degeneration, diabetic macular edema, cystoid macular edema, and post-operative macular edema; retinal vascular occlusive diseases such as CRVO (central retinal vein occlusion), BRVO (branch retinal vein occlusion), CRAO (central retinal artery occlusion), BRAO (branch retinal artery occlusion), and ROP (retinopathy of prematurity), neovascular glaucoma; uveitis; central serous chorioretinopathy; and diabetic retinopathy.

When dexamethasone sodium phosphate solution is used to treat an ocular condition, the dose of dexamethasone sodium phosphate that may be administered into the eye by each individual injection device may range between about 0.05 mg and about 5.0 mg, between about 0.1 mg and about 2.0 mg, or between about 0.4 mg and about 1.2 mg.

In some variations, a topical anesthetic agent is applied on the ocular surface before placement of the device on the eye. Any suitable topical anesthetic agent may be used. Exemplary topical anesthetic agents include without limitation, lidocaine, proparacaine, prilocaine, tetracaine, betacaine, benzocaine, bupivacaine, ELA-Max®, EMLA® (eutectic mixture of local anesthetics), and combinations thereof. In one variation, the topical anesthetic agent comprises lidocaine. When lidocaine is used, it may be provided in a concentration raging from about 1% to about 10%, from about 1.5% to about 7%, or from about 2% to about 5%. In another variation, the topical anesthetic agent is mixed with phenylephrine or another agent that potentiates or/and prolongs the anesthetic effect of the pharmaceutical formulation. The topical anesthetic agent may be provided in any suitable form. For example, it may be provided as a solution, gel, ointment, etc.

An antiseptic agent may also be applied on the ocular surface before placement of the device on the eye. Examples of suitable antiseptic agents include, but are not limited to, iodine, povidone-iodine (Betadine®), chlorhexidine, soap, antibiotics, salts and derivatives thereof, and combinations thereof. The antiseptic agent may or may not be applied in combination with a topical anesthetic agent. When the antiseptic comprises povidone-iodine (Betadine®), the concentration of povidone-iodine may range from about 1% to about 10%, from about 2.5% to about 7.5%, or from about 4% to about 6%.

During the drug delivery process, the devices described here may be configured so that the injection needle enters the eye at the right angle that is perpendicular to the eye wall (sclera). In other instances, the device may be configured so that the injection needle enters through the cornea into the anterior chamber of the eye parallel to the iris plane.

III. SYSTEMS AND KITS

Systems and kits that include the intraocular drug delivery devices are also described herein. The kits may include one or more integrated drug delivery devices. Such devices may be preloaded with an active agent. When a plurality of preloaded devices are included, they may be separately packaged and contain the same active agent or different active agents, and contain the same dose or different doses of the active agent.

The systems and kits may also include one or more separately packaged devices that are to be manually loaded. If the devices are to be manually loaded prior to use, then one or more separately packaged active agents may be incorporated into the kit. Similar to the preloaded device system or kit, the separately packaged active agents in the systems and kits here may be the same or different, and the dose provided by each separately packaged active agent may be the same or different.

Of course, the systems and kits may include any combination of preloaded devices, devices for manual loading, and active agents. It should also be understood that instructions for use of the devices will also be included. In some variations, one or more separately packaged measuring components may be provided in the systems and kits for removable attachment to the devices. Topical anesthetic agents and/or antiseptic agents may also be included.

IV. EXAMPLES

The following example serves to more fully describe the manner of using the above-described intraocular injection devices. It is understood that this example in no way serves to limit the scope of the invention, but rather is presented for illustrative purposes.

Example 1: Resistance Force Generated by the Dynamic Sleeve

An intraocular injection device comprising a 30-gauge needle covered by a dynamic sleeve (a bi-tapered design with each end of the sleeve tapered) was fixed onto an Imada tensile testing bed and moved against an Imada 10 N force gauge at a rate of 10 mm/minute. The resistance force was measured while the sleeve was pushed back to expose the needle simulating the movement of the sleeve in practice. This produced a "U"-shaped force plotted against the sleeve displacement curve, as shown in FIG. 46. The resistance force at the beginning and the end of sleeve movement path was greater than that in the middle of the path. In FIG. 46, the illustrated range of resistance force generated may be between zero Newton and about 2 Newton or between about 0.1 Newton and about 1.0 Newton.

In one instance, the resistance force at the beginning of the sleeve path equaled the force required for the 30- or 31-gauge needle to penetrate through the human sclera (e.g., between 0.2 Newton and 0.5 Newton). When a using a higher-resistance sleeve was employed, the resistance force at the beginning of the sleeve path was greater than the force required for the 30- or 31-gauge needle to penetrate through the human sclera (e.g., over 1 Newton). However, the force was low enough to be comfortable for the patient and avoid potential damage to the eye (e.g., to avoid increase in intra-ocular pressure over 60 mmHg). In the middle portion of the sleeve movement path, the force approached zero Newton.

The invention claimed is:

1. An injection device for intraocular drug delivery through an injection site comprising:
   a dynamic resistance component having a proximal end and a distal end;
   an ocular contact surface at the dynamic resistance component distal end;
   a conduit having a proximal end, a distal end, and a lumen extending therethrough; and
   a sectoral measuring component coupled to the ocular contact surface and having a central core, the central core having a circumference and comprising a plurality of members including a first member and a second member extending radially outwardly away from a longitudinal axis and the circumference, each of the plurality of members being sized and configured to touch a limbus line of an eye, wherein the sectoral measuring component can be rotated to a first orientation in which only a tip of the first member touches the limbus line when the tip of the first member is perpendicular to the limbus line of the eye indicating that the injection site is localized at a first distance from the limbus line; wherein the sectoral measuring component can be rotated to a second orientation in which the tip of the first member and a tip of the second member touches the limbus line when the tip of the first member and the tip of the second member is perpendicular to the limbus line indicating that the injection site is localized at a second distance from the limbus line different from the first distance,
   wherein the ocular contact surface has a perimeter, and the perimeter encloses a fixed shape,
   wherein the dynamic resistance component has a first configuration in which the conduit is completely circumscribed by the dynamic resistance component distally, and a second configuration in which the conduit extends distally beyond the dynamic resistance component for intraocular injection.

2. The injection device of claim 1, wherein the plurality of radially extending members are configured to span between 1 degree and 180 degrees of arc around the circumference of the central core.

3. The injection device of claim 1, wherein the plurality of radially extending members are configured to span between 45 degrees and 90 degrees of arc around the circumference of the central core.

4. The injection device of claim 1, wherein the sectoral measuring component is configured to rotate about the longitudinal axis.

5. The injection device of claim 1, wherein the dynamic resistance component comprises a dynamic sleeve.

6. An device for intraocular drug delivery through an injection site comprising:
   a sectoral measuring component having a central core, the central core having a circumference and comprising a plurality of members including a first member and a second member extending radially outwardly away from a longitudinal axis and the circumference, each of the plurality of members being sized and configured to touch a limbus line of an eye, wherein the sectoral measuring component can be rotated to a first orientation in which a tip of only the first member touches the limbus line when the tip of the first member is perpendicular to the limbus line indicating that the injection site is localized at a first distance from the limbus line; wherein the sectoral measuring component can be rotated to a second orientation in which the tip of the first member and a tip of the second member touches the limbus line when the tip of the first member and the tip of the second member is perpendicular to the limbus line indicating that the injection site is localized at a second distance from the limbus line different from the first distance; and
   a conduit having a proximal end, a distal end, and a lumen extending therethrough.

7. An injection device for drug delivery through an injection site comprising:
   a dynamic resistance component having a proximal end and a distal end;
   an atraumatic patient contact surface at the dynamic resistance component distal end;
   a conduit having a proximal end, a distal end, and a lumen extending therethrough; and
   a sectoral measuring component coupled to the atraumatic patient contact surface and having a central core, the central core having a circumference and comprising a plurality of members including a first member and a second member extending radially outwardly away from a longitudinal axis and the circumference, each of the plurality of members being sized and configured to touch a line on a patient, wherein the sectoral measuring component can be rotated to a first orientation in which only a tip of the first member touches the line when the tip of the first member is perpendicular to the line of indicating that the injection site is localized at a first distance from the line; wherein the sectoral measuring component can be rotated to a second orientation in which the tip of the first member and a tip of the second member touches the line when the tip of the first member and the tip of the second member is perpendicular to the line indicating that the injection site is localized at a second distance from the line different from the first distance,
   wherein the atraumatic patient contact surface has a perimeter, and the perimeter encloses a fixed shape,
   wherein the dynamic resistance component has a first configuration in which the conduit is completely circumscribed by the dynamic resistance component distally, and a second configuration in which the conduit extends distally beyond the dynamic resistance component for intraocular injection.

* * * * *